( 12 ) United States Patent
Rosenquist et al.

(10) Patent No.: US 10,172,846 B2
(45) Date of Patent: Jan. 8, 2019

(54) HCV NS-3 SERINE PROTEASE INHIBITORS

(71) Applicant: Medivir AB, Huddinge (SE)

(72) Inventors: Asa Rosenquist, Huddinge (SE);
Fredrik Thorstensson, Linkoping (SE);
Per-Ola Johansson, Linkoping (SE);
Ingemar Kvarnstrom, Linkoping (SE);
Bertil Samuelsson, Huddinge (SE);
Hans Wallberg, Huddinge (SE)

(73) Assignee: Medivir AB, Huddinge (SE)

( * ) Notice: Subject to any disclaimer, the term of this patent is extended or adjusted under 35 U.S.C. 154(b) by 19 days.

(21) Appl. No.: 15/470,599

(22) Filed: Mar. 27, 2017

(65) Prior Publication Data

US 2017/0196849 A1    Jul. 13, 2017

Related U.S. Application Data

(60) Continuation of application No. 12/642,984, filed on Dec. 21, 2009, now abandoned, which is a division of (Continued)

(30) Foreign Application Priority Data

| Jan. 30, 2004 | (SE) | 0400199 |
| May 19, 2004 | (SE) | 0401288 |
| Oct. 22, 2004 | (SE) | 0402562 |

(51) Int. Cl.

| A61K 31/47 | (2006.01) |
| C07C 235/40 | (2006.01) |
| C07C 237/04 | (2006.01) |
| C07C 237/10 | (2006.01) |
| C07C 247/04 | (2006.01) |
| C07C 271/22 | (2006.01) |
| C07C 281/02 | (2006.01) |
| C07C 309/73 | (2006.01) |
| C07C 311/51 | (2006.01) |
| C07D 207/16 | (2006.01) |
| C07D 215/233 | (2006.01) |
| C07D 245/04 | (2006.01) |
| C07D 401/12 | (2006.01) |
| C07D 405/14 | (2006.01) |
| C07D 409/14 | (2006.01) |

(Continued)

(52) U.S. Cl.
CPC ............ *A61K 31/47* (2013.01); *C07C 235/40* (2013.01); *C07C 237/04* (2013.01); *C07C 237/10* (2013.01); *C07C 247/04* (2013.01); *C07C 271/22* (2013.01); *C07C 281/02* (2013.01); *C07C 309/73* (2013.01); *C07C 311/51* (2013.01); *C07D 207/16* (2013.01); *C07D 215/20* (2013.01); *C07D 215/233* (2013.01); *C07D 245/04* (2013.01); *C07D 401/12* (2013.01); *C07D 405/14* (2013.01); *C07D 409/14* (2013.01); *C07D 413/14* (2013.01); *C07D 417/04* (2013.01); *C07D 417/14* (2013.01); *C07D 487/04* (2013.01); *C07K 5/0205* (2013.01); *C07K 5/06034* (2013.01); *C07K 5/06052* (2013.01); *C07C 2601/02* (2017.05); *C07C 2601/08* (2017.05); *C07C 2601/10* (2017.05)

(58) Field of Classification Search
None
See application file for complete search history.

(56) References Cited

U.S. PATENT DOCUMENTS

| 6,265,380 B1 | 7/2001 | Tung et al. |
| 7,125,845 B2 | 10/2006 | Wu et al. |

(Continued)

FOREIGN PATENT DOCUMENTS

| EP | 0443132 | 8/1991 |
| EP | 0126587 | 11/1994 |

(Continued)

OTHER PUBLICATIONS

Trozzi, Caterina et al, "In vitro selection and characterization of hepatitis c virus serine protease variants reisstant to an active site peptide inhibitor." J. Virol. (2003) 77(6) p. 3669-3679.*
"Acute Viral Hepatitis", Merck Manual, http://merckmanuals.com/professional/hepatic_and_biliary_disorders/hepatitis/acute_vital_hepatitis.html?gt=flvivirus&alt=sh, accesses Jul. 11, 2012, 7 pages.
"Dengue", Merck Manual, http://merckmanuals.com/professional/infectious_diseases/arboviridae_arenaviridae_and_filoviridae/dengue.html?gt=flvivirus&alt=sh, accessed Jul. 11, 2012, 2 pages.
"Dengue", www.medterms.com/script/main/art.asp?articlekey=6625, Accessed on Feb. 26, 2008, 1 page.

(Continued)

*Primary Examiner* — Fred H Reynolds
(74) *Attorney, Agent, or Firm* — Baker & Hostetler LLP

(57) ABSTRACT

Methods drawn to peptidomimetic compounds which inhibit the NS3 protease of the hepatitis C virus (HCV), are described. The compounds have the formula (VI) where the variable definitions are as provided in the specification. The compounds comprise a carbocyclic P2 unit in conjunction with a novel linkage to those portions of the inhibitor more distal to the nominal cleavage site of the native substrate, which linkage reverses the orientation of peptidic bonds on the distal side relative to those proximal to the cleavage site.

21 Claims, No Drawings

Related U.S. Application Data application No. 10/572,349, filed as application No. PCT/SE2005/000097 on Jan. 28, 2005, now Pat. No. 7,671,032.

(51) Int. Cl.

| | | |
|---|---|---|
| *C07D 413/14* | (2006.01) | |
| *C07D 417/04* | (2006.01) | |
| *C07D 417/14* | (2006.01) | |
| *C07D 487/04* | (2006.01) | |
| *C07K 5/02* | (2006.01) | |
| *C07K 5/062* | (2006.01) | |
| *C07D 215/20* | (2006.01) | |

(56) References Cited

U.S. PATENT DOCUMENTS

| | | |
|---|---|---|
| 7,608,590 B2 | 10/2009 | Rosenquist et al. |
| 7,659,245 B2 | 2/2010 | Simmen et al. |
| 7,666,834 B2 | 2/2010 | Simmen et al. |
| 8,148,399 B2 | 4/2012 | Simmen et al. |
| 8,227,407 B2 | 7/2012 | Simmen et al. |
| 9,023,808 B2 | 5/2015 | Simmen et al. |
| 2003/0186895 A1 | 10/2003 | Liinas-Brunet et al. |
| 2004/0048802 A1 | 3/2004 | Ripka et al. |

FOREIGN PATENT DOCUMENTS

| | | |
|---|---|---|
| EP | 1043399 | 10/2000 |
| EP | 1090997 | 4/2001 |
| EP | 1408031 | 4/2004 |
| WO | WO 99/07733 | 2/1999 |
| WO | WO 99/07734 | 2/1999 |
| WO | WO 2000/009543 | 2/2000 |
| WO | WO 2000/009558 | 2/2000 |
| WO | WO 2000/047561 | 8/2000 |
| WO | WO 2000/059929 | 10/2000 |
| WO | WO 2001/074768 | 10/2001 |
| WO | WO 2002/008198 | 1/2002 |
| WO | WO 2002/060926 | 8/2002 |
| WO | WO 2003/035060 | 5/2003 |
| WO | WO 2003/053349 | 7/2003 |
| WO | WO 2003/062228 | 7/2003 |
| WO | WO 2003/062265 | 7/2003 |
| WO | WO 2003/064416 | 8/2003 |
| WO | WO 2003/064455 | 8/2003 |
| WO | WO 2003/064456 | 8/2003 |
| WO | WO 2003/066103 | 8/2003 |
| WO | WO 2003/087092 | 10/2003 |
| WO | WO 2003/099274 | 12/2003 |
| WO | WO 2003/099316 | 12/2003 |
| WO | WO 2004/009121 | 1/2004 |
| WO | WO 2004/026896 | 4/2004 |
| WO | WO 2004/032827 | 4/2004 |
| WO | WO 2004/037855 | 5/2004 |
| WO | WO 2004/039833 | 5/2004 |
| WO | WO 2004/039970 | 5/2004 |
| WO | WO 2004/043339 | 5/2004 |
| WO | WO 2004/072243 | 8/2004 |
| WO | WO 2004/092161 | 10/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/103996 | 12/2004 |
| WO | WO 2004/113365 | 12/2004 |
| WO | WO 2005/010029 | 2/2005 |
| WO | WO 2005/073195 | 8/2005 |
| WO | WO 2005/073216 | 8/2005 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014927 | 2/2007 |
| WO | WO 2007/017144 | 2/2007 |

OTHER PUBLICATIONS

"Encephalitis", www.medterms.com/script/main/art.asp?articlekey=3231, Accessed on Feb. 26, 2008, 1 page.

"Flavivirus", www.medterms.com/script/main/art.asp?articlekey=6502, Accessed on Feb. 26, 2008, 1 page.

"Hepatitis", Mayo Clinic, http://mayoclinic.com/health/hepatitis-a/DS00397/DSEcTION=treatments-and-drugs, accessed Jul. 11, 2012, 1 page.

"Yellow Fever", Merck Manual, http://merckmanuals.com/professional/infectious_diseases/arboviridae_arenaviridae_and_filoviridae/yellow_fever.html?gt=flvivirus&alt=sh, accessed Jul. 11, 2012, 2 pages.

Goudreau et al., "NMR Structural Characterization of Peptide Inhibitors Bound to the Hepatitis C Virus NS3 Protease: Design of a New P2 Substituent", J. Med. Chem., 2004, 47, 123-132.

Llinas-Brunet et al., "A Systematic Approach to the Optimization of Substrate-Based Inhibitors of the Hepatitis C Virus NS3 Protease: Discovery of Potent and Specific Tripeptide Inhibitors", J. Med. Chem., 2004, 47, 6584-6594.

Zanotti et al, "Synthesis of analogues of amaninamide, an amatoxin from the white *Amanita virosa* mushroom", Int. J. Peptide Protein Res, 1987, 450-459.

Zanotti et al, "Synthesis of Ile3-Amaninamide and its Diastereoisomeric (S)-Sulfoxide from the Analogs of Amanin", Int. J. Peptide Protein Res, 1981, 162-168.

\* cited by examiner

HCV NS-3 SERINE PROTEASE INHIBITORS

CROSS REFERENCE TO RELATED APPLICATIONS

This application is a continuation of U.S. application Ser. No. 12/642,984, filed Dec. 21, 2009, which is a divisional of U.S. application Ser. No. 10/572,349, filed Jan. 2, 2007, which is the National Stage filing of International Application No. PCT/SE2005/000097, filed Jan. 28, 2005, which claims the benefit of SE0400199-6, filed Jan. 30, 2004, SE 0401288-6, filed May 19, 2004, and SE 0402562-3, filed Oct. 22, 2004, the entireties of which are incorporated by reference herein.

TECHNICAL FIELD

This invention relates to novel inhibitors of the NS3 serine protease of the flavivirus HCV and to methods for their use in the treatment or prophylaxis of HCV.

BACKGROUND ART

The NS3 serine protease of HCV is a multifunctional protein which contains a seine protease domain and a RNA helicase domain. The protease cofactor NS4A, which is a relatively small protein, is absolutely required for enhanced serine protease activity. The NS3 serine protease is essential in the viral lifecycle. From analysis of the substrate binding site as revealed by X-ray crystal structure, it has been shown that the binding site of the NS3 protease is remarkably shallow and solvent exposed making small molecule inhibitor design a challenge.

It is believed that two HCV protease inhibitors have entered clinical trials, namely Boehringer Ingelhelm's BILN-2061 disclosed in WO 0059929 and Vertex' VX-950 disclosed in WO 0387092. A number of similar peptidomimetic HCV protease inhibitors have also been proposed in the academic and patent literature. Common for the vast majority of such prior art peptidomimetics is the presence of an L-proline derivative at the P2 position of the inhibitor and interacting with the S2 subsite of the HCV protease enzyme. In the case of BILN-2061, the L-proline is 4-substituted with a quinoline ether, whereas VX-950 has a carboyclic ring fused to the L-proline ring. Most peptidomimetics additionally comprise additional L-amino acid derivatives peptide bonded at the P3 position, with many proposed inhibitors also including additional L-amino acid derivatives extending into P4, P5 and P6.

It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168Y and/or A165S. Treatment paradigms for HCV will thus have to resemble HIV treatment, where drug escape mutations also arise readily. Accordingly, additional drugs with different resistance patterns will consistently be required to provide falling patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$ is essential to slow down the development of drug escape mutants and achieving the necessary pharmacokinetics and drug metabolism to allow such trough levels provides a stringent challenge to drug design. The strongly peptidomimetic nature of prior art HCV protease inhibitors, with multiple peptide bonds in native configurations poses pharmacokinetic hurdles to effective dosage regimes.

BRIEF DESCRIPTION OF THE INVENTION

In accordance with a first aspect of the invention, there are provided compounds of the formula VI:

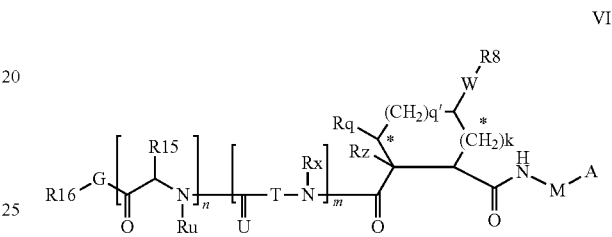

VI wherein
A ss $C(=O)OR^1$, $C(=O)NHSO_2R^2$, $C(=O)NHR^3$, or $CR^4R^{4'}$ wherein;
$R^1$ is hydrogen, $C_1$-$C_6$alkyl, $C_0$-$C_3$alkylcarbocyclyl, $C_0$-$C_3$alkylheterocyclyl;
$R^2$ is $C_1$-$C_6$alkyl, $C_0$-$C_3$alkylcarbocyclyl, $C_0$-$C_3$alkylheterocyclyl;
$R^3$ is $C_1$-$C_6$alkyl, $C_0$-$C_3$alkylcarbocyclyl, $C_0$-$C_3$alkylheterocyclyl, —$OC_1$-$C_6$alkyl, —$OC_0$-$C_3$alkylcycarbocyclyl, —$OC_0$-$C_3$alkylheterocyclyl;
$R^4$ is halo, amino, or OH; or $R^4$ and $R^{4'}$ are =O;
$R^{4'}$ is $C_1$-$C_6$alkyl, $C_0$-$C_3$alkylcarbocyclyl, $C_0$-$C_3$alkylheterocyclyl; wherein
$R^2$, $R^3$, and $R^{4'}$ are each optionally substituted from 1 to 3 substituents independently selected from the group consisting of times with halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, Y—NRaRb, Y—O—$R_b$, Y—$C(=O)Rb$, Y—$(C=O)NRaRb$, Y—$NRaC(=O)Rb$, Y—$NHSO_pRb$, Y—$S(=O)_pRb$, Y—$S(=O)_pNRaRb$, Y—$C(=O)Orb$ and Y—$NRaC(=O)ORb$;
Y is independently a bond or $C_1$-$C_3$alkylene;
Ra is independently H or $C_1$-$C_3$alkyl;
Rb is independently H, $C_1$-$C_6$alkyl, $C_0$-$C_3$alkylcarbocyclyl or $C_0$-$C_3$alkylheterocyclyl;
p is independently 1 or 2;
M is $CR^7R^{7'}$ or NRu;
Ru is H or $C_1$-$C_3$alkyl;
$R^7$ is $C_1$-$C_6$alkyl, $C_0$-$C_3$alkyl$C_3$-$C_7$cycloalkyl, or $C_2$-$C_6$alkenyl, any of which is optionally substituted with 1-3 halo atoms, or an amino, —SH or $C_0$-$C_3$alkylcycloalkyl group, or $R^7$ is J;
$R^{7'}$ is H or taken together with $R^7$ forms a $C_3$-$C_6$cycloalkyl ring optionally substituted with $R^{7'a}$ wherein;
$R^{7'a}$ is $C_1$-$C_6$alkyl, $C_3$-$C_5$cycloalkyl, $C_2$-$C_6$alkenyl any of which may be optionally substituted with halo; or $R^{7'a}$ is J;
q' is 0 or 1 and k is 0 to 3;
Rz is H, or together with the asterisked carbon forms an olefinic bond;
Rq is H or $C_1$-$C_6$alkyl;

W is —CH$_2$, —O—, —OC(=O)H—, —OC(=O)—, —S—, —NH—, —NRa, —NHSO$_2$—, —NHC(=O)NH— or —NHC(=O)—, —NHC(=S)NH— or a bond;

R$^8$ is a ring system containing 1 or 2 saturated, partially saturated or unsaturated rings each of which has 4-7 ring atoms and each of which has 0 to 4 hetero atoms selected from S, O and N, the ring system being optionally spaced from W by a C$_1$-C$_3$alkyl group; or R$^8$ is C$_1$-C$_6$alkyl; any of which R$^8$ groups can be optionally mono, di, or hi substituted with R$^9$, wherein R$^9$ is independently selected from the group consisting of halo, oxo, nitrile, azido, nitro, C$_1$-C$_6$alkyl, C$_0$-C$_3$alkylcarbocyclyl, C$_0$-C$_3$alkylheterocyclyl, NH$_2$CO—, Y—NRaRb, Y—O—Rb, Y—C(=O)Rb, Y—(C=O)NRaRb, Y—NRaC(=O)Rb, Y—NHSO$_p$Rb, YS(=O)$_p$Rb, Y—S(=O)$_p$NRaRb, Y—C(O)Orb and Y—NRaC(=O)ORb; wherein said carbocyclyl or heterocycyl moiety is optionally substituted with R$^{10}$; wherein R$^{10}$ is C$_1$-C$_6$alkyl, C$_3$-C$_7$cycloalkyl, C$_1$-C$_6$alkoxy, amino, sulfonyl, (C$_1$-C$_3$ alkyl)sulfonyl, NO$_2$, OH, SH, halo, haloalkyl, carboxyl, amido, Rx is H or C$_1$-C$_5$ alkyl; or Rx is J;

T is —CHR$^{11}$— or —NRd-, where Rd is H, C$_1$-C$_3$alkyl; or Rd is J;

R$^{11}$ is H, C$_1$-C$_6$alkyl, C$_0$-C$_3$alkylcarbocyclyl, C$_0$-C$_3$alkylheterocyclyl, any of which can be substituted with halo, oxo, nitrile, azido, nitro, C$_1$-C$_6$alkyl, C$_0$-C$_3$alkylcarbocyclyl, C$_0$-C$_3$alkylheterocyclyl, NH$_2$CO—, Y—NRaRb, Y—O—Rb, Y—C(=O)Rb, Y—(C=O)NRaRb, Y—NRaC(O)Rb, Y—NHSO$_p$Rb, Y—S(=O)$_p$Rb, Y—S(=O)$_p$NRaRb, Y—C(=O)ORb, Y—NRaC(=O)ORb; or R$^{11}$ is J;

J, if present, is a single 3 to 10-membered saturated or partially unsaturated alkylene chain extending from the R$^7$/R$^{7'}$ cycloalkyl, or from the carbon atom to which R$^7$, is attached to one of Rd, R, Rx, Ry or R$^{11}$ to form a macrocycle, which chain is optionally interrupted by one to three heteroatoms independently selected from: —O—, —S— or —NR$^{12}$—, and wherein 0 to 3 carbon atoms in the chain are optionally substituted with R$^{14}$; wherein;

R$^{12}$ is H, C$_1$-C$_6$ alkyl, C$_3$-C$_6$cycloalkyl, or C(=O)R$^{13}$;

R$^{13}$ is C$_1$-C$_6$alkyl, C$_0$-C$_3$alkylcarbocyclyl, C$_0$-C$_3$alkylheterocyclyl;

R$^{14}$ is independently selected from the group consisting of H, C$_1$-C$_6$alkyl, C$_1$-C$_6$haloalkyl, C$_1$-C$_6$alkoxy, hydroxy, halo, amino, oxo, thio and C$_1$-C$_6$thioalkyl;

m is 0 or 1; n is 0 or 1;

U is =O or is absent;

R$^{15}$ is H, C$_1$-C$_6$alkyl, C$_0$-C$_3$alkylcarbocyclyl, C$_0$-C$_3$alkylheterocyclyl, any of which can be substituted with halo, oxo, nitrile, azido, nitro, C$_1$-C$_6$ alkyl, C$_0$-C$_3$alkylcarbocyclyl, C$_0$-C$_3$alkylheterocyclyl, NH$_2$CO—, Y—NRaRb, Y—O—Rb, Y—C(=O)Rb, Y—(C=O)NRaRb, Y—NRaC(=O)Rb, Y—NHS(=O)$_p$Rb, Y—S(=O)$_p$Rb, Y—S(=O)$_p$NRaRb, Y—C(=O)ORb, Y—NRaC(=O)ORb;

G is —O—, —NRy-, —NRjNRj-;

Ry is H, C$_1$-C$_3$ alkyl; or Ry is J;

one Rj is H and the other Rj is H or J;

R$^{16}$ is H; or R$^{16}$ is C$_1$-C$_6$alkyl, C$_0$-C$_3$alkylcarbocyclyl, C$_0$-C$_3$alkylheterocyclyl, any of which can be substituted with halo, oxo, nitrile, azido, nitro, C$_1$-C$_6$alkyl, C$_0$-C$_3$alkylcarbocyclyl, C$_0$-C$_3$alkylheterocyclyl, NH$_2$CO—, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(O)$_p$NRaRb, Y—C(=O)ORb, Y—NRaC(=O)ORb;

or a pharmaceutically acceptable salt or prodrug thereof.

Without in any way wishing to be bound by theory, or the ascription of tentative binding modes for specific variables, the notional concepts P1, P2, P3, and P4 as used herein are provided for convenience only and have substantially their conventional meanings, as illustrated by Schechter & Berger, (1976) Biochem Biophys Res Comm 27 157-162, and denote those portions of the inhibitor believed to fill the S1, S2, S3 and S4 subsites respectively of the enzyme, where S1 is adjacent the cleavage site and S4 remote from the cleavage site. Regardless of binding mode, the components defined by Formula VI etc are intended to be within the scope of the invention. For example it s expected that capping group R$^{16}$-G may interact with the S3 and S4 subsites especially when m and/or n is 0.

The various embodiments of the present invention can be notionally represented as R$^{16}$-G-P4-P3-P2-P1, wherein P3 and/or P4 may be absent P1, P3 and P4 each represents a building block constituted of a derivative of a natural or unnatural amino acid, P2 is a substituted carbocydclic residue and G-R$^{16}$ is a capping group. The building blocks are typically linked together by amide bonds which are reversed relative to each other on each side of the P2 building block in the compounds of the invention.

Additional aspects of the invention include a pharmaceutical composition comprising a compound of the invention as defined above and a pharmaceutically acceptable carrier or diluent therefor.

The compounds and compositions of the invention have utility in methods of medical treatment or prophylaxis of HCV infections in humans. Accordingly, a further aspect of the invention is the use of a compound as defined above in therapy such as the manufacture of a medicament for the prophylaxis or treatment of flavivirus infections in humans or animals. Exemplary flavivirus include BVDV, dengue and especially HCV.

In the compounds of the invention the amide bond linking the P2 and P3 together is reversed relative to the amide bond linking the P1 and P2, i.e. the amino acid derivatives, P1 and P3, on each side of the P2 scaffold are both coupled through their amino functions to the acid groups on each side of the P2 scaffold. This means that the side chains of the P3 and P4 (including the R$^{16}$ cap to the extent this interacts with S3 or S4) point in the opposite direction compared to in a native peptide substrate. Another consequence of the reversed P3 and P4 amino acids is that the side chains of these amino acids are displaced one atom outwardly relative to a native peptide substrate.

Change of direction of the P3 and P4 side chains in this fashion would be expected to favour non-natural D stereo-chemistries for the pocket filing groups (eg side chains) of P3 and/or P4 and/or R$^{16}$. Indeed, such compounds are typically highly active and within the scope of the invention. However, it has been surprisingly found that even compounds of the invention bearing L-amino acid side chains at P3 and/or P4 exhibit good activity, notwithstanding that the respective entity must approach the S3 or S4 pocket from a different angle relative to a native peptide substrate. Accordingly L-stereochemistry at R$^{11}$ and/or R$^{15}$ and/or the corresponding configuration at R$^{16}$ to mimic L stereochemistry represents a favoured aspect of the invention.

The different angle of approach to the S3 and/or S4 pockets also has implications for the ability of the compounds of the invention to avoid resistance patterns exhibited by prior art HCV protease inhibitors which hitherto have all had a conventional peptide backbone of natural or non-natural L-amino acid residues. As with the reverse transcriptase of HIV which is notorious for quickly generating drug escape mutants under the selective pressure of antiviral therapy, the RNA dependent RNA polymerase NS5A of HCV has a very poor proof reading capacity. This in turn means that the HCV polymerase is highly error prone and it is likely that characteristic resistance patterns will arise when HCV antivirals are administered over long periods. Even before launch, it is apparent that BILN 2061 with a substantially peptidic backbone (albeit macrocyclised) and Vertex' NS3 protease inhibitor VX-950 with a linear peptide backbone at P3 and P4 quickly give rise to characteristic resistance mutations at positions 155, 156 or 168 of the NS3 protease (Lin et al J Biol Chem 2004 279(17):17808-17).

A preferred group of compounds of the invention comprises those wherein P1 represents a hydrazine derivative, that is M is NRu where Ru is typically H or $C_1$-$C_3$alkyl. Compounds wherein M is $CR^7R^{7'}$ constitute a further preferred aspect of the Invention.

Preferred embodiments wherein M is $CR^{7'}$ in formulae VI include formulae VIA below.

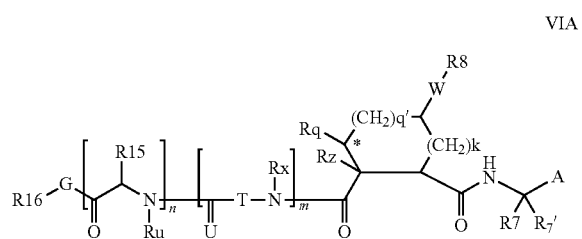

VIA

Preferred values for q' and k in formula VI include 1:1, 1:2, 1:3, 22, 2:3, more preferably 0:2 and 0:0; and most preferably 0:1, in which case preferred compounds have one of the partial structures:

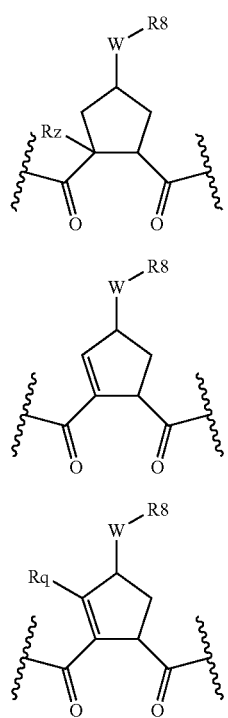

especially where Rz is H or Rq is H or methyl.

Compounds of the invention may comprise both a P3 and a P4 function, viz m and n are each 1. Favoured embodiments within Formula VI comprising both a P3 and P4 function include formula VIda-VIdb below:

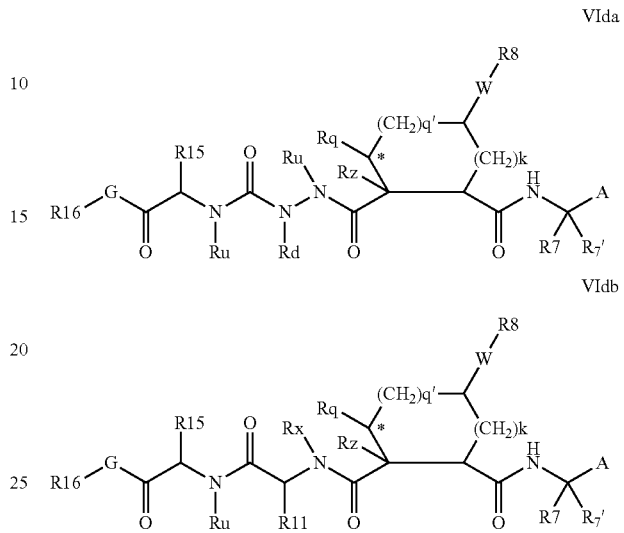

Alternative embodiments include the structures corresponding to VIda, and VIdb wherein M is NRu.

Alternative configurations of the compounds of the invention comprise a P3, but no P4 function, viz m is 1 and n is zero. Favoured embodiments within Formula VI comprising a P3, but no P4 include formula VIea-VIeb below:

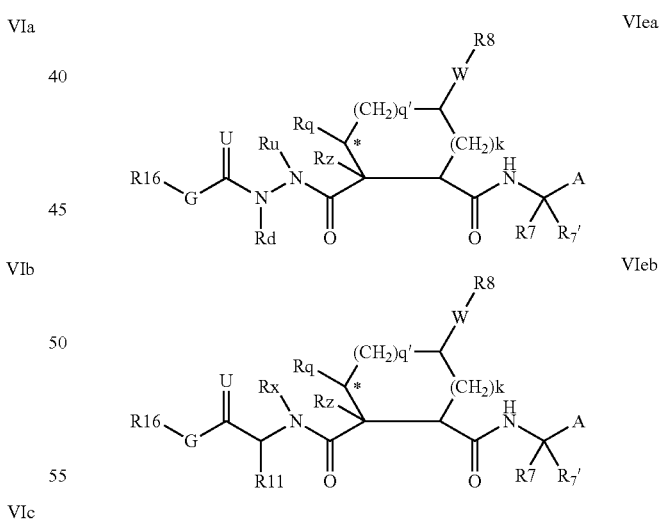

Alternative embodiments include the structures corresponding to VIea and VIeb wherein M is NRu.

Still further alternative configurations of the compounds of the invention include those where m and n are zero and thus groups $R^{16}$-G abut P2, but as mentioned above, the capping group R16-G may interact favourably with S3 and/or S4.

Favoured embodiments within Formula VI wherein m and n are zero include those of formula VIfa below:

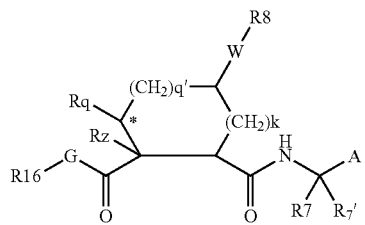

VIfa

Alternative embodiments include the structures corresponding to VIfa, wherein M is NRu.

The compounds of the invention may comprise linear molecules, as depicted above. Alternatively, in embodiments wherein $R^7$ and $R^{7'}$ together define a spiro cycloalkyl group, such as spiro-cyclopropyl, the compounds of the invention may be configured as macrocycles, wherein a linking group J extends between one of Rj, Rx, Ry, Rd or $R^{11}$ of Formula VI. Alternatively the macrocycle J may extend from the carbon adjacent $R^7$ to one of RJ, Rx, Ry, Rd or Ru.

Favoured embodiments of such macrocyclic structures within formula VI wherein m is 0 and n is 1 include those of the formula VIga-VIgc below:

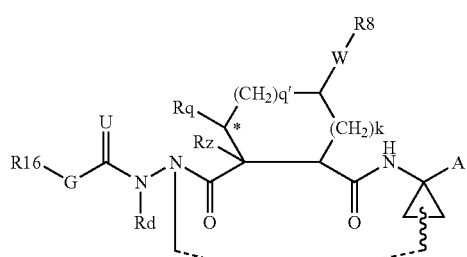

VIga

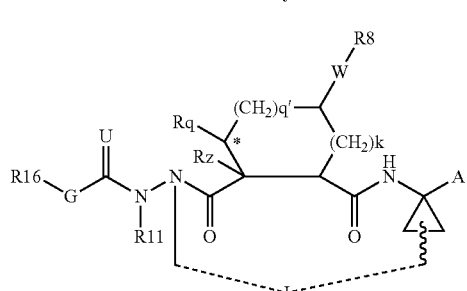

VIgb

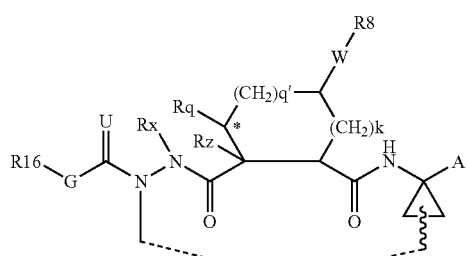

VIgc

The corresponding structures wherein the J chain bonds to the carbon adjacent $R^7$ are also favoured.

Favoured embodiments of macrocyclic structures within formula VI comprising both a P3 and P4 functions, i.e. wherein both m and n are 1, include those of the formula VIha-VIhc below:

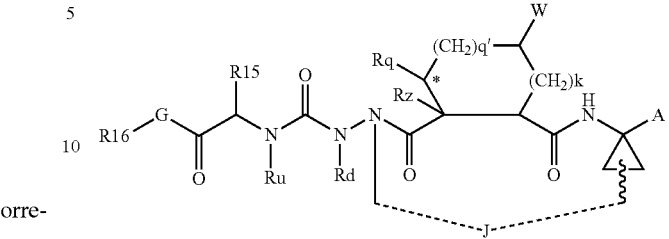

VIha

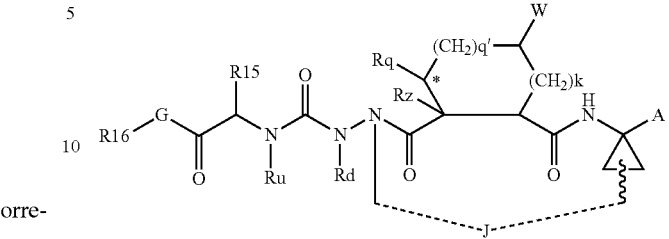

VIhb

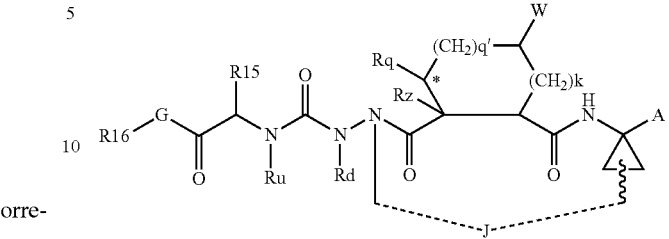

VIhc

The corresponding structures wherein the J chain bonds to the carbon adjacent $R^7$ are also favoured.

Favoured macrocyclic structures within Formula VI, wherein both of the P3 and P4 functions are absent, i.e. wherein m and n are each 0, include those of the formulae VIhe-VIhf below.

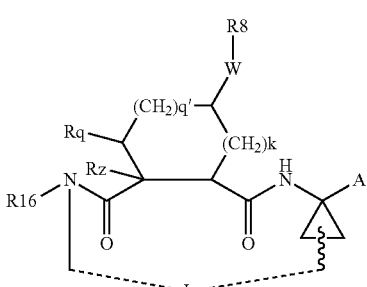

VIhe

-continued

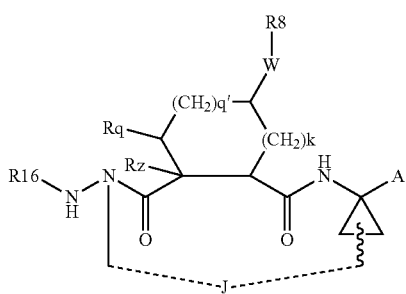

VIhf

The corresponding structures wherein the J chain bonds to the carbon adjacent $R^7$ are also favoured.

In general, in the optionally macrocyclic structures such as those illustrated above, linker J is a 3 to 10 chain atom, preferably 4 to 7 chain atom, such as 6 or 6 chain atom, saturated or partially unsaturated alkylene chain, that is an alkylene chain bearing 1 to 3 unsaturated bonds between adjacent carbons, typically one unsaturation. The length of the chain will, of course, depend on whether J extends from Rd, Rx, Rx, Ry, $R^{11}$ or the carbon adjacent $R^7$. Suitable chains are described in detail in WO 00/59929. Typically J will be dimensioned to provide a macrocycle of 13 to 16 ring atoms (including those atoms in the P1, P2 and if present P3 groups contributing to the ring). Conveniently J is dimensioned to provide a macrocycle of 14 or 15 ring atoms.

Conveniently, the J chain contains one or two heteroatoms selected from: O, S, NH, $NC_1$-$C_6$ alkyl or N—C(=O)$C_1$-$C_6$alkyl. More preferably, the J chain optionally contains one heteroatom selected from: NH, or N—C(=O)$C_1$-$C_6$alkyl, most preferably N(Ac). Most preferably, the chain containing a nitrogen atom is saturated. In an alternative embodiment, J contains one heteroatom selected from O or S. The chain may be substituted with $R^{14}$, such as H or methyl.

Typically the J linker structure is saturated. Alternatively, J contains 1 to 3, preferably one double bond, typically spaced one carbon from the cycloakyl $R^7$ function, if present. The double bond may be cis or trans.

Representative examples of J thus include pentylene, hexylene, heptylene, any of which are substituted with $C_1$-$C_6$alkyl, $C_1$-$C_6$haloalkyl, $C_1$-$C_6$alkoxy, hydroxyl, halo, amino, oxo, thio or $C_1$-$C_6$thioalkyl; penten-3-yl, hexen-4-yl, hepten-5-yl, where 3, 4 or 5 refers to a double bond between carbon atoms 3 and 4, 4 and 5 etc.

Convenient $R^7$ and $R^{7'}$ groups include those wherein $R^{7'}$ is H and $R^7$ is n-ethyl, n-propyl, cyclopropyl, cyclopropylmethyl, cyclobutyl, cyclobutylmethyl, 2,2-difluoroethyl, or mercaptomethyl. Preferred embodiments include those wherein $R^7$ is n-propyl or 2,2-difluoroethyl.

Alternative favoured configurations for $R^7$ and R include those wherein $R^{7'}$ is H and $R^7$ is $C_3$-$C_7$ cycloakyl or $C_1$-$C_3$alkyl$C_3$-$C_7$cycloakyl.

Still further favoured configurations for $R^7$ and $R^{7'}$ include those wherein $R^{7'}$ is H and $R^7$ is J.

Alternatively, $R^7$ and $R^{7'}$ together define a spiro-cycloalkyl function, such as a spiro-cyclobutyl ring, and more preferably a spiro-cyclopropyl ring. "Spiro" in this context simply means that the cycloakyl ring shares a single carbon atom with the peptidic backbone of the compound. The ring is substituted or unsubstituted. Preferred substituents include mono or di-substitutions with $R^{7'a}$ wherein $R^{7'a}$ is $C_1$-$C_6$ alkyl, $C_3$-$C_6$cycloalkyl, or $C_2$-$C_6$ alkenyl, any of which is optionally substituted with halo.

Alternatively the substituent may be a J linker as described above. Currently preferred stereochemistries for a spiro-cyclopropyl ring are defined below.

Particularly preferred substituents include $R^{7'a}$ as ethyl, vinyl, cyclopropyl (ie a spiro-cyclopropyl substituent to the spiro cycloalkyl ring of $R^7$/$R^{7'}$), 1- or 2-bromoethyl, 1- or 2-fluoroethyl, 2-bromovinyl or 2-fluorethyl.

In one embodiment of the invention A is —$CR^4R^{4'}$ as illustrated in detail in PCT/EP03/10595, the contents of which are incorporated by reference.

Convenient $R^{4'}$ groups thus include $C_1$-$C_6$alkyl, such as methyl, ethyl, propyl, ethenyl and —$CHCHCH_3$. Alternative preferred R groups include aryl or heteroaryl such as optionally substituted phenyl, pyridyl, thiazolyl or benzimidazolyl or $C_1$-$C_3$alkylaryl or $C_1$-$C_3$alkylheteroaryl, where the alkyl moiety is methyl, ethyl, propyl, ethenyl and —$CHCHCH_3$. Preferred aryl moieties include optionally substituted phenyl, benzothiazole and benzimidazole.

Favoured $R^4$ groups include —$NH_2$, fluoro or chloro. Alternative preferred $R^4$ groups include —OH and especially =O.

An alternative embodiment for A is C(=O)$NHR^3$, where $R^3$ is optionally substituted $C_0$-$C_3$alkylaryl, $C_0$-$C_3$alkylheteroaryl, $OC_0$-$C_3$alkylaryl or $OC_0$-$C_3$alklylheteroaryl. Appropriate substituents appear in the definitions section below.

An alternative favoured configuration for A s C(=O)$OR^1$, especially where $R^1$ is $C_1$-$C_6$alkyl, such as methyl, ethyl, or tert-butyl and most preferably hydrogen.

A particularly preferred configuration for A is C(=O) $NHSO_2R^2$, especially where $R^2$ is optionally substituted $C_1$-$C_6$alkyl, preferably methyl, or optionally substituted $C_3$-$C_7$cycloakyl, preferably cyclopropyl, or optionally substituted $C_0$-$C_6$alkylaryl, preferably optionally substituted phenyl. Appropriate substituents appear in the definitions section below.

Substituent —W—$R^8$ on the cyclic P2 group can employ any of the proline substituents which are extensively described in WO 00/59929, WO 00/09543, WO 00/09558, WO 99/07734, WO 99/07733, WO 02R/0926, WO03/35060, WO 03/53349, WO03/064416, W=03/86103, WO03/064455, WO03/064456, WO03/62265, WO03/062228, WO03/87092, WO 03/99274, WO03/99316, WO03/99274, WO04/03670, WO04/032827, WO04/037855, WO04/43339, WO04/92161, WO04/72243, 5WO04/93798. WO04/93915, WO04/94452, WO04/101505, WO04/101602, WO04/103996, WO04/13365 and the like.

Favoured W functions include W as —OC(=O)NH—, —OC(=O)—, —NH—, —$NR^{8'}$—, —$NHS(O)_2$— or —NHC(=O)—, especially —OC(=O)NH— or —NH—. Favoured $R^8$ groups for such W functions include optionally substituted $C_0$-$C_3$alkylcarbocyclyl or $C_0$-$C_3$alkylheterocyclyl, including those described in WO0009543, WO0009558 and WO 00/174768. For example ester substituents, —W—$R^8$, on the cyclic P2 group, include those disclosed in WO 01/74768 such as $C_1$-$C_6$alkanoyloxy, $C_0$-$C_3$alkylaryloyloxy, particularly (optionally substituted) benzoyloxy or $C_0$-$C_3$alkylheterocycloyloxy, especially

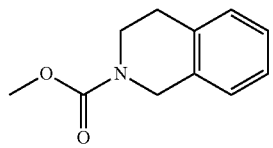

This publication also describes alternative —W—$R^8$ possibilities for example $C_1$-$C_6$alkyl, such as ethyl, isopropyl, $C_0$-$C_3$alkylcarbocyclyl such as cyclohexyl, 2,2-difluoroethyl, —C(═O)NRc, where Rc is $C_1$-$C_6$alkyl, $C_0$-$C_3$alkylcyclopropyl, $C_0$-$C_3$alkylaryl or $C_0$-$C_3$alkylheterocyclyl.

Currently preferred W functions include —S— and especially —O—. Convenient values for $R^8$ in such embodiments include $C_0$-$C_3$alkylaryl, or $C_0$-$C_3$alkylheteroaryl either of which is optionally mono, di, or tri substituted with $R^9$, wherein;
$R^9$ is $C_1$-$C_6$alkyl, $C_1$-$C_6$alkoxy, $NO_2$, OH, halo, trifluoromethyl, amino or amido (such as amino or amido optionally mono- or di-substituted with $C_1$-$C_6$alkyl), $C_0$-$C_3$alkylaryl, $C_0$-$C_3$alkylheteroaryl, carboxyl, aryl or heteroaryl being optionally substituted with $R^{10}$; wherein
$R^{10}$ is $C_1$-$C_6$alkyl, $C_3$-$C_7$cycloalkyl, $C_1$-$C_6$alkoxy, amino (such as amino mono- or di-substituted with $C_1$-$C_6$alkyl), amido (such as $C_1$-$C_5$ alkyl amide), sulfonyl$C_1$-$C_3$alkyl, $NO_2$, OH, halo, trifluoromethyl, carboxyl, or heteroaryl.

Typically, the $C_0$-$C_3$ alkyl component of $R^8$ as $C_0$-$C_3$alkylaryl, or $C_0$-$C_3$alkylheteroaryl is methyl and especially absent, ie $C_0$. The aryl or heteroaryl component s as extensively illustrated in the definition section below.

Preferred $R^9$ include $C_1$-$C_6$ alkyl, $C_1$-$C_6$alkoxy, amino (such as di-($C_1$-$C_3$ alkyl)amino), amide (such as as —NHC(O)$C_1$-$C_6$alkyl or C(═O)NH$C_1$-$C_3$alkyl), aryl or heteroaryl, the aryl or heteroaryl moiety being optionally substituted with $R^{10}$; wherein
$R^{10}$ is $C_1$-$C_6$alkyl, $C_3$-$C_7$cycloalkyl, $C_1$-$C_6$alkoxy, amino (such as mono- or di-$C_1$-$C_3$ alkylamino), amido (such as as —NHC(O)$C_1$-$C_3$yl or C(═O)NH$C_1$-$C_6$alkyl), halo, trifluoromethyl, or heteroaryl.

Preferred $R^{10}$ include $C_1$-$C_6$alkyl, $C_1$-$C_6$alkoxy, amino, amido (such as as —NHC(O)$C_1$-$C_6$alkyl or C(═O)NH$C_1$-$C_6$alkyl) halo, or heteroaryl.

Particularly preferred $R^{10}$ include methyl, ethyl, isopropyl, tertbutyl, methoxy, chloro, amino, amido (such as as —NHC(O)$C_1$-$C_3$alkyl or C(═O)NH$C_1$-$C_6$alkyl), or $C_1$-$C_3$alkyl thiazole.

Favoured embodiments of $R_8$ include 1-naphthylmethyl, 2-naphthylmethyl, benzyl, 1-naphthyl, 2-naphthyl, or quinolinyl, any opf which is unsubstituted, or mono- or disubstituted with $R^8$ as defined, in particular 1-naphthylmethyl, or quinolinyl unsubstituted, mono, or disubstituted with R as defined.

A currently preferred $R^8$ is:

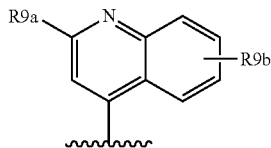

wherein $R^{9a}$ is $C_1$-$C_6$alkyl; $C_1$-$C_6$alkoxy; thio$C_1$-$C_3$alkyl; amino optionally substituted with $C_1$-$C_6$alkyl; $C_0$-$C_3$alkylaryl; or $C_0$-$C_3$alkylheteroaryl, $C_0$-$C_3$alkylheterocyclyl, said aryl, heteroaryl or heterocycle being optionally substituted with $R_{10}$ wherein $R^{10}$ is $C_1$-$C_6$alkyl, $C_3$-$C_7$cycloakyl, $C_1$-$C_6$alkoxy, amino, amido, heteroaryl or heterocyclyl; and
$R^{9b}$ is $C_1$-$C_6$alkyl, $C_1$-$C_6$alkoxy, amino, amido, $NO_2$, OH, halo, trifluoromethyl, carboxyl.

Convenient $R^{9a}$ include aryl or heteroaryl, al optionally substituted with $R^{10}$ as defined, especially where $R^{9a}$ is selected from the group consisted of:

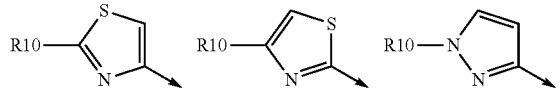

wherein $R^{10}$ is H, $C_1$-$C_6$alkyl, or $C_0$-$C_3$alkyl-$C_3$-$C_6$cycloalkyl, amino (such as amino mono- or di-substituted with $C_1$-$C_6$alkyl), amido (such as as —NHC(O)$C_1$-$C_6$alkyl or C(═O)NH$C_1$-$C_6$alkyl) heteroaryl or heterocyclyl.

$R^{9a}$ is conveniently phenyl and thus $R^8$ is:

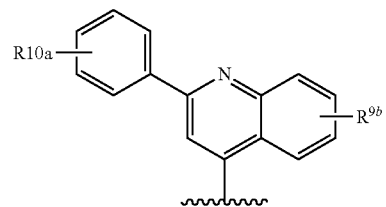

wherein $R^{10a}$ is H, $C_1$-$C_6$alkyl; $C_1$-$C_6$alkoxy; or halo; and $R^{9b}$ is $C_1$-$C_6$ alkyl, $C_1$-$C_6$-alkoxy, amino (such as $C_1$-$C_3$alkylamino), amido (such as as —NHC(O)$C_1$-$C_6$alkyl or C(═O)NH$C_1$-$C_3$alkyl), $NO_2$, OH, halo, trifluoromethyl or carboxyl.

An alternative preferred $R^8$ is:

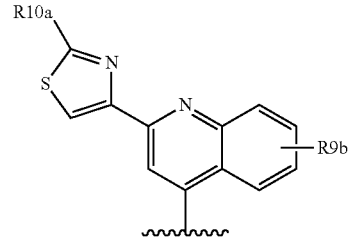

wherein $R^{10a}$ is H, $C_1$-$C_6$alkyl, or $C_0$-$C_3$alkyl-$C_3$-$C_6$cycloalkyl, amino (such as amino optionally mono- or di-substituted with $C_1$-$C_6$alkyl), amido (such as as —NHC(O)$C_1$-$C_6$alkyl or C(O)NH$C_1$-$C_3$alkyl or C(═O)N($C_1$-$C_3$alkyl)$_2$), heteroaryl or heterocyyl; and $R^{9b}$ is $C_1$-$C_6$ alkyl, $C_1$-$C_6$-alkoxy, amino optionally mono- or di-substituted with $C_1$-$C_6$alkyl, amido (such as as —NHC(O)$C_1$-$C_6$alkyl or C(═O)NH$C_1$-$C_3$alkyl or C(═O)N($C_1$-$C_3$alkyl)$_3$), $NO_2$, OH, halo, trifluoromethyl, or carboxyl.

In the immediately above described embodiments $R^{9b}$ is conveniently $C_1$-$C_6$-alkoxy, preferably methoxy.

A further $R^8$ group, for example when W is an ether has the formula

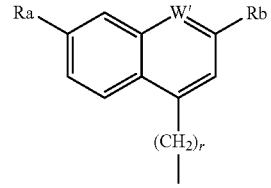

where W is N or CH, r is 0 or 1, Ra' is H, $C_1$-$C_5$ alkyl, $C_0$-$C_3$alkylcycloalkyl, $C_1$-$C_6$alkyloxy, hydroxy or amine and Rb' is H, halo, $C_1$-$C_6$alkyl, $C_0$-$C_3$alkylcycloalkyl, $C_1$-$C_6$alkyloxy, $C_1$-$C_6$thioalkyl, cycloalkyl$C_0$-$C_3$alkyloxy, $C_1$-$C_3$alkyloxy$C_1$-$C_3$alkyl, $C_0$-$C_3$alkylaryl or $C_0$-$C_3$alkylheterocyclyl A particularly preferred ether substituent is 7-methoxy-2-phenyl-quinolin-4-yl oxy.

When W is a bond then $R^8$ is preferably a substituted or unsubstituted heterocyclic ring system as described in WO20041072243 or WO2004/113665.

Representative examples of $R^8$ when W is a bond include the following aromatics which may optionally be substituted: 1H-pyrrole, 1H-imidazole, 1H-pyrazole, furan, thiophene, oxazole, thiazole, isoxazole, isothiazole, pyridine, pyridazine, pyrimidine, pyrazine, phthalazine, quinoxaline, quinazoline, quinoline, cinnoline, 1H-pyrrolo[2,3]-b]pyridine, 1H-indole, 1H-benzoimidazole, 1H-indazole, 7H-purine, benzothiazole, benzooxazole, 1H-imidazo[4, 5-c]pyridine, 1H-imidazo[4,5-b]pyridine, 1, 3-dihydrobenzoimidazol-2-one, 1, 3-dihydro-benzoimidazol-2-thione, 2, 3-dihydro-1H-indole, 1,3-dihydro-indol-2-one, 1H-Indole-2,3-dione, 1, 3-dihydro-benzoimidazole-2-one, 1H, 1H-pyrrolo [2, 3-c]pyridine, benzofuran, benzo[b]thiophene, benzo[d]isoxazole, benzo[d]isothiazol, 1H-quinotin-2-one, 1H-quinolin-4-one, 1H-quinazol-4-one, 9H-carbazole, 1H-quinazolin-2-one.

Additional representative examples of $R^8$ when W is a bond, include the following non-aromatics, which may be optionally substituted: aziridine, azetidine, pyrrolidine, 4,5-dihydro-1H-pyrazole, pyrazolidine, imidazolidin-2-one, imidazolidine-2-thione, pyrrolidin-2-one, pyrolidine-2,5-dione, piperidine-2,6-dione, piperidin-2-one, piperazine-2,6-done, piperazin-2-one, piperazine, morpholine, thiomorpholine-1,1-dioxide, pyrazolidin-3-one, imidazolidine-2,4-dione, piperidine, tetrahydrofuran, tetrahydropyran, [1,4] dioxane, 1,2,3,6-tetrahydropyridine.

Preferred values for $R^8$ when W is a bond, include tetrazole and derivatives thereof. The tetrazole moiety is linked to the cyclic P2 scaffold and optionally substituted as shown below:

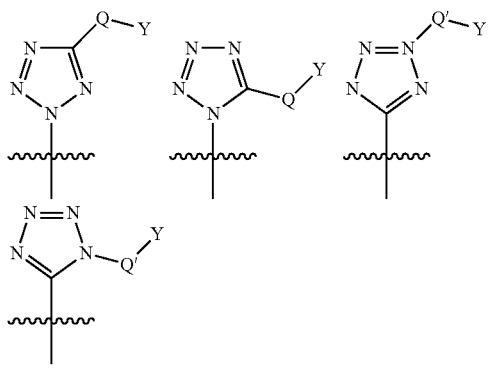

wherein Q* is selected from the group consisting of absent, —CH$_2$—, —O—, —NH—, —N(R$^{1*}$)—, —S—, —S(=O)$_2$— and —(C=O)—; Q* is selected from the group consisting of: absent, —CH$_2$— and —NH; Y* is selected from the group consisting of: H, $C_1$-$C_6$alkyl, $C_0$-$C_3$aryl, $C_0$-$C_3$heterocyclyl and $R^{1*}$ is selected from the group consisting of: H, $C_1$-$C_6$alkyl, carbocyclyl, $C_0$-$C_3$aryl, $C_0$-$C_3$heterocyclyl.

Representative examples of substituted tetrazoles are as described in table 1 of WO2004/072243 and the structures following immediately after, or WO2004/113665.

Further preferred values for $R^8$ when W is a bond, include triazole and derivatives thereof. The triazole moiety is linked to the cyclic P2 scaffold and optionally substituted as shown below:

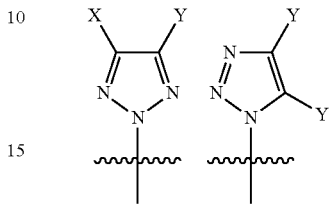

wherein X* and Y* are independently selected from the group consisting of: H, halogen, $C_1$-$C_6$alkyl, $C_0$-$C_3$carbocyclyl, —CH$_2$-amino, —CH$_2$-arylamino, —CH— diarylamino, —(C=O)-amino, —(C=O)-arylamino, —(C=O)-diarylamino, $C_0$-$C_3$aryl, $C_0$-$C_3$heterocyclyl or alternatively, X* and Y* taken together with the carbon atoms to which they are attached, form a cyclic moiety selected from the group consisting of aryl and heteroaryl.

Representative examples of substituted triazoles are as described in table 2 of WO2004/072243 and the structures following immediately after, or WO2004/113665.

Further preferred values for $R^8$ when W is a bond, include pyridazinone and derivatives thereof. The pyridazinone moiety is linked to the cyclic P2 scaffold and optionally substituted as shown below:

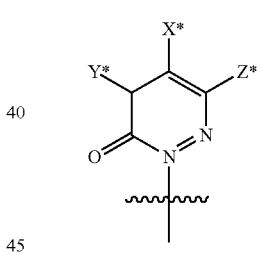

wherein X*, Y* and Z* are independently selected from the group consisting of: H, N$_3$, halogen, $C_1$-$C_6$alkyl, carbocyclyl, amino, $C_0$-$C_3$aryl, —S-aryl, —O-aryl, —NH-aryl, diarylamino, diheteroarylamino, $C_0$-$C_3$heterocycyl, —S-heteroaryl, —O-heteroaryl, NH-heteroaryl or, alternatively, X and Y or Y and Z taken together with the carbon atoms to which they are attached, form an aryl or heteroaryl cyclic moiety.

Representative examples of substituted pyridazinones are as described in table 3 of WO2004/072243 and the structures following immediately after or WO2004/113865.

Preferred P3 groups, i.e. when m is 1 resemble natural or unnatural amino adds, especially aliphatic amino adds, such as L-valyl, L-leucyl, L-isoleucyl or L-t-leucyl. Further preferred P3 groups, as shown in WO 02/01898 include $C_0$-$C_3$alkylcycloalkylalanine, especially cyclohexylalanine, optionally substituted with CO$_2$Rg, where Rg is H, is $C_1$-$C_6$alkyl, $C_0$-$C_3$alkylaryl, $C_0$-$C_3$alkylheterocyclyl, $C_0$-$C_3$alkylcycloalkyl or amine; or N-acetylpiperidine or tetrahydropyran. Preferred $R^{11}$ groups thus include $C_1$-$C_6$alkyl, $C_0$-$C_3$alkylcarbocyclyl for example $C_0$-$C_3$alkyl$C_3$-$C_7$cycloalkylyl, $C_0$-$C_3$alkylaryl or $C_0$-$C_3$alkylheteroaryl, any of which is optionally substituted with hydroxy, halo, amino, $C_1$-$C_6$alkoxy, $C_1$-$C_6$thioalkyl, C(=O)O$R^{14}$, carboxyl, ($C_1$-$C_6$alkoxy)carbonyl, aryl, heteroaryl or heterocyclyl, especially where the substituent is hydroxy or C(=O)O$R^{14}$.

Particularly preferred $R^{11}$ include tert-butyl, iso-butyl, cyclohexyl, phenylethyl, 2,2-dimethyl-propyl, cyclohexylmethyl, phenylmethyl, 2-pyridylmethyl, 4-hydroxy-phenylmethyl, or carboxylpropyl. The most preferred $R^{11}$ values are currently tert-butyl, Isobutyl, or cyclohexyl.

An embodiment of the invention include compounds wherein P4 is absent (ie n is 0) and wherein the P3 function lacks a carbonyl, ie U is absent. Representative substructures include those of formula Ii below

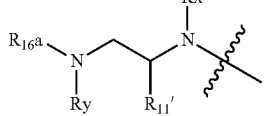

Ii wherein Rx and Ry are as defined above, preferably H, $R^{11'}$ is $C_1$-$C_6$alkyl, preferably $C_3$-$C_5$ branched alkyl such as the side chains of L-valyl, L-leucyl, L-Isoleucyl, L-t-leucyl; or $C_0$-$C_2$alkyl$C_3$-$C_7$ cycloalkyl such as cyclohexyl or cyclohexylmethyl;

$R^{16a}$ is —Rba, —S(=O)pRba, —C(=O)Rba;

Rba is $C_1$-$C_6$ alkyl, $C_0$-$C_3$alkylheterocyclyl, $C_0$-$C_3$alkylcarbocyclyl.

Alternatively, compounds of partial structure Ii may be macrocyclised between an appropriate value of $R^7$ and one of Rx, Ry or $R^{11'}$.

Representative embodiments of P3 groups which lack a carboxy function (ie variable U is absent) include those of formula VIia-VIid below:

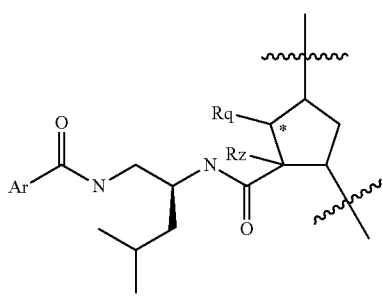

VIia

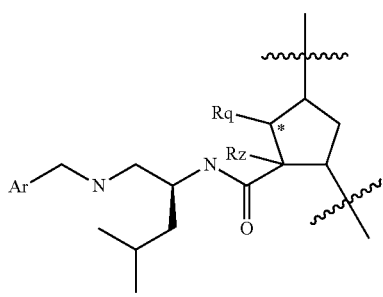

VIib

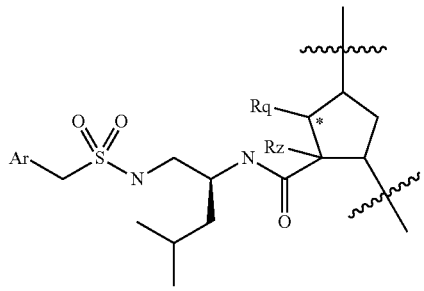

VIic

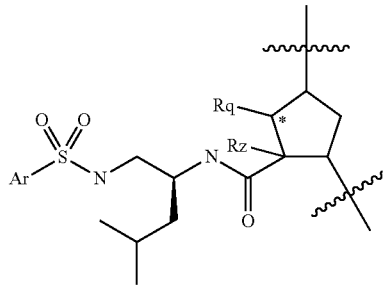

VIid where Ar is carbocyclyl or heterocycyl, especially aryl or heteroaryl, any of which is optionally substituted with $R^9$. Although the partial structures of Formulae VIia-VIid have been illustrated in the context of a compound wherein k is 1 and q' s 0, it will be apparent that such configurations of Formula VIi apply also to other values of q' and k. Similarly, although the partial structures of formulae VIic and VIid show an $R^{11'}$group corresponding to leucine, it will be apparent that these configurations will be applicable to other $R^{11}$ groups, especially those resembling the side chains of natural or unnatural L-amino acids, for example t-butyl alanine/t.leucine.

$R^{15}$ in those compounds of the invention wherein n is 1, is preferably optionally substituted $C_1$-$C_6$alkyl or $C_0$-$C_3$alkylcarbocyclyl for example $C_0$-$C_3$alkyl$C_3$-$C_7$cycloalkyl, any of which may be optionally substituted. Preferred P4 groups are typically analogues of natural or unnatural amino adds, especially aliphatic amino acids such as L-valyl, L-leucyl, L-isoleucyl, L-t-leucyl or L-cyclohexylalanine and thus favoured $R^{15}$ groups include cyclohexyl, cyclohexylmethyl, tert-butyl, iso-propyl, or iso-butyl.

Preferred G values include —NRy-, especially wherein Ry is methyl or preferably H, or hydrazine.

A further preferred G value is O thereby defining an ester with the carbonyl of P4 (if present) or the carbonyl of P3 (if present) or an ether in the case of variants wherein group U is absent. Conventional pharmaceutically acceptable ethers or esters capping groups for $R^1$ include $C_1$-$C_6$alkyl (especially methyl or t-butyl), $C_0$-$C_3$alkylheterocyclyl (especially pyridyl, benzimidazolyl, piperidyl, morpholinyl, piperazinyl) or $C_0$-$C_3$alkylcarbocyclyl (especially phenyl, benzyl, indanyl) any of which is optionally substituted with hydroxy, halo, amino, or $C_1$-$C_6$alkoxy.

Favoured compounds of the invention can comprise a hydrazine functionality, for example where T is —NRd- and m is 1; with n being zero or 1. Alternatively, especially where m is zero, G can be —NRjNRj- such as —NHNH—. Compounds will generally not comprise a hydrazine at both G and T. Preferred hydrazines within Formula VI, wherein m and n are zero include compounds of the partial structures VIja-VIjb below:

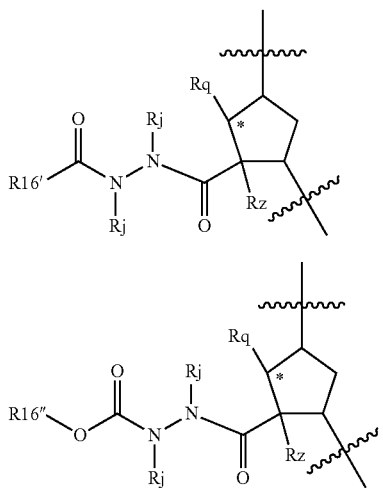

VIja

VIjb

R16 in formulae VIja and VIjb can be regarded as an alkyl (or $C_1$-$C_3$alkylheterocyclyl or $C_1$-$C_3$alkylcarbocyclyl) wherein the first alkyl carbon is substituted with an oxo group to define the keto function and R16' is the remainder of the alkyl, alkylheterocyclyl or alkylcarbocyclyl moiety. Formula VIjb depicts a variant where R16 is a methylene group whose carbon is substituted with an oxo substituent and also with —ORb, where Rb is as defined above, typically, $C_1$-$C_6$alkyl, such as t-butyl, $C_0$-$C_3$alkylheterocyclyl such as pyridyl, or $C_0$-$C_3$alkylcarbocyclyl, such as benzyl or phenyl, any of which is optionally substituted as defined above. Compounds of partial structures VIja and VIjb can be linear molecules as shown (both Rj are H), or preferably one of the depicted Rj groups can be macrocyclised via J to an appropriate $R^7$ group.

Alternative hydrazines of Formula VI where m is 1 include those of partial structures VIjc and VIjd below

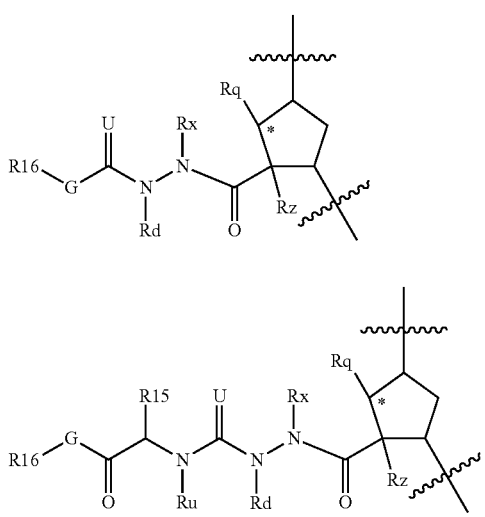

VIjc

VIjd where G, R16, R16, Rx, Rd, Rq, Rz, and Ru are as defined for formula VI above. Compounds of partial structures VIjc and VIjd can be linear molecules as shown (both Rx and Rd are H), or preferably one of the depicted Rx or Rd groups can be macrocyclised via J to an appropriate $R^7$ group.

Although formulae VIja-VIjd are depicted with a five membered carbocylic ring as P2 scaffold, it will be apparent that this aspect of the invention is equally adapted to other configurations of q' and k. Favoured embodiments within formula VIja-VIjd include those wherein Rq and Rz are H, or those wherein Rz is an olefinic bond and Rq is $C_1$-$C_3$alkyl.

Alternative hydrazine-like configuration are found when G is amino, and m and n are 0, and $R^{16}$ is an N-linked unsaturated heterocycle as defined below, for example pyridyl or pyrimidyl or a saturated heterocycle as defined below, such as piperazinyl, piperidinyl and especially morpholinyl. Examples of such embodiments include those of the formulae VIjc and VIjd:

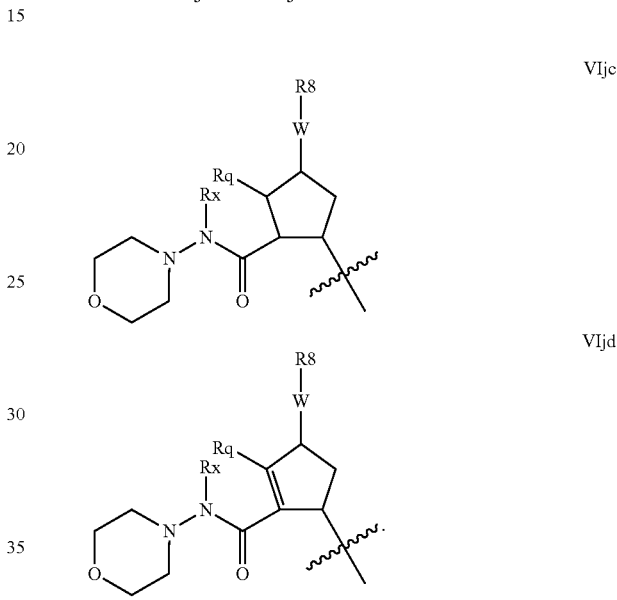

VIjc

VIjd

Compounds of partial structures VIjc and VIjd can be linear molecules as shown or preferably Rx can be macrocyclised via J to an appropriate $R^7$ group. Although these partial structures are depicted with a five membered ring as the P2 scaffold, it will be readily apparent that this configuration extends to other values of q' and k. Similarly these configurations will be applicable to other N-linked heterocycles as $R^{16}$.

Returning now to Formulae VI in general, favoured $R^{16}$ groups for the compounds of the invention include 2-indanol, indanyl, 2-hydroxy-1-phenyl-ethyl, 2-thiophenemethyl, cyclohexylmethyl, 2,3-methylenedioxybenzyl, cyclohexyl, phenyl, benzyl, 2-pyridylmethyl, cyclobutyl, iso-butyl, n-propyl, methyl, or 4-methoxyphenylethyl.

Currently preferred $R^{16}$ groups include 2-indanol, indan, 2-hydroxy-1-phenyl-ethyl, 2-thiophenemethyl, 2,3-methylenedioxybenzyl, or cyclohexylmethyl.

Unnatural amino adds include L-amino adds wherein the side chain is not one of the 20 naturally occurring amino acids. Examples of non-natural amino adds include L-beta-methylsulfonylmethylalanine, L-cyclohexylalanine, L-tertiary-leucine, L-norleucine, L-norvaline, L-ornithine, L-sarcosine, L-citurline, L-homophenylalanine, L-homoserine, L-beta-(1-napthyl)alanine, L-beta-(2-napthyl)alanine etc. Non natural amino adds also include the D-amino acids corresponding to the 20 natural amino adds and D-amino acids bearing other side chains, such as those listed above.

'$C_1$-$C_6$alkyl' (also abbreviated as $C_1$-$C_6$alk, or used in compound expressions such as $C_1$-$C_6$alkyloxy etc) as applied herein is meant to include straight and branched chain aliphatic carbon chains such as methyl, ethyl, n-propyl, isopropyl, n-butyl, isobutyl, t-butyl, pentyl, isopentyl, hexyl, heptyl and any simple isomers thereof. The alkyl group may have an unsaturated bond. Additionally, any C atom in $C_1$-$C_6$alkyl may optionally be substituted by one, two or where valency permits three halogens and/or substituted or the alkylene chain interrupted by a heteroatom S, O, NH. If the heteroatom is located at a chain terminus then it is appropriately substituted with one or 2 hydrogen atoms. $C_1$-$C_4$alkyl and $C_1$-$C_6$alkyl have the corresponding meaning to $C_1$-$C_6$alkyl adjusted as necessary for the carbon number.

'$C_1$-$C_3$alkyl' as applied herein includes methyl, ethyl, propyl, isopropyl, cyclopropyl, any of which may be optionally substituted or heteroatom interrupted as described in the paragraph above or in the case of $C_2$ or $C_3$, bear an unsaturated bond such as $CH_2$=CH.

"$C_1$-$C_3$ alkylene" as applied herein describes a divalent C1-C3alkyldiyl moiety, Including propylene, ethylene and especially methylene. The typically longer alkylene chains for J may comprise 1 to 3 unsaturations and/or interruptions with heteroatoms as defined above.

'Amino' includes $NH_2$, $NHC_1$-$C_6$alkyl or $N(C_1$-$C_6$-alkyl)$_2$, especially $C_1$-$C_3$ alkyl variants 'Amido' includes C(=O)$NH_2$ and alkylamido such as C(=O)$NHC_1$-$C_6$alkyl, C(=O)$N(C_1$-$C_6$alkyl)$_2$ especially C(=O)$NHC_1$-$C_3$alkyl, C(O)$N(C_1$-$C_3$alkyl)$_2$ or —NH(C=O)$C_1$-$C_6$alkyl, for example —NHC(=O)CH(CH$_3$)$_3$, including —NH(C=O)$C_1$-$C_3$alkyl.

'Halo' or halogen as applied herein is meant to include F, Cl, Br, I, particularly chloro and preferably fluoro.

'$C_0$-$C_3$alkylaryl' as applied herein is meant to include an aryl moiety such as a phenyl, naphthyl or phenyl fused to a $C_3$-$C_7$cycloalkyl for example indanyl, which amyl is directly bonded (i.e. $C_0$) or through an intermediate methyl, ethyl, propyl, or isopropyl group as defined for $C_1$-$C_3$alkylene above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl. "Aryl" has the corresponding meaning, i.e. where the $C_0$-$C_3$alkyl linkage is absent.

'$C_0$-$C_3$alkyl$C_3$-$C_7$cycloalkyl' as applied herein is meant to include a $C_3$-$C_7$cycloalkyl group such as cyclopropyl, cyclobutyl, cyclopentyl, cyclohexyl or cycloheptyl, which cycloakyl is directly bonded (i.e. $C_0$alkyl) or through an intermediate methyl, ethyl or proyl group as defined for $C_1$-$C_3$alkylene above. The cycloalkyl group may contain an unsaturated bond. Unless otherwise indicated the cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl.

'$C_0$-$C_3$alkylcarbocyclyl' as applied herein is meant to include $C_0$-$C_3$alkylaryl and $C_0$-$C_3$alkyl$C_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl and/or $C_0$-$C_3$alkylheterocyclyl. "Carbocyclyl" has the corresponding meaning, i.e. where the $C_0$-$C_3$alkyl linkage is absent '$C_0$-$C_3$alkylheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidyl, pyridazinyl, pyrazolyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidyl, benzopyridazinyl, benzopyrazolyl etc, which ring is bonded directly i.e. ($C_0$), or through an intermediate methyl, ethyl, propyl, or isopropyl group as defined for $C_1$-$C_3$alkylene above. Any such non-saturated rings having an aromatic character may be referred to as heteroaryl herein. Unless otherwise indicated the hetero ring and/or its fused phenyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl, $C_0$-$C_3$alkylheterocyclyl. "Heterocycly" and "Heteroaryl" have the corresponding meaning, i.e. where the $C_0$-$C_3$alkyl linkage is absent.

Typically heterocycyl and carbocyclyl moieties within the scope of the above definitions are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, Indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle moiety thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thenyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

Synthesis

Synthesis of the compounds of the present invention can be performed by different chemical strategies in solution or solid phase or a combination of both. The suitably protected individual building blocks can first be prepared and subsequently coupled together i.e. P2+P1→P2-P1. Alternatively, precursors of the building blocks can be coupled together and modified at a later stage of the synthesis of the inhibitor sequence. Further building blocks, precursors of building blocks or prefabricated bigger fragments of the desired structure, can then be coupled to the growing chain, e.g. $R^{16}$-G-P3+C(=O)—P2-P1→$R^{16}$-G-P3-C(=O)—P2-P1 or $R^{16}$-G-P4-P3+C(=O)—P2-P1→R1-G-P4-P3-C(=O)—P2-P1.

Coupling between two amino acids, an amino acid and a peptide, or two peptide fragments can be carried out using standard coupling procedures such as the azide method, mixed carbonic-carboxylic acid anhydride (Isobutyl chloroformate) method, carbodiimide (dicyclohexylcarbodiimide, diisopropylcarbodiimide, or water-soluble carbodiimide) method, active ester (pnitrophenyl ester, N-hydroxysuccinic imido ester) method, Woodward reagent K-method, carbonyldiimidazole method, phosphorus reagents or oxidation-reduction methods. Some of these methods (especially the carbodimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[(3dimethylamino) propyl] carbodiimide. A practical and useful coupling agent is the commercially available (benzotriazol-1-yloxy) tris-(dimethylamino) phosphonium hexafluorophosphate, either by itself or in the present of 1-hydroxybenzotriazole or 4-DMAP. Another practical and useful coupling agent is commercially available 2-(1H-benzotriazol-1-yl)-N, N, N',N'-tetramethyluronium tetrafluoroborate. Still another practical and useful coupling agent is commercially available 0-(7-azabenzotrizol-1-yl)-N, N,N', N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

The α-carboxyl group of the C-terminal residue is usually protected as an ester that can be cleaved to give the carboxylic acid. Protecting groups that can be used include 1) alkyl esters such as methyl, trimethylsilyl and t.butyl, 2) aralkyl esters such as benzyl and substituted benzyl, or 3) esters that can be cleaved by mild base or mild reductive means such as trichloroethyl and phenacyl esters.

The α-amino group of each amino acid to be coupled is typically protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl 5) alkyl groups such as triphenylmethyl and benzyl; 6) trialkylsilyl such as trimethylsilyl; and 7) thiol containing groups such asphenylthiocarbonyl anddithiasuccinoyl. The preferred α-amino protecting group is either Boc or Fmoc. Many amino acid derivatives suitably protected for peptide synthesis are commercially available.

The α-amino protecting group is cleaved prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Any of the natural or non-natural amino acids having side chain functionalities will typically be protected during the preparation of the peptide using any of the above described groups. Those skilled in the art will appreciate that the selection and use of appropriate protecting groups for these side chain functionalities depend upon the amino acid and presence of other protecting groups in the peptide. In the selection of such protecting groups it is desirable that the group is not removed during the deprotection and coupling of the α-amino group.

For example, when Boc is used as the α-amino protecting group, the following side chain protecting groups are suitable: p-toluenesulfonyl (tosyl) moieties can be used to protect the amino side chain of amino acids such as Lys and Arg; acetamidomethyl, benzyl (Bn), or tert-butylsulfonyl moities can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert. butyl based protecting groups are acceptable. For instance, Boc can be used for lysine and arginine, tert.butyl ether for seine, threonine and hydroxyproline, and tert-butyl ester for aspartic acid and glutamic acid. Triphenylmethyl (Trityl) moiety can be used to protect the sulfide containing side chain of cysteine.

Once the inhibitor sequence is completed any protecting groups are removed in whatever manner is dictated by the choice of protecting groups. These procedures are well known to those sidled in the art.

Introduction of the P2 Substituent

The $R^8$ group can be coupled to the P2 scaffold at any convenient stage of the synthesis of compounds according to the present invention. One approach is to first couple the $R^8$ group to the P2 scaffold and subsequently add the other desired building blocks, i.e. P1 and optionally P3 and P4.

Another approach is to couple the P1, P2 and if present P3 and P4 moieties using an unsubstituted P2 scaffold and add the R⁸ group afterwards.

Compounds wherein W is O and R⁸ is alkyl, C₀-C₃alkylcarbocycylyl, C₀-C₃alkylheterocycylyl can be prepared according to the procedure described by E. M. Smith et al. (J. Med. Chem. (1988), 31, 875-885), as depicted in Scheme 1, which illustrates the technique with a saturated P2 scaffold wherein q' is 0 and k is 1.

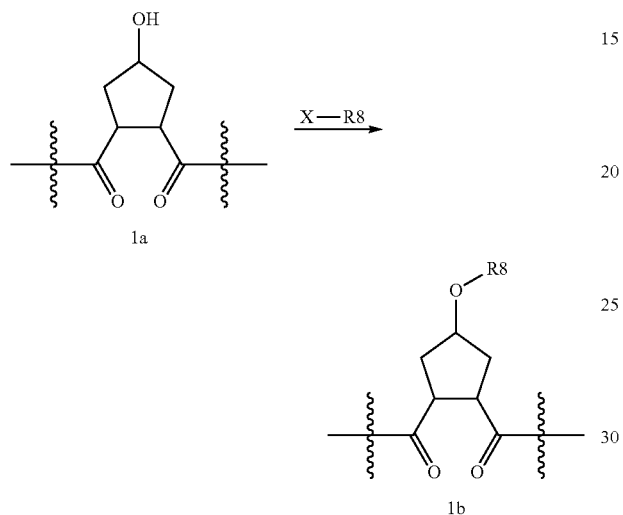

Treatment of a compound containing an unsubstituted P2 scaffold (1a), which ca be prepared as described herein below with a base such as sodium hydride or potassium t.butoxide in a solvent like dimethylformamide followed by reaction of the resulting alkoxide with an alkylating agent, R⁸—X, wherein X is a suitable leaving group such as a halide, mesylate, triflate or tosylate, provides the desired substituted derivative (1b).

Alternatively, if X is OH or SH, the P2 substituent can be introduced via a Mitsunobu reaction by reacting the hydroxy group of compound 1a with the desired alcohol or thiol in the presence of triphenylphosphine and an activating agent like diethyl azodicarboxylate (DEAD), diisopropyl azodicarboxylate (DIAD) or the like. (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706).

Alcohol (1a) can alternatively be treated with phosgene thus providing the corresponding chloroformate which upon reaction with an amine, R⁸NH₂, in the presence of a base like sodium hydrogen carbonate or triethylamine, provides carbamates i.e. W is —OC(=O)NH—, whereas reaction of alcohol (1a) with an acylating agent, R⁸—CO—X, like an acid anhydride or add halide for instance the acid chloride, to provide esters, i.e. W is —OC(=O)—.

Various alcohols R⁸—OH, and alkylating agents R⁸—X are described in WO 00/09543 and WO00/59929. An example of the synthesis wherein R⁸ is a substituted quinoline derivative is shown in Scheme 2.

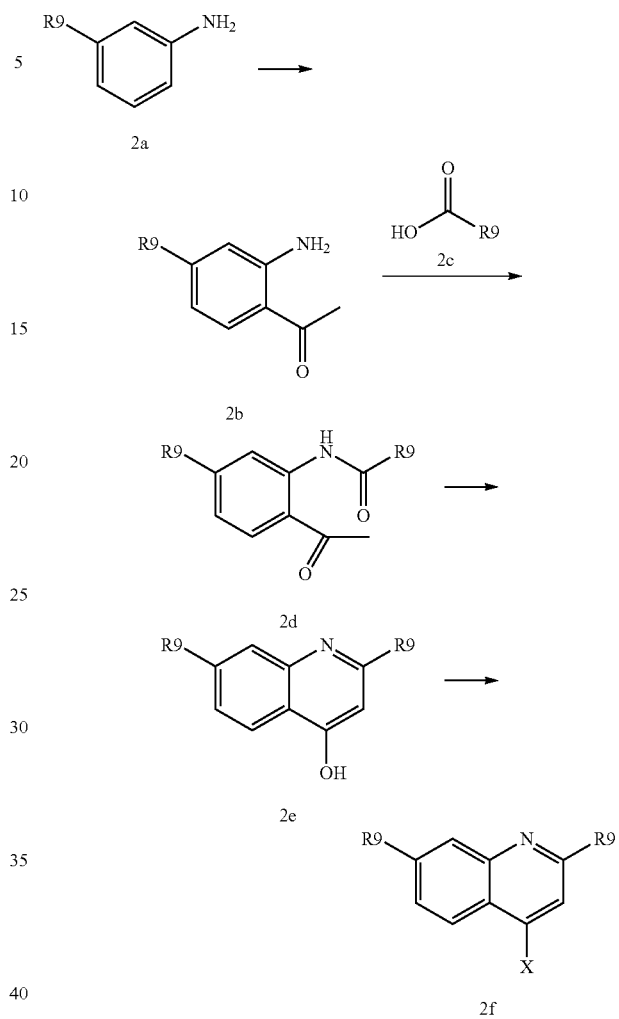

Friedel-Craft acylation of a suitable substituted aniline (2a), available either commercially or in the literature, using an acylating agent like acetyl chloride or the like in the presence of boron trichloride and aluminium trichloride in a solvent lice dichloromethane provides (2b). Coupling of (2b) to a heterocyclic carboxylic add (2c) under basic conditions, such as in pyridine, in the presence of an activating agent for the carboxylate group, for instance POCl₃, followed by ring closure and dehydration under basic conditions like potassium tert-butoxide in tert-butanol provides quinoline derivative (2e). Quinoline derivative (2e) can be coupled in a Mitsunobu reaction to an alcohol as described above, or the hydroxy group can be displaced by a suitable leaving group such as a halide like chloride, bromide or iodide, by treatment of quinoline (2e) with an appropriate halogenating agent for example phosphoryl chloride or the like.

A variety of carboxylic adds with the general structure (2c) can be used in Scheme 2. These adds are available either commercially or in the literature. An example of the preparation of 2-(substituted)-amino-carboxy-aminothiazole derivatives, following the procedure by Berdikhina et al. Chem. Heterocycl. Compd. (Eng. Transl.) (1991), 427-433, is shown in scheme 3 below.

Scheme 3

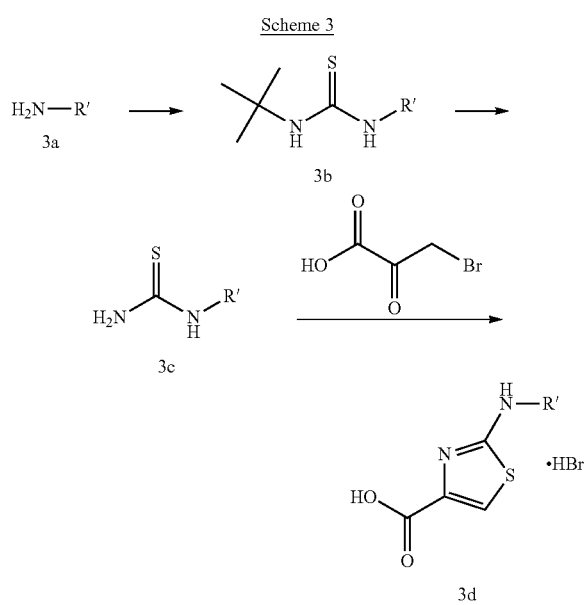

Thiourea (3c) with different alkyl substituents R' can be formed by reaction of the appropriate amine (3a) with tert-butylisothiocyanate in the presence of a base like diisopropylethylamine in a solvent like dichloromethane followed by removal of the tert-butyl group under acidic conditions. Subsequent condensation of thiourea derivative (3c) with 3-bromopyruvic acid provides the add (3d).

P2 building blocks wherein the $R^8$ substituent is attached via an amine, amide, urea or sulphonamide, can be prepared from amino substituted carbocycles achieved for example by transforming the hydroxy group of the corresponding hydroxy derivative into an azide group for example by transforming the hydroxy group into a suitable leaving group such as a mesylate or halogen like chloride, followed by substitution of the leaving group with azide or by the use of an azide transfer agent like diphenylphosphoryl azide (DPPA). Reduction of the azide by catalytic hydrogenation or any other suitable reduction method provides the amine. The amino derivative can be reacted in a displacement reaction with an alkylating agent of the general formula $R^8$—X wherein $R^8$ and X are as described for scheme 1, to form P2 building blocks for use in the preparation of compounds of general formula VI, wherein W is —NH—. Reaction of the amino substituted carbocycle with an acid of the general formula $R^8$—COOH under standard amide coupling conditions provides compounds wherein the $R^8$ substituent is linked via an amide bond, whereas reaction of the amino substituted carbocycle with an appropriate derivative of sulphonic acid, $R^8$—S(O)$_2$—X where X is a leaving group for example chloride, in the presence of a base, provides sulphonamides. Compounds wherein the linkage between the cyclic scaffold and the $R^8$ substituent is constituted of a urea group can for example be achieved by treatment of amino substituted carbocycle with phosgene to afford the corresponding chlorocarbamate followed by reaction with the desired amine. Alternatively, the amino substituted carbocycle can be reacted with the carbamoyl chloride or isocyanate of the desired $R^8$ substituent for the formation of the urea linkage. It will be apparent that corresponding reactions will be available for P2 groups with other ring sizes and substitution pattern.

Compounds wherein a heterocyclic $R^8$ group is attached directly to the cyclic P2 scaffold i.e. W is a bond in general formula VI, can be prepared for example by using a replacement reaction wherein a suitable leaving group such as halide a or a mesylate or the like on the P2 scaffold is replaced by the desired $R^8$ group such as a heterocyclic group. Alternatively the $R^e$ group can be introduced by way of a Mitsunobu reaction wherein the hydroxy group of the P2 precursor is reacted with a nitrogen atom in the heterocyclic $R^8$ group.

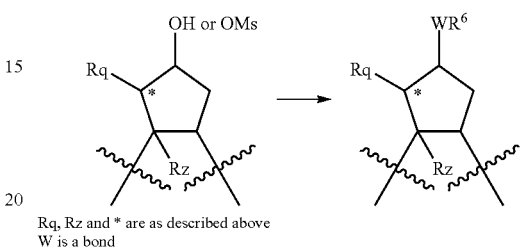

Rq, Rz and * are as described above
W is a bond

Compounds wherein a tetrazole derivative is attached to one of its ring carbons are conveniently prepared by building up the tetrazole moiety directly on the P2 precursor. This can be achieved for instance by transforming the hydroxy group of the P2 precursor into a cyano group followed by reaction with an azide reagent like sodium azide. Triazole derivatives can also be built up directly on the P2 precursor for example by transforming the hydroxy group of the P2 precursor into an azide group followed by a 3+2 cycloaddition reaction of the afforded azide and a suitable alkyne derivative.

Structurally diverse tetrazoles for use in the above described substitution or Mitsunobu reactions can be prepared by reacting commercially available nitrile compounds with sodium azide. Triazole derivatives can be prepared by reaction of an alkyne compound and trimethylsilyl azide. Useful alkyne compounds are available either commercially or they can be prepared for instance according to the Sonogashira reaction i.e. reaction of a primary alkyne, an aryl halide and triethylamine in the presence of PdCl$_2$(PPh)$_3$ and CuI as described for example in A. Elangovan, Y.-H. Wang, T.-I. Ho, Org. Let., 2003, 5, 1841-1844. The heterocyclic substituent can also be modified when attached to the P2 building block either before or after coupling of the P2 building block to the other building blocks.

These methods and further alternatives for the preparation of compounds wherein W is a bond and $R^8$ is an optionally substituted heterocycle are extensively described in WO2004/072243.

Compounds having an alternative ring size and/or position of the W—$R^8$ substituent of the carbocyclic derivative in scheme 1 may also be used in the preparation of compounds according to the present invention.

Synthesis and Introduction of P1 Building Blocks.

The amino acids used in the preparation of P1 fragments are available either commercially or in the literature, see for example WO 00/09543 and WO00/59929 from Boehringer-Ingelhelm or US2004/0048802 from BMS.

Scheme 4 shows an example of the preparation of a sulphonamide derivative to be used as a P1 building block, and the subsequent coupling to a P2 building block.

Scheme 6

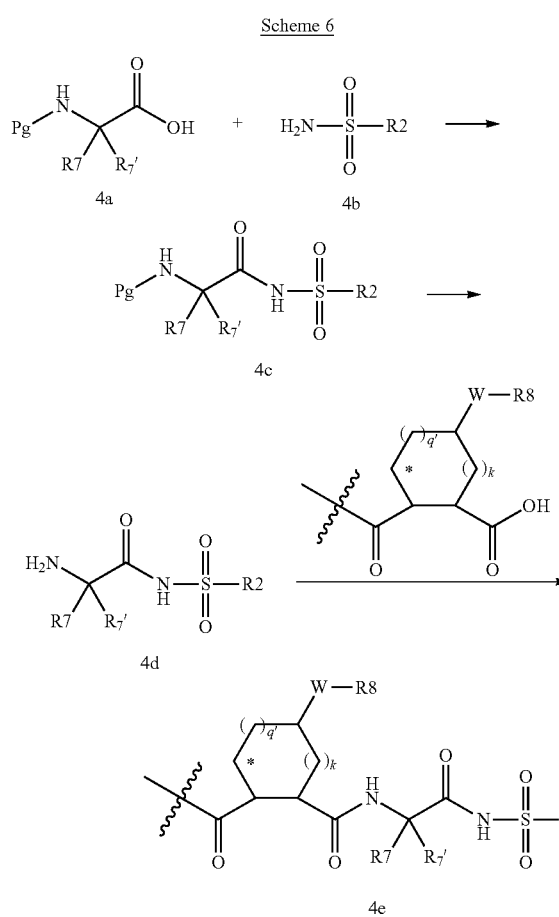

The sulphonamide group can be introduced on a suitably protected amino acid (4a) by treatment of the amino acid with a coupling agent, for example N,N'-carbonyldiimidazole (CDI) or the like, in a solvent like THF followed by reaction with the desired sulphonamide (6b) in the presence of a strong base such as 1,8-diazabicyclo[5.4.0]undec-7-ene (DBU). Alternatively the amino acid can be treated with the desired sulphonamide (4b) in the presence of a base like diisopropyl ethylamine followed by treatment with a coupling agent like PyBOP® to effect the introduction of the sulphonamide group. Removal of the amino protecting group by standard methods and subsequent coupling to a P2 building block, prepared as described below, using standard methods for amide bond formation, like using a coupling agent such as O-(7-azabenzotriazol-1-yl)-N,N,N',N'-tetramethyluronium hexafluorophosphate (HATU) in the presence of a base such as diisopropylamine in a solvent like dimethylformamide, gives 4e. Alternatively, the sulphonamide group can be introduced at a later stage of the synthesis, for example as the last step. In this case an amino acid with the reversed protection pattern, i.e. with an unprotected amino function and protected acid function, is coupled the acid function of the P2 building block using standard peptide coupling conditions for example as described above. Removal of the acid protection group, using the appropriate conditions for the present protection group, followed by coupling of the sulphonamide as described above then yields compound 4e.

P1 building blocks for the preparation of compounds according to general formula VI wherein A is an ester or an amide can be prepared by reacting amino acid (4a) with the appropriate amine or alcohol respectively under standard conditions for amide or ester formation. Compounds according to general formula I wherein A is $CR^4R^{4'}$ can be prepared by coupling of the appropriate P1 building block to the P2 building block as described in Oscarsson et al Bioorg Med Chem 2003 11(13) 2955-2963 and PCT/EP03/10595 filed 23 Sep. 2003, the contents of which are incorporated by reference.

Compounds comprising an azapeptide P1 residue, i.e. M is NRu in general formula VI can be prepared by using a suitable P1 aza-amino acyl moiety in the coupling to the P2 fragment. The preparation of aza-amino acyl moieties is described by M. D. Bailey at al. In J. Med. Chem., 47, (2004), 3788-3799, and an example is shown in scheme 5.

Scheme 5

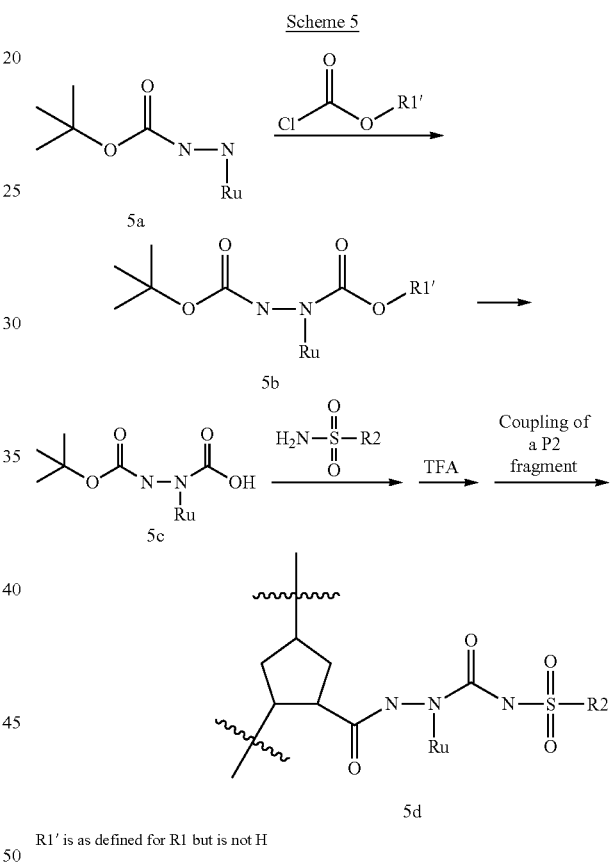

R1' is as defined for R1 but is not H

Incorporation of the appropriate N-linked side chain, Ru, on commercially available tert-butylhydrazine can be performed for example by a reductive amination reaction with the appropriate aldehyde or ketone as described in scheme 19 below which produces the N-alkylated carbazate (5a). Condensation of 5a with a desired chloroformate in the presence of a base like triethylamine or diisopropylethylamine in a solvent like THF provides 5b. The R1' moiety can then optionally be removed using the appropriate conditions depending on the specific R1', such as catalytic hydrogenation for R1' being benzyl, which gives the corresponding acids. Subsequent reaction of the afforded acid with a desired sulphonamide derivative as described in scheme 4 yields sulphonamide capped building blocks. Alternatively, reaction of carbazate 5a with an isocyanate, R3-N=C=O, provides building blocks for the preparation of compounds according to general formula VI wherein M is NRu and A is CONHR³.

Synthesis of Capped P3 and P4-P3 Building Blocks

The building blocks R¹⁶-G-P3 and R¹⁶-G-P4-P3 can be prepared as generally depicted in scheme 6.

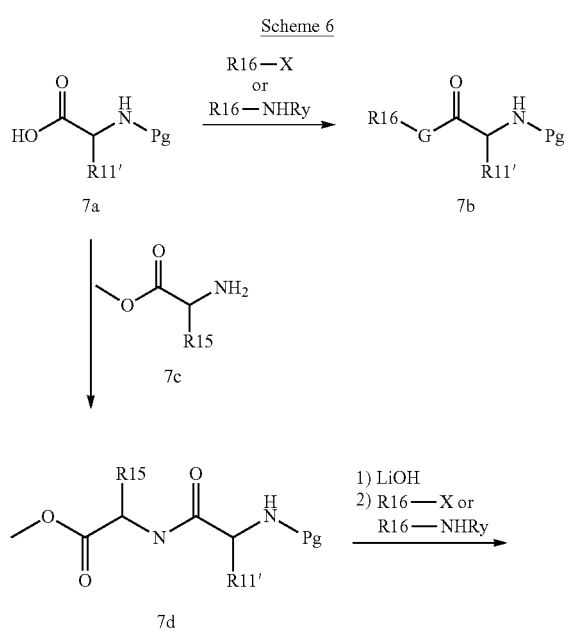

R11' has the same definition as R11 but is not part of a macrocycle

A suitable N-protected amino acid (6a) can be coupled with an amino capping group (R¹⁶—NHRy) using standard peptide coupling conditions like with coupling agents such as HATU, DCC, HOBt or the like in the presence of a base such as DIEA or DMAP in a solvent like dichloromethane, chloroform or dimethylformamide or a mixture thereof and ester formation conditions like providing amides i.e. G is NHRy (6b). Alternatively, reaction of amino acid (6a) with a compound of general formula R¹⁶—X where R¹⁶ is as defined above and X is a leaving group such as a halide, in the presence of a base like cesium carbonate or silver (I) oxide provides esters, i.e. G is O (6b). On the other hand, amino acid (6a) can be coupled to a second, suitably O-protected, amino acid (6d) using standard peptide coupling conditions as described above, providing (6e). Displacement of the ester group with a suitable capping group (6b) provides fragment (6f) useful for the preparation of compounds according to the present invention wherein m and n are 1.

When G is N-Ry, the capped P3 or P2 building block can also be prepared on solid support as exemplified in Scheme 7.

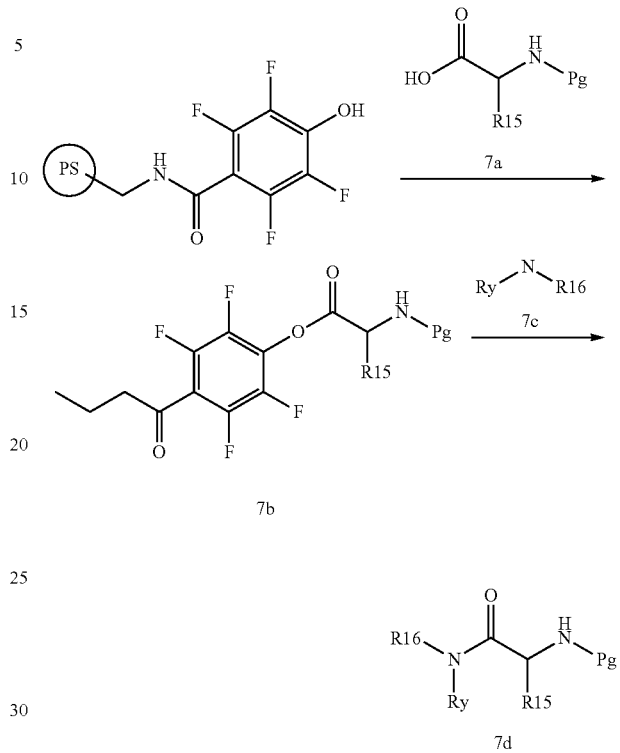

An appropriate N-protected, for example Boc protected, amino acid (7a) can be immobilized on a solid support, here exemplified by Agronaut resin PS-TFP, by reacting the amino acid with the desired solid support in the presence of coupling reagent like N,N'-diisopropylcarbodiimide and a base like DMAP in a solvent like dichloromethane and dimethylformamide. The immobilized amino acid (7b) can then be cleaved from the support with a suitable capping group (7c) thus giving fragments (7d) useful for the preparation of compounds according to the present invention wherein m or n is 1. Optionally the amino protecting group can be removed followed by coupling of an appropriate amino acid using standard methods thus providing fragments useful for the preparation of compounds according to the present invention wherein m and n are 1.

Preparation and Incorporation of P2 Building Blocks

A typical route to compounds containing a 5 membered saturated P2 scaffold is shown in Scheme 8.

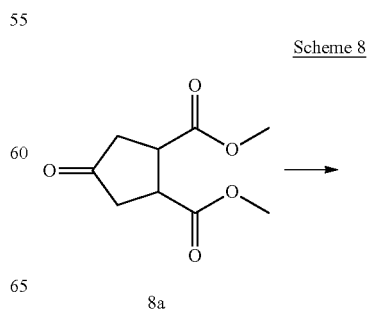

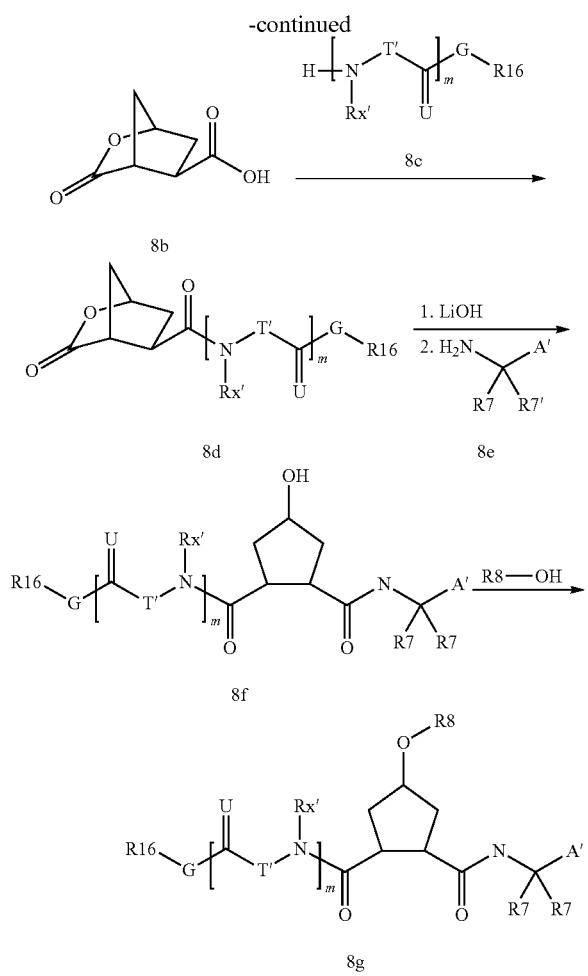

Rx' and T' have the same definitions as Rx and T respectively but are not part of a macrocycle. A' is a protected carboxylic acid, substituted amide or sulphone amide or CR4R4'.

The cyclic scaffold (8b) can be prepared, for example, from 3,4-bis(methoxycarbonyl)cyclopentanone (8a), as described by Rosenquist et al. in Acts Chem. Scand. 46 (1992) 1127-1129 by reduction of the keto group with a reduction agent like sodium borohydride in a solvent like methanol followed by hydrolysis of the esters and finally ring closure in acetic anhydride in the presence of pyridine. The provided bicyclic acid (8b) can then be coupled to the amine function of the desired P3 fragment (8c), P3-P4 fragment or capping group $R^{16}$—NHRy, using conventional peptide coupling conditions like with HATU and diisopropyl amine in a solvent like dimethyl formamide, giving (8d). Lactone opening of (8d) with for example lithium hydroxide provides the acid which subsequently can be coupled to the amino group of a P1 building block or a precursor of a desired P1 fragment (8e), using conventional peptide coupling conditions. The $R^8$-substituent of the carbocycle can be introduced for example by a Mitsunobu reaction with the appropriate alcohol as described above or by any other suitable method previously described. When $R^7$, $R^{7'}$ and A' contains functional groups, these are optionally suitably protected by methods recognized by persons sidled in the art, se for example Bodanzky or Greene cited above.

Scheme 9 shows an alternative route towards compounds of formula VI containing a saturated P2 scaffold, where the building blocks are introduced in the reversed order, i.e. the P1 fragment is introduced before the capping group, P3 or P3-P4 building block.

Scheme 9

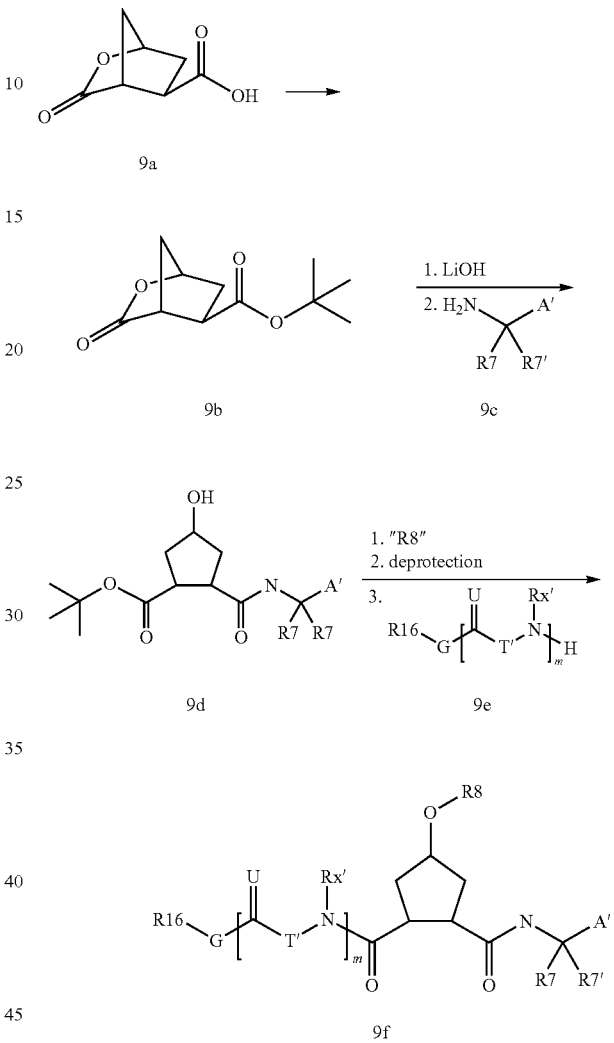

Rx' and T' have the same definitions as Rx and T respectively but are not part of a macrocycle. A' is a protected carboxylic acid, substituted amide or sulphone amide or CR4R4'.

Protection of the add group of (9a) for example as the tert-butyl ester by treatment with dl-tert-butyl dicarbonate in the presence of a base like dimethylaminopyridine and triethylamine in a solvent like dichloromethane provides ester (9b). Lactone opening and coupling of a P1 building block (9c) as described in scheme 13 or directly by the amine group of the P1 fragment provides (9d). Introduction of $R^8$-substituent as described above followed by removal of the acid protection group by subjecting the ester to acidic conditions like trifluoroacetic acid and triethylsilane in a solvent like methylene chloride and finally coupling of the P3 building block (9e), P3-P4 building block or capping group $R^{16}$—NHRy, as described above provides (9f). When $R^7$, $R^{7'}$ and A' contain functional groups, these are optionally suitably protected by methods recognized by persons skilled in the art, see for example Bodanzky or Greene cited above.

An unsaturated P2 scaffold to be used in the preparation of compounds of formula VI can be prepared as illustrated with cyclopentene below.

The cyclopentene scaffold is typically prepared as described in scheme 10.

Scheme 10

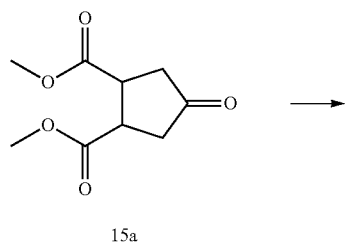

15a

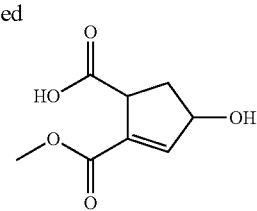

15c

A bromination-elimination reaction of 3,4-bis(methoxycarbonyl)cyclopentanone (10a) as described by Dolby et al. in J. Org. Chem. 36 (1971) 1277-1285 followed by reduction of the keto functionality with a reduction agent like sodium borohydride provides the unsaturated hydroxy compound (10b). Selective ester hydrolysis using for example lithium hydroxide in a solvent like a mixture of dioxane and water provides hydroxy substituted monoester derivative (10c).

An unsaturated P2 building scaffold wherein Rq is other than hydrogen, such as a methylated cyclopentene scaffold can be prepared as shown in scheme 11.

Scheme 11

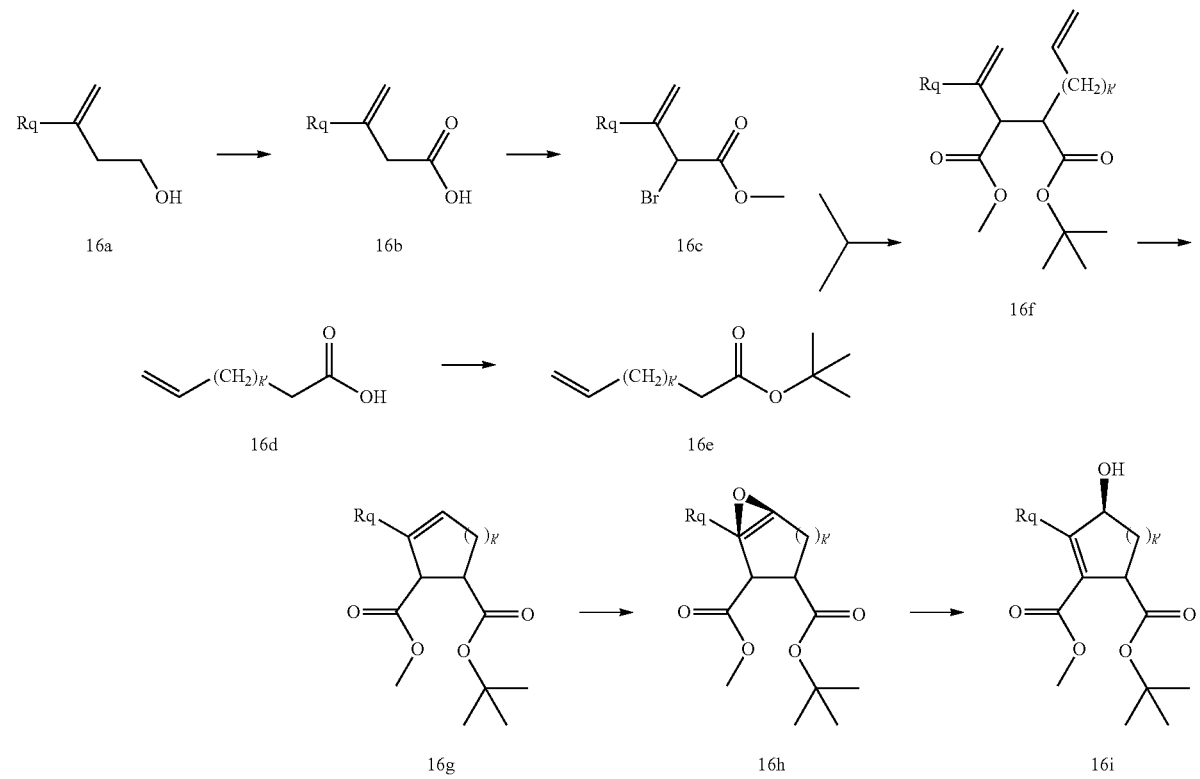

-continued

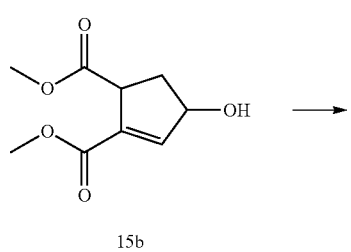

15b

Oxidation of commercially available 3-methyl-3-buten-1-ol (11a) by the use of an oxidation agent like pyridinium chlorochromate followed by treatment with acetyl chloride, bromine and methanol provides the α-bromo eater (11c). The afforded ester (11c) can then be reacted with the enolate (11e), achieved for example by treatment of the corresponding tert-butyl ester with a base such as lithium diisopropyl amide in a solvent like tetrahydrofuran, to give the alkylated compound (11f). The tert-butyl ester (11e) can be prepared by treatment of the corresponding commercially available acid (11d) where k' is 1 to 3 with di-tert-butyl dicarbonate in the presence of a base like dimethylaminopyridine. Cyclisation of (11f) by an olefin metathesis reaction performed as described above provides cyclopentene derivative (11g).

Stereoselective epoxidation of (11g) can be carried out using the Jacobsen asymmetric epoxidation method to furnish the epoxide (11h). Finally, addition of a base like DBN (1,5-diazabicyclo-[4.3.0]non-5-ene) yields the alcohol (11i). Optionally the double bond of compound (11i) can be reduced for example by catalytic hydrogenation using a catalyst like palladium on carbon which provides the corresponding saturated compound.

The afforded cyclic scaffolds can then be used, as described above, to complete the inhibitor sequence. An example is shown in scheme 12.

Scheme 12

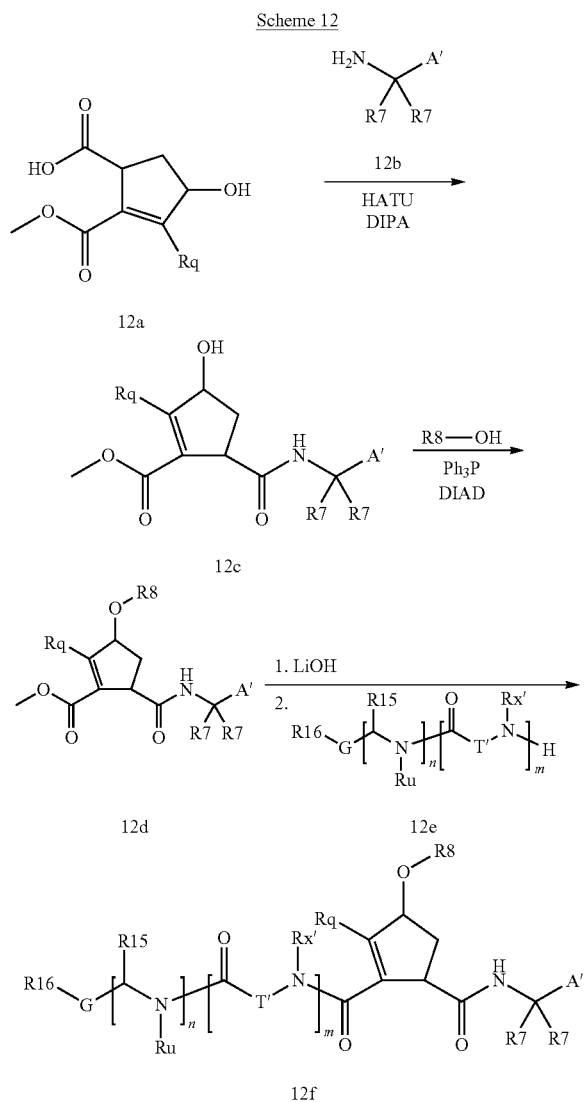

Rx' and T' have the same definitions as Rx and T respectively but are not part of a macrocycle. A' is a protected carboxylic acid, substituted amide or sulphone amide or CR4R4'.

The amino group of a P1-building block or a suitable precursor thereof (12b) can be coupled to the acid of the cyclopentene derivative (12a) using standard amide coupling conditions such as using HATU in the presence of a base like diisopropyl phenylamine or the like, followed by introduction of the $R^8$-substituent for example by Mitsunobu conditions as described above to provide (12d). Hydrolysis of the remaining ester and subsequent amide coupling of a desired P3 or P3-P4 building block (12e) optionally followed by manipulations of the P1 part provides cyclopentene containing compounds (12f) according to general formula VI. When $R^7$, $R^{7'}$ and A' contain functional groups, these are optionally suitably protected by methods recognized by persons sidled in the art, see for example Bodanzky or Greene cited above.

Compounds having a hydrazine containing capping group attached directly to the P2 moiety, i.e. P3 and P4 are absent and G is NRjNRj, can be prepared as depicted in Scheme 13

Scheme 13

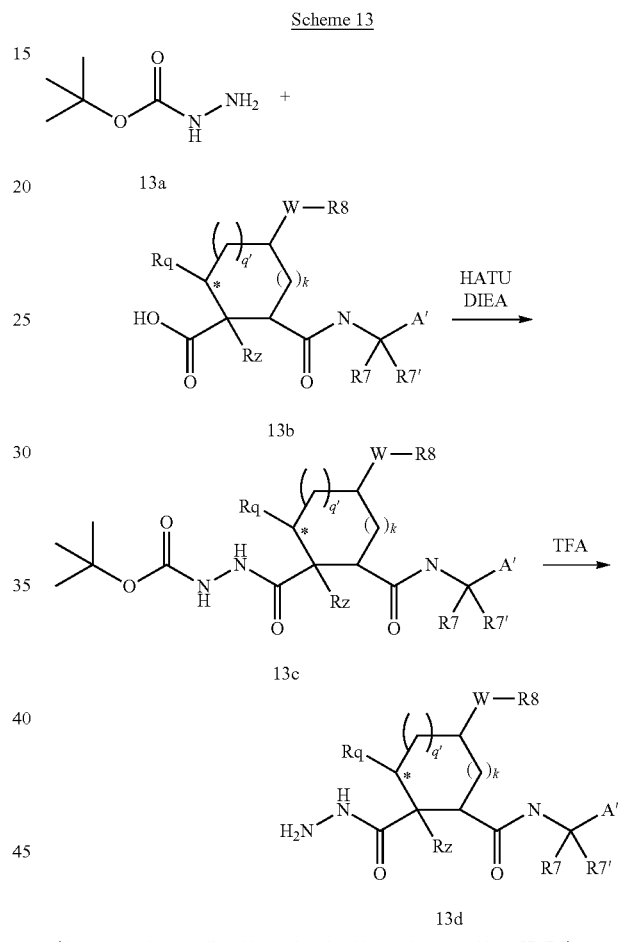

A' is a protected carboxylic acid, substituted amide or sulphone amide or CR4R4'

Reaction of tert-butyl carbazate (13a), optionally alkyl substituted on one or both nitrogens, with the add (13b) under peptide coupling conditions like with HATU and DIEA in a solvent like DMF provides 9Ac. Optional removal of the boc group by standard procedures like acidic treatment with for example TFA in a suitable solvent such as dichloromethane, provides the hydrazine containing derivative (13d). Alternatively, any appropriate hydrazine derivative, such as morpholin-1-ylamine, piperidin-1-ylamine or the like can be linked to the acid (13b) instead of the tert-butyl carbazate derivative.

The achieved compound can then be further extended by coupling of a P3 or P4-P3 building block to the primary amine of compound 13d for example ms shown in scheme 14.

Scheme 14

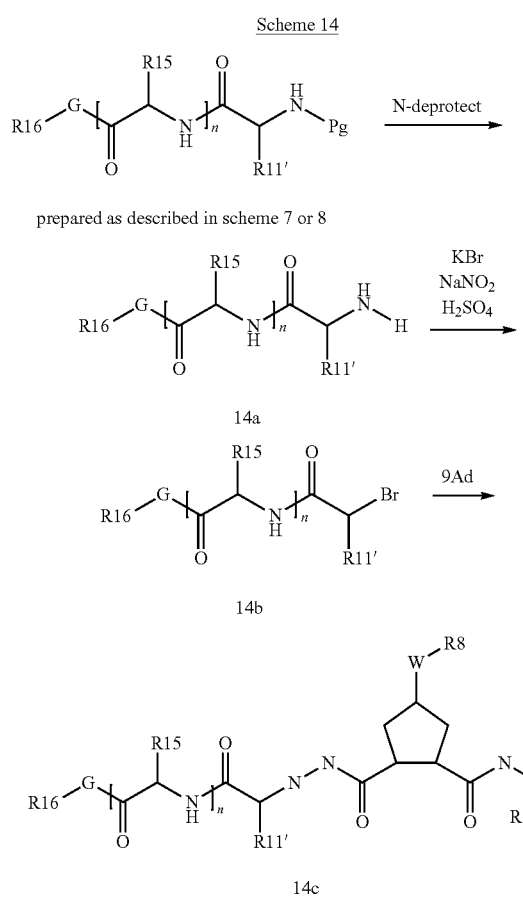

R11' has the same definition as R11 but are not part of a macrocycle. A' is a protected carboxylic acid, substituted amide or sulphone amide or CR4R4'.

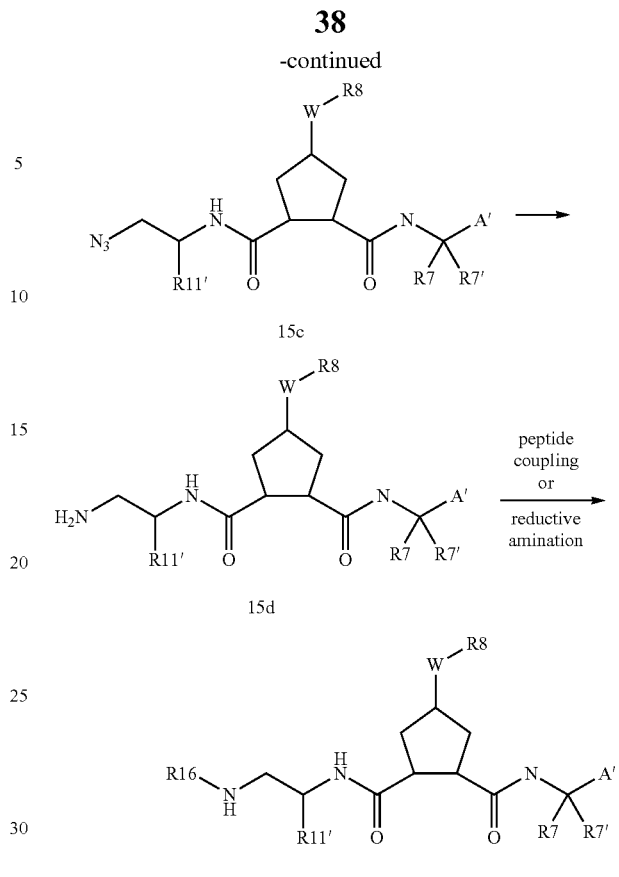

R11' has the same definition as R11 but are not part of a macrocycle. A' is a protected carboxylic acid, substituted amide or sulphone amide or CR4R4'.

Treatment of the α-amino compound (14a) with sodium nitrite, potassium bromide and sulphuric acid (Yang et al. J. Org. Chem. (2001), 66, 7303-7312) provides the corresponding α-bromo compound (14b) which upon reaction with the above described derivative (13d) provides the hydrazine containing derivative (14c).

Compounds lacking a carboxy group in the P3 unit can be prepared as illustrated in Scheme 15 exemplified with a cyclopentane derivative as P2 scaffold.

The acid (15a) can be coupled to an amino azide derivative (15b), prepared by methods known from the literature using standard peptide coupling conditions to give the amide derivative (15c). Reduction of the azide function for example by polymer bound triphenyl phosphine in a solvent like methanol or any other suitable reduction method provides intermediate (15d) which subsequently can be reacted with an acid under peptide coupling conditions or with an amine in a reductive amination reaction providing amides and secondary amines respectively.

Scheme 16 shows an alternative route towards compounds lacking a carboxy group in the P3 unit

Scheme 15

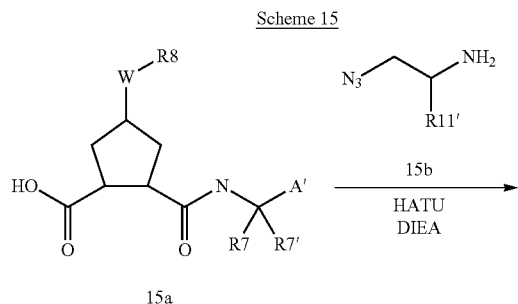

Scheme 16

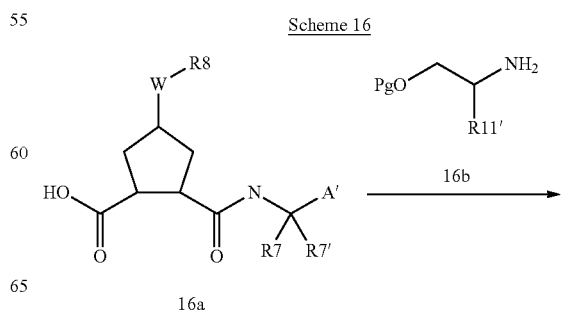

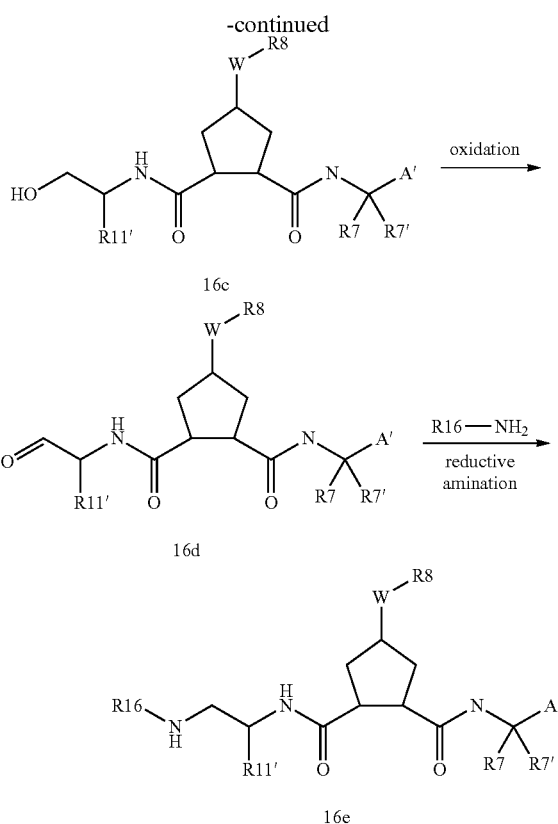

R11' has the same definition as R11 but is not part of a macrocycle. A' is a protected carboxylic acid, substituted amide or sulphone amide or CR4R4'.

Instead of using the azide derivative (15b) in scheme 15 the corresponding, optionally protected, hydroxy derivative (16b) can be used in the coupling with the acid (16a) and thus introducing a primary alcohol. The alcohol (16c) can then, after optional deprotection, be oxidized with a suitable oxidizing agent like for example Dess-Martin periodinane to form the corresponding aldehyde. Reaction of the aldehyde with a desired amine in a reductive amination reaction using a reagent like for example polystyrene bound cyanoborohydride in a solvent like THF provides amine derivatives (16e).

Alternatively alcohol (16c) can be reacted with a suitable acylating or alkylating agent under the appropriate conditions to provide ester and ether compounds respectively, i.e. G is O in general formula VI.

Subsequent reaction of the formed alcohol with a suitable acylating or alkylating agent using the appropriate conditions provides the ester and ether compounds respectively, i.e. G is O in general formula VI.

Although Scheme 15 and 16 have been described with reference to a cyclopentane derivative i.e. q' is 0 and k is 1 in Formula VI, it will be readily apparent that the corresponding methodology is applicable for other compounds of the Formula VI.

When $R^7$, $R^{7'}$ and A' contains functional groups, these are suitably protected by methods recognized by persons skilled in the art, see for example Bodanzky or Greene cited above.

Formation of Macrocyclic Compounds

Compounds according to the present invention wherein an alkylene chain extending from the $R^7/R^{7'}$ cycloalkyl to Rx, Rd or $R^{11}$ thus forming a macrocycle, can be prepared as described below. Suitable P1, P2 and P3 building blocks, or precursors thereof, are coupled together using the strategies described above, followed by a ring-closing reaction (macrocyclization). The substituent W—$R^8$ of the P2 building block can be incorporated via a Mitsunobu reaction as described above, before or after formation of the macrocycle or the assembly can be done with the required substituted proline analogue or carbocycle. For macrocyclic structures extending from the $R^7/R^{7'}$ cycloalkyl to $R^{11}$, P3 amino acids containing the appropriate side chain can be prepared as described in WO00/59929.

A typical route to macrocyclic compounds is shown in Scheme 17 which illustrates the technique applied to a compound having a spiro-cyclopropyl P1, where the macrocycle incorporates the P3 side chain.

Scheme 17

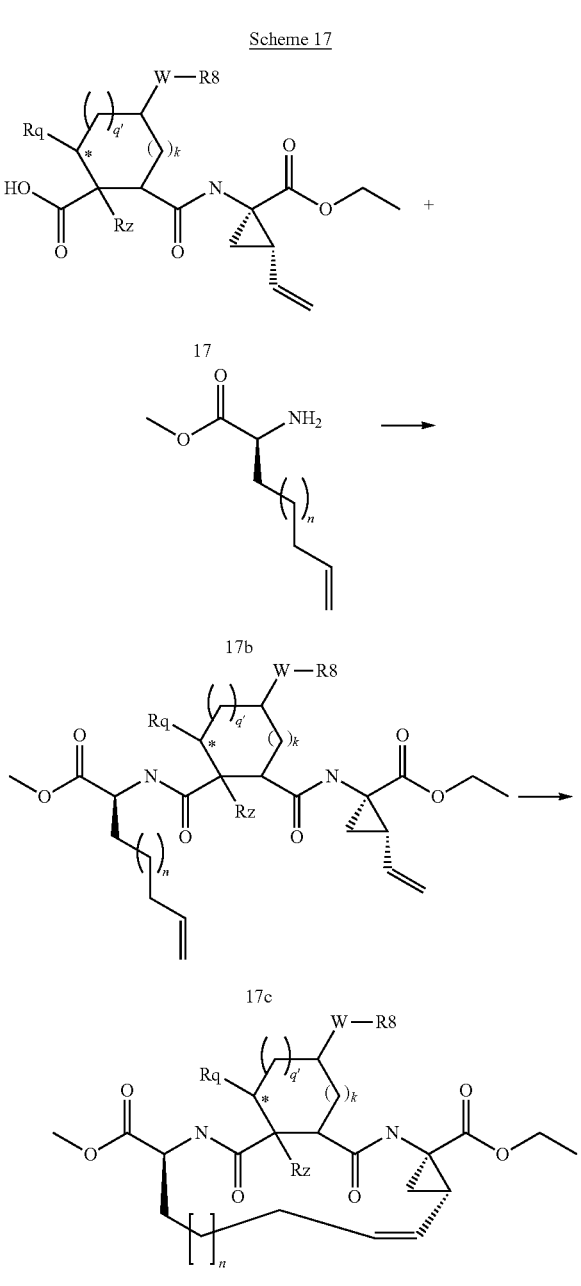

n = 1, 2, 3, 4, 5, 6, 7

Coupling of acid derivative (17a) with the appropriate, acid protected, amino acid (17b) using standard peptide coupling conditions as described above provides (17c). Formation of the macrocycle can then be carried out via an olefin metathesis reaction using a Ru-based catalyst such as the one reported by Miler, S. J., Blackwell, H. E.; Grubbs, Macrocyclic compounds without the cyclopropyl moiety in the P1 part, i.e the macrocyclic ring extends directly from the peptidic backbone at the carbon adjacent $R^7$, can be prepared using the method described herein. An example wherein a 5 membered cycloakyl derivative is used as the P2 scaffold is shown in scheme 18.

Scheme 18

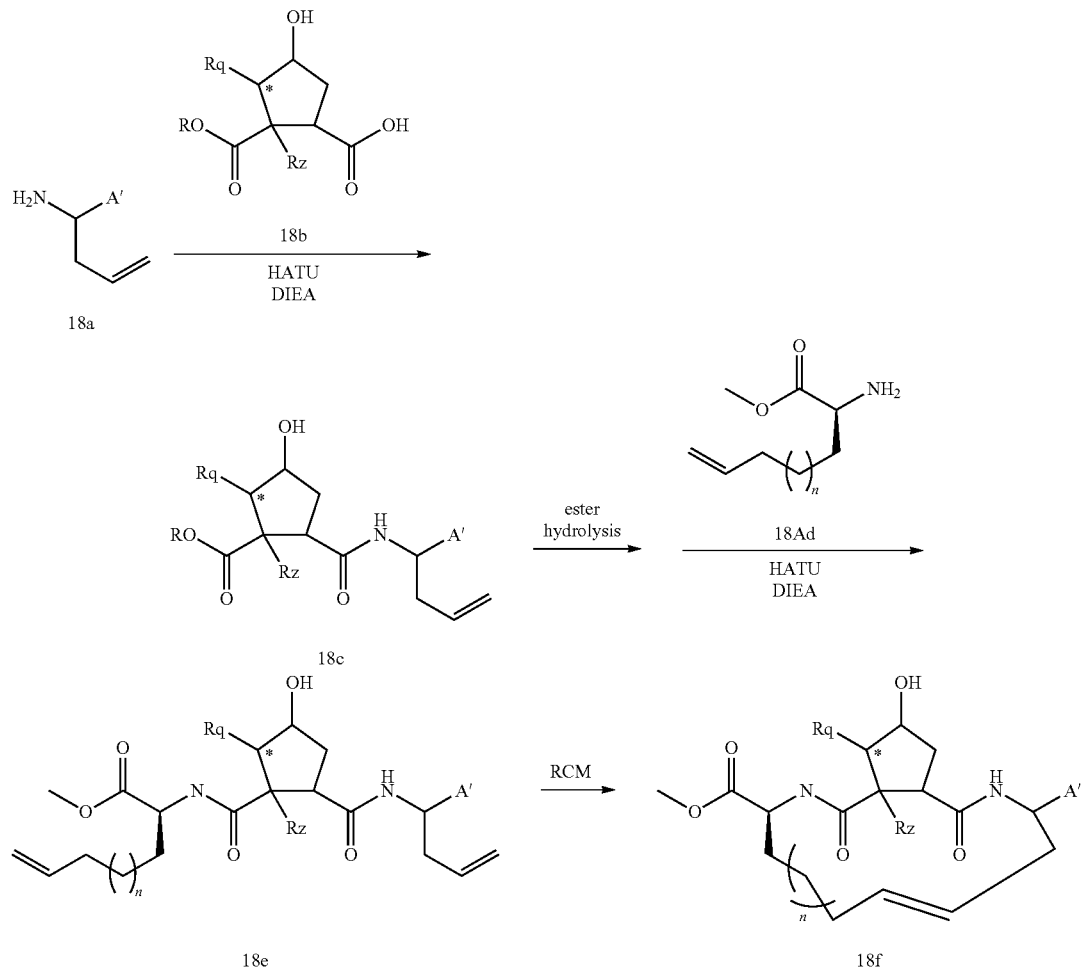

18e

A' is a protected carboxylic acid, substituted amide or sulfon amide.
n is 1, 2, 3, 4 or 5

R. H. J. Am. Chem. Soc. 118, (1996), 9606-9614, Kingsbury, J. S., Harrity, J. P. A., Bonitatebus, P. J., Hoveyda, A. H., J. Am. Chem. Soc. 121, (1999), 791-799 and Huang et al., J. Am. Chem. Soc. 121, (1999), 2674-2678. It will also be recognized that catalysts containing other transition metals such as Mo can be used for this reaction. Optionally the double bond is reduced and/or the ethyl ester is hydrolysed by standard hydrogenation and/or hydrolysation methods respectively well known in the art. Alternatively the methyl ester can be selectively hydrolysed followed by coupling of a $R^{18}$-G-P4 building block by standard peptide coupling conditions. The macrocyclisation step described in Scheme 17 can also be applied to the corresponding carbocyclic analogues described above. When the linker contains a nitrogen atom the ring closure can be carried out by reductive amination as described in WO00/59929.

Coupling of a suitable allylglycine derivative (18a), to the acid function of the P2 scaffold (18b) using standard peptide coupling conditions yields the amide derivative (18c). Hydrolysis of the ester group followed by a peptide coupling reaction with the olefin substituted amino acid (18Ad) provides the amide compound (18e). A ring closing metathesis reaction is then effected by using for example Hoveyda-Grubbs catalyst which gives the macrocyclic compound (18f).

Even though scheme 18 shows the synthetic sequence using a P2 scaffold with an unsubstituted hydroxy group, it will be apparent that the R8 substituent can be introduced at any convenient stage of the synthesis for example as described in scheme 9 and 10 or it can be introduced after the metathesis reaction, i.e. on compound 18f, using any of the methods described herein.

Building blocks to be used in the preparation of compounds wherein the macrocycle extends from the amide nitrogen in the P3 fragment i.e Rx is J in general formula VI, or in the preparation of compounds wherein the P3 and P4 fragments are absent, i.e. m and n are 0 and G is NRj in general formula VI, can typically be prepared as outlined in scheme 18B.

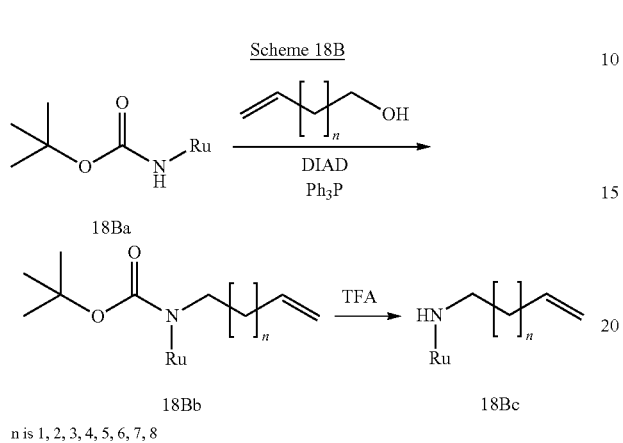

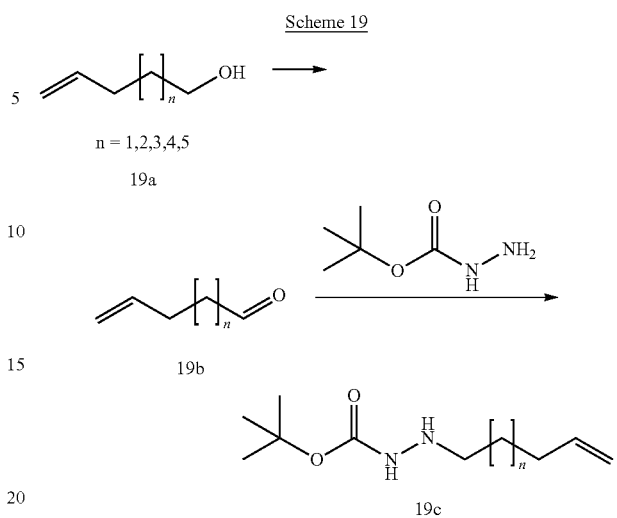

Carbamate 18Ba, which is commercially available or is readily prepared for instance by reaction of the desired alkyl amine with di-tert-butyl dicarbonate, can be reacted with an appropriate ω-unsaturated alcohol under Mitsunobu conditions to provide the alkylated carbamate (18Bb). Subjection of 188b to acidic conditions like for example treatment with trifluoroacetic acid in a solvent like dichloromethane gives the free amine (18Bc) which can be linked to a P2 fragment using any of the previously desorbed strategies.

Macrocyclic structures containing a hydrazine group i.e. T is NRd or m and n are 0 and G is NRjNRj, in general formula VI, can be prepared by linking a suitably N-alkylated carbazate derivative to the P2 fragment. Alkylated carbazate derivatives can be prepared, for example, as described in Scheme 19.

Oxidation of the appropriate alcohol (19a) effected by a suitable oxidation method like for example with N-methyl morpholine oxide and tetrapropylammonium perruthenate in a solvent like dichloromethane provides aldehyde (19b). Reductive alkylation of tert-butyl carbazate with the afforded aldehyde gives the desired N-alkylated building block (19c). Alternatively, any desired hydrazine derivative such as morpholin-1-ylamine, piperidin-1-ylamine or the like can be used instead of tert-butyl carbazate in the reaction with aldehyde 19b.

Scheme 20 illustrates synthetic sequences to building blocks suitable for the preparation of compounds wherein the "outer" nitrogen of the hydrazine group is alkylated, either with an w-unsaturated alkyl chain appropriate for subsequent macrocycle formation or with any other suitable alkyl group.

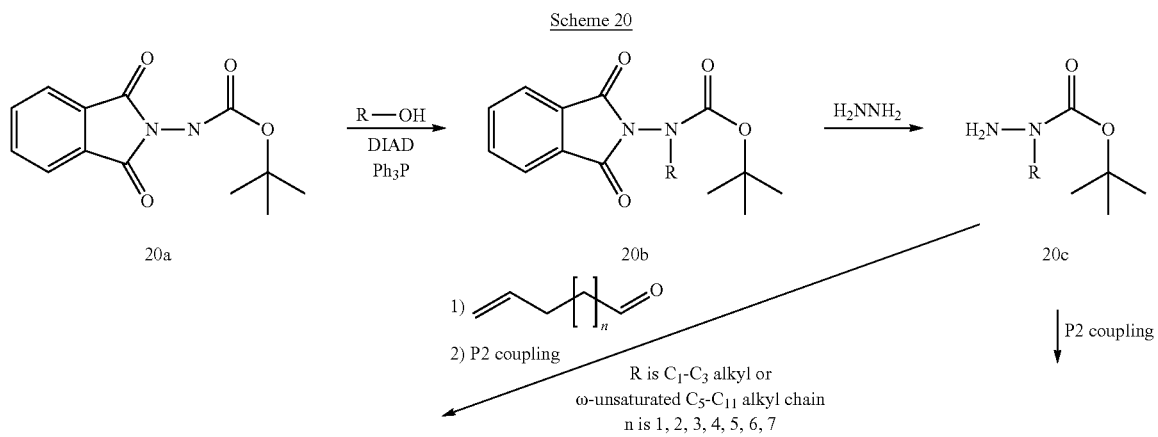

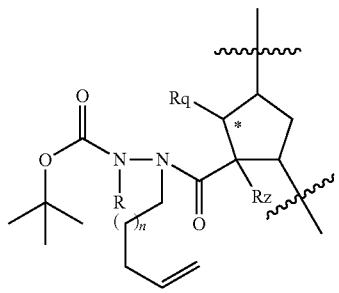

20e

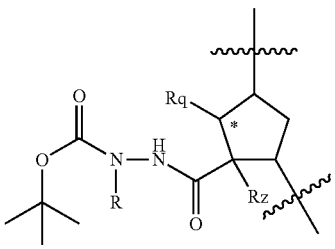

20d

Reaction of a suitably protected hydrazine derivative, for example (1,3-dioxo-1,3-dihydro-isoindol-2-yl)-carbamic acid tert-butyl ester (20a), which can easily be prepared by a person skilled in the art, with a desired alcohol, R—OH, under Mitsunobu conditions provides N-alkylated hydrazine compound (20b). Removal of the phtalimido group effected by treatment with hydrazine or a derivative thereof like hydrazine hydrate or hydrazine acetate provides the carbazate (20c). The afforded primary amine can then either be be coupled to any desired P2 fragment using any of the methods previously described to give 20d or alternatively it can be further alkylated using for example the reductive amination method described in scheme 19 followed by coupling to a P2 fragment as previously described to give 20.

Scheme 21 exemplifies the coupling of a hydrazine containing P3 building block to a cyclopentane scaffold followed by macrocyclisation.

Scheme 21

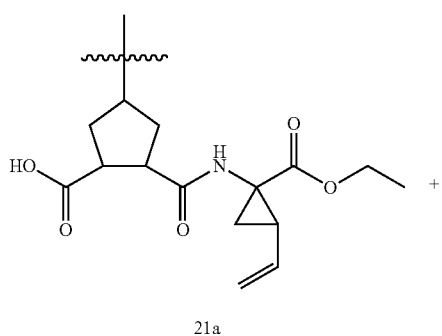

21a

+

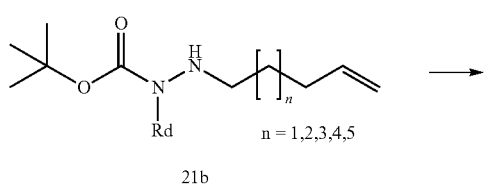

21b
n = 1,2,3,4,5

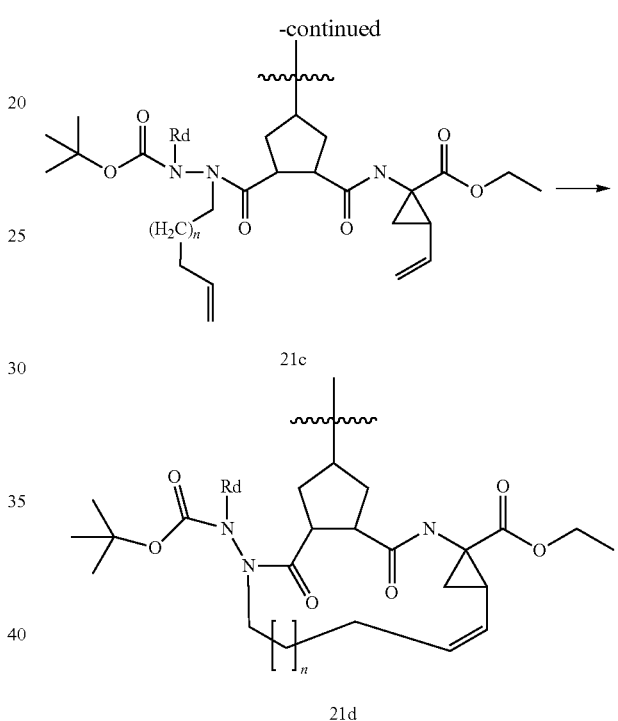

21c

21d

Coupling of the carbazate derivative (21b) to the P2-P1 building block (21a) using standard peptide coupling conditions provides intermediate (21c). Ring closure of (21c) by an olefin metathesis reaction as described in scheme 18 gives the macrocyclic compound (21d).

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoracetyl, trichloroacetyl, phthalyl, o-nitrophenoxyacetyl, α-chlorobutyryl, benzoyl, 4-chlorobenzoyl, 4bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyl-oxycarbonyl, p-methoxybenzyloxycarbonyl, p-nitrobenzyloxycarbonyl, 2-nitrobenzyloxycarbonyl, p-bromobenzyloxycarbonyl, 3,4- dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include Fmoc, formyl, acetyl, benzoyl, pivaloyl, t-butylacetyl, phenylsulfonyl, benzyl, t-butoxycarbonyl (BOC) and benzyloxycarbonyl (Cbz).

Hydroxy protecting group as used herein refers to a substituent which protects hydroxyl groups against undesirable reactions during synthetic procedures such as those O-protecting groups disclosed in Greene, "Protective Groups in Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

In treating conditions caused by flavivirus such as HCV, the compounds of formula VI are typically administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500-750 mg, in one to four dosage units per day. As with al pharmaceuticals, dosage rates will vary with the size and metabolic condition of the patient as well as the severity of the infection and may need to be adjusted for concomitant medications.

As is good prescribing practice with antiviral therapy, the compounds of formula I are typically coadministered with other HCV therapies to avoid the generation of drug escape mutants. Examples of such additional HCV antiviral therapies include ribavirin, interferons, including pegylated interferons. Additionally a number of nucleoside analogues and protease inhibitors are in clinical or preclinical development and will be amenable to co-administration with the compounds of the invention.

Accordingly a further aspect of the invention provides a composition comprising a compound of formula I and at least one further HCV antiviral in a common dosage unit, such as any of the dosage forms described below, but especially an orally administered tablet, or capsule or a liquid suspension or solution for oral or injection use. A further aspect of the invention provides a method for the treatment or prophylaxis of flavivirus infection, such as HCV, comprising the sequential or simultaneous administration of a compound of formula I and at least one further HCV antiviral. A related aspect of the invention provides a patient pack comprising a first pharmaceutical composition, preferably in unit dosage form, of the compound of formula I and a second pharmaceutical composition of a second HCV antiviral, typically also in unit dosage form and generally in a separate container within the patient pack. A patient pack will conveniently also be provided with instructions printed on the package or a container therein, or on a package insert, for the simultaneous or sequential administration of the respective pharmaceutical compositions.

Many HCV patients are co-Infected, or prone to superinfection, with other infectious diseases. Accordingly, a further aspect of the invention provides combination therapies comprising the compound of the invention co-formulated in the same dosage unit or co-packaged with at least one further anti-infective pharmaceutical. The compound of the invention and the at least one further antinfective are administered simultaneously or sequentially, typically at doses corresponding to the monotherapy dose for the agent concerned. However, certain antifectives can induce a synergistic response, allowing one or both of the active ingredients to be administered at a lower dose that the corresponding monotherapy. For example in drugs prone to rapid metabolism by Cyp3A4, co-dosing with the HIV protease inhibitor ritonavir can allow lower dosage regimes to be administered.

Typical coinfections or superinfections with HCV include hepatitis B virus or HIV. Accordingly the compound of the invention is advantageously co-administered (either in the same dosage unit, co-packaged or separately prescribed dosage unit) with at least one HIV antiviral and/or at least one HBV antiviral.

Representative HIV antivirals include NRTI such as alovudine (FLT), zudovudine (AZT, ZDV), stavudine (d4T, Zerit), zalcitabine (ddC), didanosine (ddl, Videx), abacavir, (ABC, Ziagen), lamivudine (3TC, Epivir), emtricitabine (FTC, Emtriva), racevir (racemic FTC), adefovir (ADV), entacavir (BMS 200475), alovudine (FLT), tenofovir disoproxil fumarate (TNF, Viread), amdoxavir (DAPD), D-d4FC (DPC-817), -dOTC (Shire SPD754), elvucitabine (Achllion ACH-126443), BCH 10681 (Shire) SPD-756, racivir, D-FDOC, G07340, iNK-20 (thioether phospholipid AZT, Kucera), 2'3'-dideoxy-3'-fluoroguanosine (FLG) & its prodrugs such as MIV-210, reverset (RVT, D-D4FC, Pharmasset DPC-817).

Representative NNRTI include delavirdine (Rescriptor), efavirenz (DMP-266, Sustiva), nevirapine (BIRG-587, Viramune), (+)calanolide A and B (Advanced Life Sciences), capravirine (AG1549f S-1153; Pfizer), GW-695634 (GW-8248; GSK), MIV-150 (Medivir), MV026048 (R-1495; Medivir AB/Roche), NV-05 2 2 (Idenix Pharm.), R-278474 (Johnson & Johnson), RS-1588 (Idenix Pharm.), TMC-120/125 (Johnson & Johnson), TMC-125 (R-165335; Johnson & Johnson), UC-781 (Biosyn Inc.) and YM215389 (Yamanoushi).

Representative HIV protease inhibitors include PA-457 (Panacos), KPC-2 (Kucera Pharm.), 5 HGTV-43 (Enzo Biochem), amprenavir (VX-478, Agenerase), atazanavir (Reyataz), indinavir sulfate (MK-639, Crixvan), Lexiva (fosamprenavir calcium, GW-433908 or 908, VX-175), ritonavir (Norvir), lopinavir+ritonavir (ABT-378, Kaletra), tipranavir, nelfinavir mesylate (Viracept), saquinavir (Invirase, Fortovase), AG1776 (JE-2147, KNI-784; Nippon Mining Holdings), AG-1859 (Pfizer), DPC-681/684 (BMS), GS224338; Gilead Sciences), KNI-272 (Nippon Mining Holdings), Nar-DG-35 (Narhex), P(PL)-100 (P-1946; Procyon Biopharma), P-1946 (Procyon Biopharma), R-944 (Hoffmann-LaRoche), RO-0334649 (Hoffmann-LaRoche), TMC-114 (Johnson & Johnson), VX-385 (GW40385; GSK/Vertex), VX-478 (Vertex/GSK).

Other HIV antivirals include entry inhibitors, including fusion inhibitors, inhibitors of the CD4 receptor, inhibitors of the CCR5 co-receptor and inhibitors of the CXCR4 coreceptor, or a pharmaceutically acceptable salt or prodrug thereof. Examples of entry inhibitors are AMD-070 (AMD11070; AnorMed), BlockAlde/CR (ADVENTRX Pharm.), BMS 806 (BMS-378806; BMS), Enfurvirtide (T-20, R698, Fuzeon), KRH1636 (Kureha Pharmaceuticals), ONO-4128 (GW-873140, AK-602, E-913; ONO Pharmaceuticals), Pro-140 (Progenics Pharm), PRO542 (Progenics Pharm.), SCH-D (SCH-417690; Schering-Plough), T-1249 (R724; Roche/Trimeris), TAK-220 (Takeda Chem. Ind.), TNX-355 (Tanox) and UK-427,857 (Pfizer). Examples of integrase inhibitors are L-870810 (Merck & Co.), c-2507 (Merck & Co.) and S(RSC)-1838 (shionogi/GSK).

Examples of HBV antivirals include adefovir dipivoxil (Hepsera), and especially lamivudine and 2'3'-dideoxy-3'-fluoroguanosine (FLG) & its prodrugs such as MIV-210, the 5'-O-valyl-L-lactyl prodrug of FLG. These latter HBV antivirals are particularly convenient as they are also active against HIV.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (Including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and Intimately bringing into association the active agent with liquid carriers or finely divided sold carriers or both, and then if necessary shaping the product. The invention extends to methods for preparing a pharmaceutical composition comprising bringing a compound of Formula VI or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-n-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic add; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The compounds of formula VI can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The invention further extends to salts of the compounds of formula I which may or may not be pharmaceutically acceptable, but which are useful as synthetic intermediates, the salt moiety being displaced or replaced as necessary.

The invention includes prodrugs of the compounds of formula I. Prodrugs of the compounds of formula VI are those compounds which following administration to a patient release a compound of the formula VI in vivo generally following hydrolysis in the gut, liver or plasma. Typical prodrugs are pharmaceutically acceptable ethers and especially esters (including phosphate esters) of hydroxy functions, pharmaceutically acceptable amides or carbamates of amine functions or pharmaceutically acceptable esters of carboxy functions. Preferred pharmaceutically acceptable esters include alkyl esters, including acetyl, ethanoyl, butyryl, t-butyryl, stearyl and pivaloyl, phosphate esters and sulphonic esters (ie those derived from $RSO_2OH$, where R is lower alkyl or aryl). Pharmaceutically acceptable esters include lower alkyl ethers and the ethers disclosed in WO00/47561, especially methoxyaminoacyl and ethoxyaminoacyl.

The compounds of the invention have various steric centres and the invention extends to racemates and enantiomers at each of these steric centres.

Typically, the stereochemistry of the groups corresponding to the P3 and P4 side chains (ie $R^{15}$ and/or $R^{11}$) will correspond to an L-amino acid configuration, although the invention also extends to D-isomers at one or both of these centres. It is noteworthy that the L configuration is active notwithstanding that the nature of the E moiety means that P3 and P4 are typically translated one atom relative to a conventional polypeptide and the fact that reversal of a peptide residue, as envisaged for P3 and P4 then pitches the amine acid side chain to the opposite side compared to a conventional peptide substrate.

The stereochemistry of the backbone component of the cyclic P2 group (i.e. spanning the carbonyl of the P1 amide bond and the carbonyl extending of P3 will typically correspond to L-proline. The stereochemistry of the P2 ring atom to which W is bonded is typically as shown:

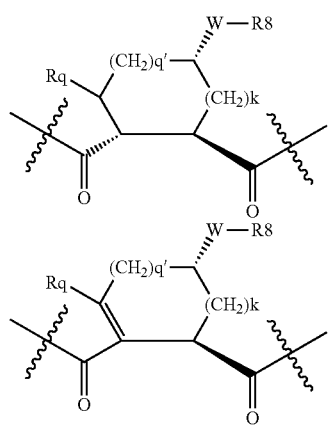

In compounds of the invention wherein $R^7$ and $R^{7'}$ together define a spiroalkyl group, such a spiro-cycloakyl will typically comprise an R substituent on the spiro-cyclopropyl ring which is is orientated syn to A

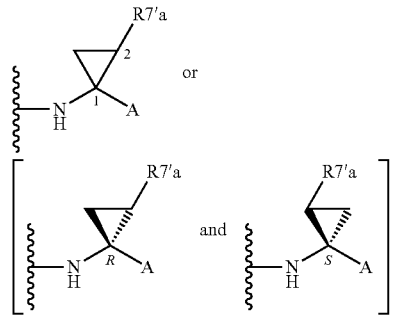

or anti to A:

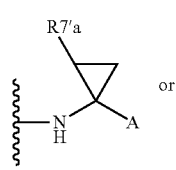

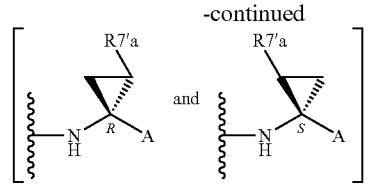

Conveniently, the spiro carbon of such a spiro-cyclopropyl ring has the R configuration:

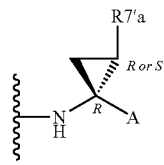

Conveniently an $R^{7'a}$ substituent on a spiro-cyclopropyl ring adjacent to A is in a syn orientation in the following absolute configuration:

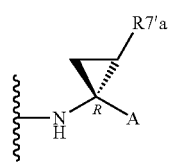

Particularly preferred variants have $R^{7'a}$ include ethyl, hence the asymmetric carbon atoms at position 1 and 2 have the R. R configuration. Alternative preferred R Include vinyl, hence the asymmetric carbon atoms at position 1 and 2 have the R, S configuration.

Where the compound of the invention is a macrocycle comprising a J group, J is preferably a diastereomer represented by partial structures (i) or (ii):

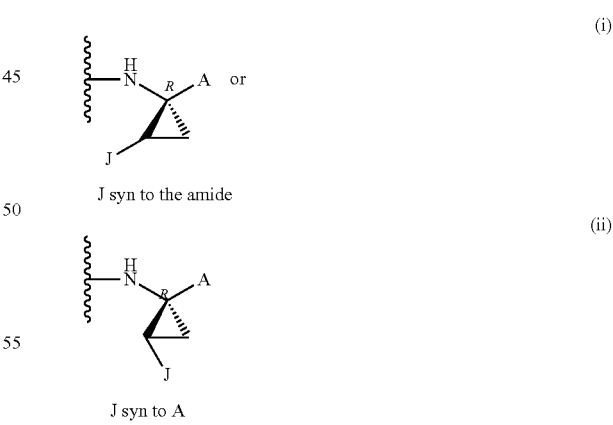

especially where J is syn to A.

DETAILED DESCRIPTION OF THE EMBODIMENTS

Various embodiments of the invention will now be described by way of illustration only with reference to the following non-limiting examples.

Example 1

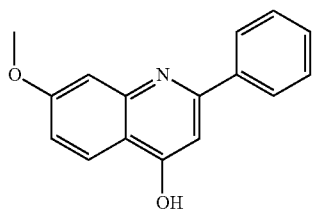 [SMILES: COc1ccc2c(O)cc(-c3ccccc3)nc2c1]

7-Methoxy-2-phenyl-quinolin-4-ol (1)

To a stirred round bottled flask with toluene (100 mL) ethyl benzoyl acetate (18.7 g, 97 mmol) and m-anisidine (12 g, 97 mmol) was added. 4 M HCl in dioxane (0.5 mL) was added and the reaction mixture was refluxed for 6 h (140° C.). The mixture was co-evaporated with toluene. To the crude mixture diphenyl ether (50 mL) was added and the mixture was heated to 280° C. for 2 h. When the theoretical amount ethanol (6 mL) was collected in a Dean Stark trap the heating was stopped and the mixture was cooled to rt. The crude mixture was dissolved in $CH_2Cl_2$ (100 mL) and stirred for 30 min. The formed precipitate was filtered off and dried which gave 1 (4.12 g, 16.4 mmol, 17%): pale yellow powder.

$^1$H (300 MHz, DMSO-$D_6$): δ 3.8 (s, 3H), 6.24 (s, 1H), 6.88-6.96 (dd, 1H, J=9.07 Hz, J=2.47 Hz), 7.19 (d, 1H, J=2.19 Hz), 7.56 (t, 3H, J=2.19 Hz), 7.8 (dd, 2H, J=7.14 Hz, J=2.19 Hz), 8.0 (d, 1H, J=9.06 Hz); $^{13}$C (75.5 MHz, DMSO-$D_6$): δ 55.3, 99.6, 106.9, 113.1, 119.1, 126.4, 127.5, 128.8, 130.2, 134.1, 142.2, 149.4, 161.8, 176.4.

Example 2

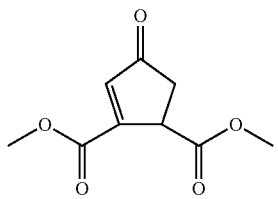

(Rac)-4-oxocyclopent-2-ene-1, 2-dicarboxylic acid dimethyl ester (2)

(1R,2S)-4-oxo-cyclopentane-1, 2-dicarboxylic acid dimethyl ester (4.8 g, 23.8 mmol) and $CuBr_2$ (11.9 g, 532 mmol) were dissolved in dry THF (70 mL) and the mixture was refluxed for two hours at 90° C. The formed CuBr was filtrated off and the organic phase was concentrated. $CaCO_3$ (2.7 g, 27.2 mmol) and DMF (70 mL) were added and the mixture was held at 100° C. for one hour. The dark brown mixture was poured over ice (35 g) and the formed precipitate was filtrated off. The aqueous layer was extracted with ethyl acetate (1×300 mL+3×150 mL). The organic phases were dried, filtrated and concentrated. Purification by flash chromatography (toluene/EtOAc 9:1) gave 2 (2.1 g, 45%) as yellow crystals

Example 3

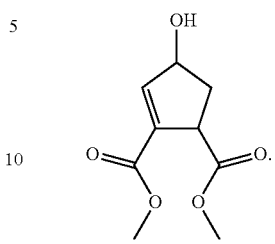

((1S,4R) & (1R,4S))-4-hydroxy-cyclopent-2-ene-1, 2-dicarboxylic add dimethyl ester (3)

To a cold solution (−30° C.) of 2 (3.18 g, 16.1 mmol) dissolved in MeOH (23 mL), $NaBH_4$ (0.66 g, 17.5 mmol) was added. After nine minutes the excess of $NaBH_4$ was destroyed by adding brine (80 mL). The mixture was concentrated and extracted with ethyl acetate (4×80 mL). The organic phases were dried, filtrated and concentrated and gave 3 (3.0 g, 92%) as a yellow oil.

Example 4

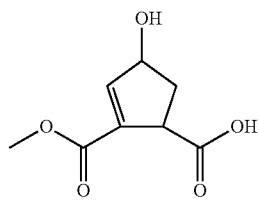

(1 S,4R) & (1R,4S)-4-hydroxy-cyclopent-2-ene-1,2-dicarboxylic add 2-methyl ester (4)

To an ice-cold solution of 3 (3.4 g, 22 mmol) dissolved in dioxane and water (1:1, 110 mL), LiOH (0.52 g, 22 mmol) was added. After two and a half hours the mixture was co-evaporated with toluene and methanol. Purification by flash chromatography (toluene/Ethyl acetate 3:1+1% HOAc) gave the title compound (1.0 g, 27%) as yellow-white crystals.

$^1$H-NMR (300 MHz, $CD_3OD$): δ 1.78-1.89 (m, 1H), 2.70-2.84 (m, 1H), 3.56-3.71 (m, 1H), 3.76 (s, 3H), 4.81-4.90 (m, 1H), 6.76-6.81 (m, 1H); $^{13}$C-NMR (75.5 MHz, $CDCl_3$): δ 38.0, 48.0, 52.4, 75.7, 137.0, 148.2, 165.0 178.4.

Example 5

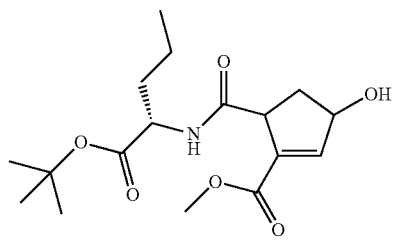 [SMILES: CCC[C@H](NC(=O)C1CC(O)C=C1C(=O)OC)C(=O)OC(C)(C)C]

((3S,5R) & (3R,5S))-5-((S)-1-tert-Butoxycarbonyl-butylcarbamoyl)-3-hydroxy-cyclopent-1-enecarboxylic acid methyl (5)

To an ice cooled solution of 4 (0.20 g, 1.1 mmol) and 2-amino-pentanoic add tert.butyl ester (0.24 g, 1.4 mmol) in DMF (7 mL), DIPEA (0.18 g, 1.4 mmol) and HATU (0.53 g, 1.4 mmol) were added. After two hours the solution was concentrated and purified using column chromatography (toluene/ethyl acetate 3:1). This gave the title compound as a yellow oil (0.22 g, 63%).

$^1$H-NMR (300 MHz, CDCl$_3$): δ 0.84-0.96 (m, 3H), 1.14-1.39 (m, 2H), [(1.44 & 1.49) s, 9H], 1.50-1.60 (m, 1H), 1.61-1.85 (m, 1H), 1.97-2.10 (m, 1H), 2.11-2.28 (m, 1H), 3.57-3.68 (m, 1H), [(3.73 & 3.76) s, 3H], 4.30-4.50 (m, 1H), 4.63-4.73 (m, 1H), 6.8068.95 (m, 1H), 6.95-7.00 (m, 1H).

Example 6

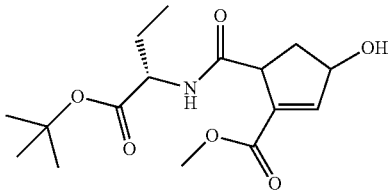 [SMILES: CC[C@H](NC(=O)C1CC(O)C=C1C(=O)OC)C(=O)OC(C)(C)C]

((3S,5R) & (3R,5S))-5-((S)-1-tert-Butoxycarbonyl-propylcarbamoyl-3-hydroxy-cyclopent-1-necarboxylic acid methyl ester (6)

Reaction of 4 (141 mg, 76 mmol) according to the method described for the preparation of 5 using L-2-amino-N-butyric acid tert.butyl ester instead of 2-amino-pentanoic acid tert.butyl ester gave the title compound as a slightly yellow oil (171 mg, 69%).

$^1$H-NMR (300 MHz, CDCl$_3$): δ 0.89-0.98 (m, 3H), [(1.42 & 1.44) s, H], 1.60-1.78 (m, 1H), 1.79-1.95 (m, 1H), 1.99-2.11 (m, 1H), 2.18-2.30 (m, 1H), 3.58-3.65 (m, 1H), [3.75 & 3.78] s, 3H], 4.22-4.39 (m, 1H), 4.61-4.66 (m, 1H), 6.77-6.90 (m, 1H), 6.91-6.92 (m, 1H).

Example 7

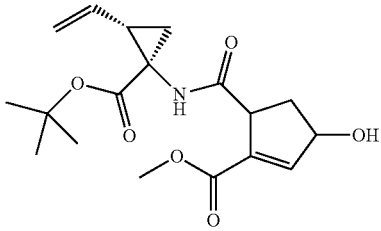 [SMILES: C=C[C@@H]1C[C@]1(NC(=O)C1CC(O)C=C1C(=O)OC)C(=O)OC(C)(C)C]

((3S,5R) & (3R,6S'))-5-((1R,2S)-1-tert-Butoxycarbonyl-2-vinyl-cyclopropylcarbamoyl)-3-hydroxy-cyclopent-1-enecarboxylic acid methyl ester (7)

Reaction of 4 (50 mg, 37 mmol) according to the method described for the preparation of 5 using (1R, 2S)-1-amino-2-vinyl-cyclopropane carboxylic acid tert.butyl ester instead of 2-amino-pentanoi acid tert.butyl ester provided the title compound as a slightly yellow oil (650 mg, 38%).

$^1$H-NMR (300 MHz, CDCl$_3$): δ [(1.38 & 1.42) s, 9H], 1.75-1.83 (m, 1H), 2.00-2.21 (m, 3H), 3.55-3.63 (m, 1H), [(3.77 & 3.82) s, 3H], 4.20-4.38 (m, 1H), 4.65-4.80 (m, 1H), 5.13-5.20 (m, 1H), 5.22-5.38 (m, 1H), 5.60-6.82 (m, 1H), 6.95-8.96 (m, 2H).

Example 8

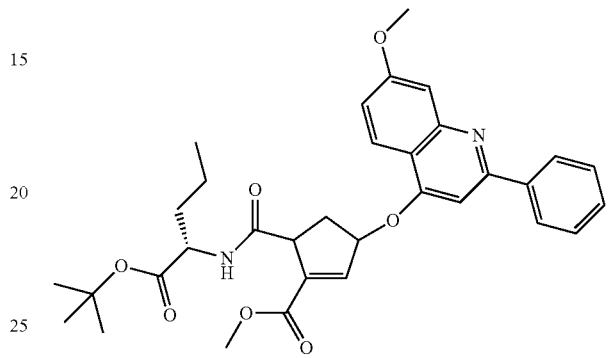

((3R,5R) & (3S,5S))-5-((S)-1-tert-Butoxycarbonyl-butylcarbamoyl)-3-(7-methoxy-2-phenyl-quinolin-4-yloxy)-cyclopent-1-enecarboxylic acid methyl ester (8)

To an ice cooled solution of 5 (0.23 g, 0.67 mmol) in dry THF, 7-methoxy-2-phenyl-quinolin-4-ol (0.22 g, 0.88 mmol) and triphenylphosphine (0.23 g, 0.88 mmol) were added. Then DIAD (0.19 g, 0.92 mmol) was dissolved in THF (2 mL) and added dropwise to the solution. After one hour the mixture was concentrated and purified using flash chromatography (toluene/ethyl acetate 3:1). This gave the title compound as a white powder (0.30 g, 77%).

$^1$H-NMR (300 MHz, CDCl$_3$): δ 0.88-1.00 (m, 3H), 1.18-1.43 (m, 2H), [(1.45 & 1.50) s, 9H], 1.53-1.65 (m, 1H), 1.68-1.85 (m, 1H), 2.29-2.43 (m, 1H), 3.10-3.25 (m, 1H), [(3.79 & 3.83) s, 3H], 3.97 (s, 3H), 4.05-4.20 (m, 1H), 4.38-4.50 (m, 1H), 6.03-6.13 (m, 1H), 6.65-8.90 (m, 1H), 7.04-7.18 (m, 3H), 7.40-7.56 (m, 4H), 8.00-8.12 (m, 3H).

Example 9

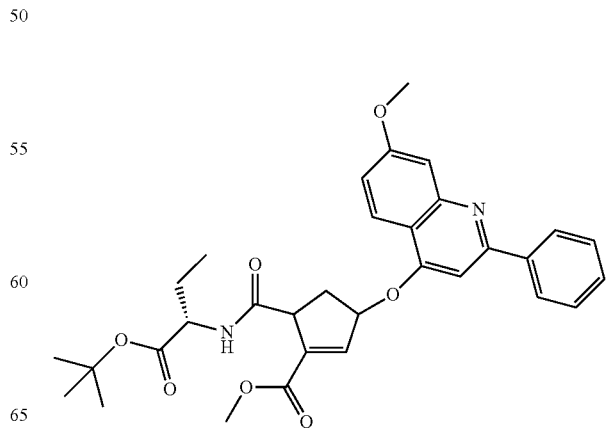

((3R,5R) & (3S,5S))-5-((S)-1-tert-Butoxycarbonyl-propylcarbamoyl)-3-(7-methoxy-2-phenyl-quinolin-4-yloxy)-cyclopent-1-enecarboxylic acid methyl ester (9)

Reaction of 6 (132 mg, 40 mmol) according to the method described for the preparation of 8 gave the title compound as a yellow oil (137 mg, 61%).

$^1$H-NMR (300 MHz, CDCl$_3$): δ 0.83-0.98 (m, 3H), [(1.42 & 1.44) a, 9H], 1.65-1.78 (m, 1H), 1.80-1.97 (m, 1H), 2.30-2.40 (m, 1H), 3.05-3.20 (m, 1H), [(3.78 & 3.80) s, 3H], 3.94 (s, 3H), 3.95-4.01 (m, 1H), 4.38-4.44 (s, 1H), 6.05-6.15 (m, 1H), 6.80-6.94 (m, 1H), 7.02-7.15 (m, 3H), 7.38-7.55 (m, 4H), 7.97-8.18 (m, 3H).

Example 10

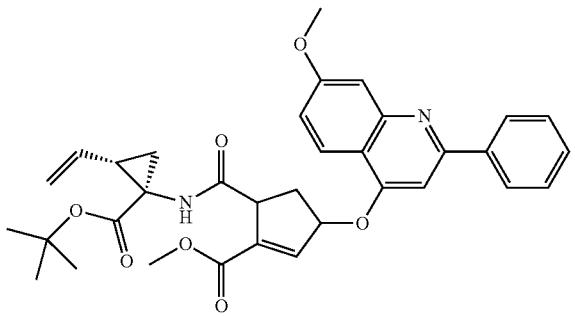 [SMILES: C=C[C@@H]1C[C@]1(NC(=O)C1CC(Oc2cc(-c3ccccc3)nc3cc(OC)ccc23)C=C1C(=O)OC)C(=O)OC(C)(C)C]

((3R,5R) & (3S,5S))-5-((1R,2S)-1-tert-Butoxycarbonyl-2-vinyl-cyclopropylcarbamoyl)-3-(7-methoxy-2-phenyl-quinolin-4-yloxy)-cyclopent-1-enecarboxylic acid methyl ester (10)

Reaction of 7 (41 mg, 116 mmol) according to the method described for the preparation of 8 provided the title compound as a yellow oil.

$^1$H-NMR (300 MHz, CDCl$_3$): δ 1.52-1.57 (m, 1H), 1.58 (m, 9H), 1.80-1.83 (m, 1H), 2.00-2.17 (m, 1H), 2.20-2.38 (m, 1H), 3.20-3.37 (m, 1H), 3.80 (s, 3H), 3.81-3-3.98 (m, 1H), 3.99 (s, 3H), 5.12-6.20 (m, 1H), 5.22-5.40 (m, 1H), 5.63-5.80 (m, 1H), 6.05-6-20 (m, 1H), 7.00-7.21 (m, 4H), 7.40-7.58 (m, 4H), 8.02-8.18 (m, 3H).

Example 11

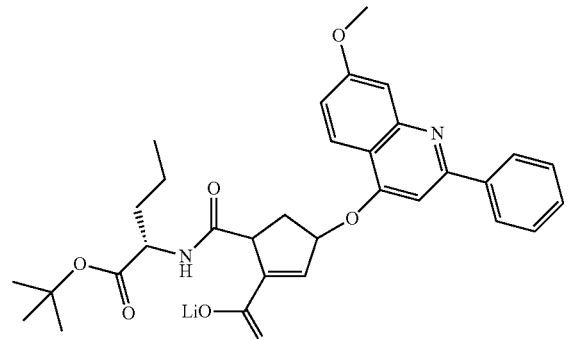

((3R,5R) & (3S,5S))-5-((S-1-tert-Butoxycarbonyl-butylcarbamoyl)-3-(7-methoxy-2-phenyl-quinolin-4-yloxy)-cyclopent-1-enecarboxylic acid (11)

The methyl ester 8 (0.35 g, 0.61 mmol) was dissolved in dioxane/water (1:1, 7 mL) and LiOH (0.031 g, 1.3 mmol) was added. The reaction was stirred over night and then co-concentrated. This gave the lithium salt of 11 (0.32 g, 90%) as a brown powder.

Example 12

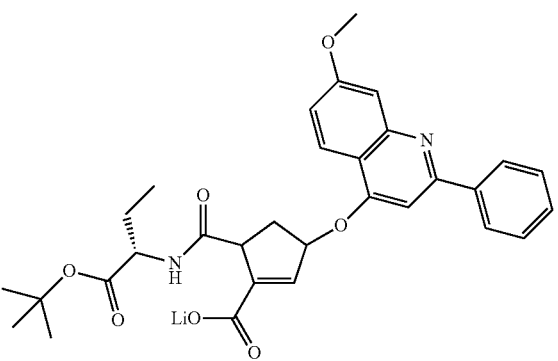

((3R,5R) & (3S,5S))-5-((S)-1-tert-Butoxycarbonyl-propylcarbamoyl)-3-(7-methoxy-2-phenyl-quinolin-4-yloxy)-cyclopent-1-enecarboxylic acid (12)

Reaction of 9 (225 mg, 40 mmol) according to the method described for the preparation of 11 provided the title compound as yellow salt (157 mg, 72%).

Example 13

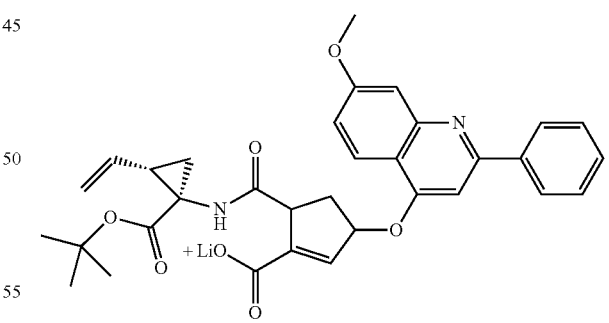

((3R,5R) & (3S,5S))-5-((1R,2S)-1-tert-Butoxycarbonyl-2-vinyl-cyclopropylcarbamoyl)-3-(7-methoxy-2-phenyl-quinolin-4-yloxy)-cyclopent-1-enecarboxylic Acid (13)

Reaction of 10 (35 mg, 59 mmol) according to the method described for the preparation of 11 (33 mg, 97%) provided the title compound as a yellow salt.

Example 14

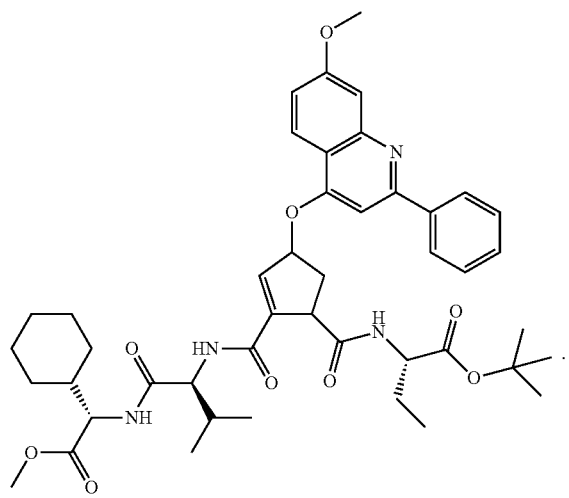 [SMILES: CC[C@H](NC(=O)C1CC(Oc2cc(-c3ccccc3)nc3cc(OC)ccc23)C=C1C(=O)N[C@H](C(=O)N[C@H](C(=O)OC)C1CCCCC1)C(C)C)C(=O)OC(C)(C)C]

(S)-2-{[((1R,4S) & (1R,4R))-2-{(S)-1-[((S)-Cyclo-hexyl-methoxycarbonyl-methyl)-carbamoyl]-2-methyl-propylcarbamoyl}-4-(7-methoxy-2-phenyl-quinolin-4-yloxy)-cyclopent-2-enecarbonyl]-amino}-butyric acid tert-butyl ester (14)

The add 12 (38.4 mg, 0.070 mmol) and (2-amino-3-methyl-butyrylamino)-cyclohexyl acetic acid methyl ester (26.6 mg, 0.098 mmol) were dissolved in DMF (1.5 mL) and cooled in an ice-bath. DIPEA (17.1 µL, 0.096 mmol) and HATU (37.4 mg, 0.098 mmol) were added. After ninety minutes the mixture was co-concentrated with toluene and methanol and then purified by lash column chromatography (toluene/ethyl acetate 6:1). Further purification was performed on HPLC (90% MeOH+0.2% TEA). The diastereomeric mixture 14 was concentrated and gave a slightly yellow oil (20.6 mg, 37%). After lyophilisation 14 was collected as a white powder. $^1$H-NMR (300 MHz, CDCl$_3$): δ 0.93-1.02 (m, 9H), 1.03-1.25 (m, 4H), 1.44 (s, 9H), 1.65-1.86 (m, 9H), 2.05-2.10 (m, 1H), 2.22-2.40 (m, 1H), 3.05-3.20 (m, 1H), 3.77 (s, 3H), 3.98 (s, 3H), 4.18-422 (m, 1H), 4.38-4.60 (m, 3H), 6.01-6.10 (m, 1H), 6.61-6.70 (m, 2H), 6.80-6.85 (m, 1H), 7.05-7.18 (m, 2H), 7.40-7.58 (m, 5H), 8.00-8.13 (m, 3H). $^{13}$C-NMR (75.5 MHz, CDCl$_3$): δ 9.7, 18.4, 19.2, (25.9 & 26.11, [28.2 & 28.5], 29.6, 32.0, 37.3, 41.0, 46.2, 50.7, 52.4, 54.4, 55.8, 57.2, 58.5, 82.0, 82.8, 98.4, 110.2, 118.4, 120.1, 123.2, 127.9, 128.2, 128.9, 129.5, 131.2, 135.1, 135.2, 142.7, 144.2, 161.6, 164.3, 164.7, 170.9, 171.4, 172.4. MALDI-TOF m/z 821.56 [(M+Na)$^+$ calcd for C$_{45}$H$_{58}$N$_4$NaO$_9^+$ 821.41].

Example 15

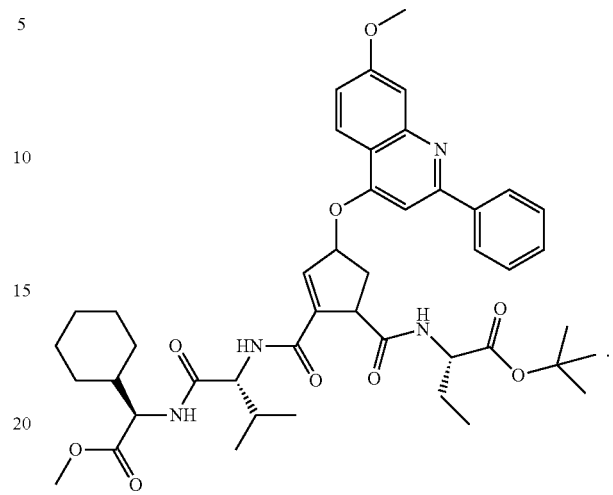

(S)-2-[((1R,4R) & (1 S,4S))-2-{(R)-1-[((R)-Cyclo-hexyl-methoxycarbonyl-methyl)-carbamoyl]-2-methyl-propylcarbamoyl}-4-(7-methoxy-2-phenyl-quinolin-4-yloxy)-cyclopent-2-enecarbonyl]-amino)-butyric add tert-butyl eater (15)

Reaction of 12 (20 mg, 37 mmol) according to the method described for the preparation of 14 using (2-amino-3-methyl-butyrylamino)-(R)-cyclohexyl acetic acid methyl ester instead of (2-amino-3-methyl-butyrylamino)-(S)-cyclohexyl acetic acid methyl ester, gave the title compound (19 mg, 66%) as a white powder.

$^1$H-NMR (300 MHz, CDCl$_3$): δ 0.91-0.98 (m, 3H), 0.99-1.10 (m, 6H), 1.11-1.38 (m, 4H), [(1.43 & 1.45) s, 9H], 1-45-1.94 (m, 9H), 2.05-2.18 (m, 1H), 2.22-2.40 (m, 1H), 3.16-3.24 (m, 1H), 3.77 (s, 3H), 3.98 (s, 3H), 4.04-4.18 (m, 1H), 4.36-4.57 (m, 3H), 6.00-4.08 (m, 1H), 6.13-6.21 (m, 1H), 6.62-6.70 (m, 1H), 8.81-6.85 (m, 1H), 7.05-7.18 (m, 3H), 7.41-7.57 (m, 4H), 8.02-8.13 (m, 3H). $^{13}$C-NMR (75.5 MHz, CDCl$_3$): δ 9.3, 18.2, 19.0, [25.5 & 25.9], [28.0 & 28.3], 29.4, 31.4, 32.1, 35.7, 40.7, 50.4, 52.2, 54.2, 55.5, 57.0, 58.2, 81.8, 82.4, 982, 107.5, 115.0, 118.1, 122.9, 127.6, 128.7, 128.8, 128.9, 129.2, 135.1, 140.4, 142.2, 151.4, 181.3, 163.9, 170.4, 170.9, 171.2, 172.0. MALDI-TOF m/z 821.60 [(M+Na)$^+$ calcd for C$_{45}$H$_{58}$N$_4$NaO$_9^+$ 821.41].

Example 16

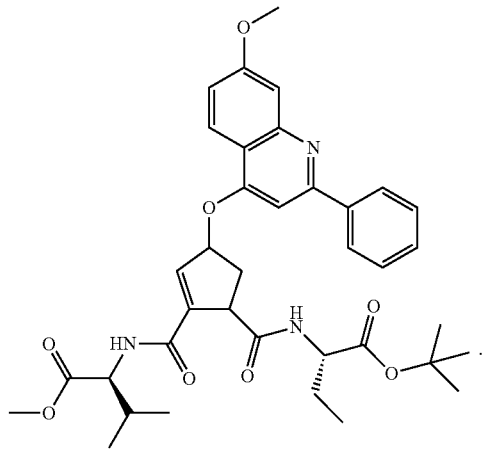 [SMILES: CC[C@H](NC(=O)C1CC(Oc2cc(-c3ccccc3)nc3cc(OC)ccc23)C=C1C(=O)N[C@H](C(=O)OC)C(C)C)C(=O)OC(C)(C)C]

(S)-2-{[((3R,5R) & (3S,5S))-5-((S)-1-tert-Butoxy-carbonyl-propylcarbamoyl)-3-(7-methoxy-2-phenyl-quinolin-4-yloxy)-cyclopent-1-enecarbonyl]-amino}-3-methyl-butyric acid methyl ester (16)

Reaction of 12 (24 mg, 44 mmol) according to the method described for the preparation of 14 using D-valine methyl ester instead of (2-amino-3-methyl-butyrylamino)cyclohexyl acetic acid methyl ester, gave the title compound (27 mg, 97%) as a white powder.

$^1$H-NMR (300 MHz, CDCl$_3$): δ 0.82-0.99 (m, 9H), [(1.42 & 1.44) s, 9H] 1.65-1.95 (m, 2H), 2.18-2.25 (m, 1H), 2.26-2.40 (m, 1H), 3.20-3.25 (m, 1H), 3.75 (s, 3H), 3.97 (s, 3H), 4.15-4.19 (m, 1H), 4.36-4.43 (m, 1H), 4.64-4.75 (m, 1H), 6.03-6.15 (m, 1H), 6.80-6.85 (m, 2H), 7.10-7.20 (m, 3H), 7.42-7.58 (m, 4H), 8.0-8.10 (m, 3H). $^{13}$C-NMR (75.5 MHz, CDCl$_3$): δ 9.7, [18.2 & 19.1], 25.7, [28.1 & 28.2], 32.0, 35.6, 50.4, 52.4, 54.5, 55.7, 57.6, 81.7, 82.7, 98.4, 107.7, 115.2, 118.4, 123.2, 127.8, 129.0, 129.2, 129.5, 134.8, 135.0, 140.4, 142.5, 151.6, 159.6, [161.1 & 161.5], 164.6, 171.1, 172.2. MALDI-TOF m/z 682.51[(M+Na)$^+$ calcd for C$_{37}$H$_{45}$N$_3$NaO$_8{}^+$ 682.31].

Example 17

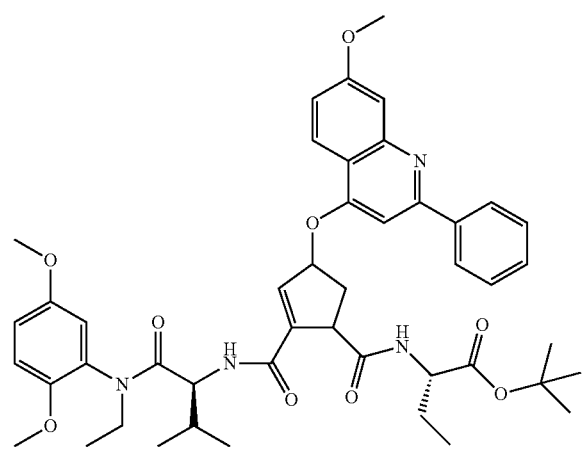 [SMILES: CC[C@H](NC(=O)C1CC(Oc2cc(-c3ccccc3)nc3cc(OC)ccc23)C=C1C(=O)N[C@H](C(=O)N(CC)c1cc(OC)ccc1OC)C(C)C)C(=O)OC(C)(C)C]

(S)-2-{[(1R,4R) & (1S,4S))-2-{(S)-1-[(2,5-Dimethoxy-phenyl)-ethyl-carbamoyl]-2-methyl-propylcarbamoyl}-4-(7-methoxy-2-phenyl-quinolin-4-yloxy)-cyclopent-2-enecarbonyl]-amino}-butyric acid tert-butyl ester (17)

Compound 17 (28.6 mg, 59%) was prepared from 12 (33 mg, 60 mmol) according to the method for the preparation of 14 using 2-amino-N-(2,5-dimethoxy-phenyl)-N-ethyl-3-methyl butyramide instead of (2-amino-3-methyl-butyrylamino)-cyclohexyl acetic add methyl ester. This gave the title compound as a white powder.

$^1$H-NMR (300 MHz, CDCl$_3$): δ 0.75-0.95 (m, 9H) 1.05-1.18 (m, 3H), [(1.42 & 1.44) s, 9H], 1.60-1.95 (m, 3H), 2.20-2.40 (m, 1H), 3.20-3.34 (m, 1H), 3.60-3.80 (m, 2H), [3.62-3.65 (m, 3H)], [3.79-3.82 (m, 3H)], 3.98 (s, 3H), 4.02-4.18 (m, 1H), 4.30-4.44 (m, 2H), 6.05-6.18 (m, 1H), 6.60-6.63 (m, 1H), 6.77-6.80 (m, 2H), 6.85-6.93 (m, 2H), 7.12-7.20 (m, 2H), 7.35-7.60 (m, 5H), 8.02-8.20 (m, 3H). $^{13}$C-NMR (75.5 MHz, CDCl$_3$): δ [9.6 & 9.7], [12.5 & 12.8], [17.1 & 17.5], [19.4 & 19.5], 25.6, [28.0 & 28.1], 32.4, 35.8, 43.0, 44.3, [50.2 & 50.3], 54.3, [54.8 & 55.0 & 55.2 & 55.5], [55.6 & 55.7 & 55.9 & 56.0], 81.7, 82.8, 98.4, 106.9, [112.4 & 112.5], 113.7, 115.0, 115.2, 115.9, 116.3, 118.4, [123.0 & 123.1], [127.7 & 127.8], 128.8, 128.9, 129.5, 130.1, [134.1 & 134.2], 142.6, 149.1, 149.4, 153.4, 158.9, [161.4 & 161.6], [163.2 & 163.5], 170.9, [171.3 & 171.5], 172.3. MALDI-TOF m/z 831.62 [(M+Na)$^+$ calcd for C$_{46}$H$_{56}$N$_4$NaO$_9{}^+$ 831.39].

Example 18

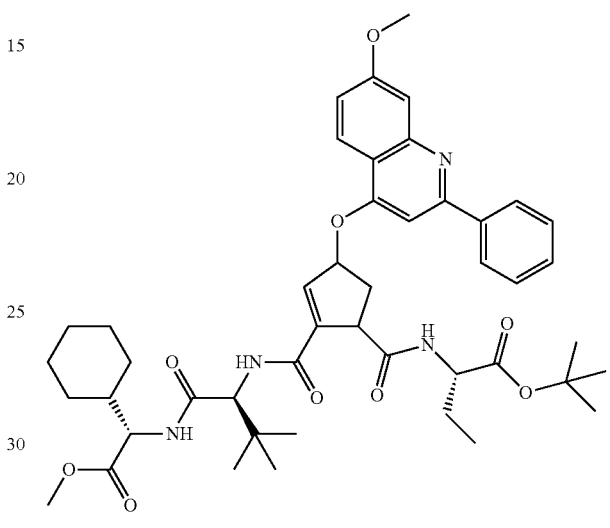

(S)-2-{[((1R,4R) &(1S,4S))-2-{(S)-1-[((S)-Cyclo-hexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-butyric add tert-butyl ester (18)

Compound 18 (16.1 mg, 26%) was prepared from 12 (43.2 mg, 0.077 mmol) according to the method for the preparation of 14 using (2-amino-3,3-dimethyl-butyrylamino)-cyclohexyl-acetic acid methyl ester instead of (2-amino-3-methyl-butyrylamino)-cyclohexyl acetic acid methyl ester. Flash column chromatography was performed in toluene/ethyl acetate 3:1 instead of 6:1: This gave the title compound as a white powder.

$^1$H-NMR (300 MHz, CDCl$_3$): δ 0.77-0.83 (m, 3H), [(0.92 & 0.93) s, 9H] 0.94-1.20 (m, 4H), [(1.36 & 1.38) s, 9H], 1.42-1.76 (m, 8H), 2.20-2.38 (m, 1H), 2.81-2.96 (m, 1H), 3.20-3.22 (m, 1H), 2.78 (s, 3H), [(3.83 & 3.85) a, 3H], 3.97-4.02 (m, 1H), 4.17-4.21 (m, 1H), 4.22-4.37 (m, 2H), 5.85-5.97 (m, 1H), [6.76-6.78 (m, 0.5H)], [6.80-6.82 (m, 0.5H)], 6.98-7.05 (m, 3H), 7.23-7.41 (m, 8H), 7.82-7.99 (m, 3H). $^{13}$C-NMR (75.5 MHz, CDCl$_3$): δ [9.4 & 9.5], [25.4 & 25.5], 25.8, [26.5 & 26.6], [27.9 & 28.0], [28.4 & 28.51], 29.3, [35.4 & 35.7], [36.0 & 36.4], [40.5 & 40.7], [50.2 & 50.5), [52.1 & 52.2], 154.1 & 54.3], 55.5, [57.0 & 57.3], [60.4 & 60.7], [81.8 & 82.0], [82.4 & 82.5] 98.1, 107.5, 115.0, 118.1, 123.0, 127.5, 128.7, 128.8, 129.2, 134.9, 135.8, 141.9, 142.5, 151.3, 159A, [160.9 & 161.3], [163.7 & 163.9], [169.9 & 170.0] [170.0 & 171.3], [172.5 & 172.4]. MALDI-TOF m/z 835.68 [(M+Na)$^+$ calcd for C$_{46}$H$_{60}$N$_4$NaO$_9{}^+$ 835.43].

Example 19

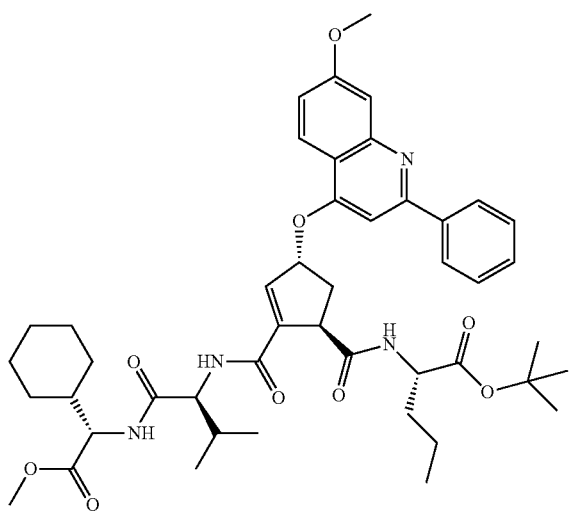 [SMILES: CC[C@H](NC(=O)C1CC(Oc2cc(-c3ccccc3)nc3cc(OC)ccc23)C=C1C(=O)N[C@H](C(=O)N[C@H](C(=O)OC)C1CCCCC1)C(C)(C)C)C(=O)OC(C)(C)C]

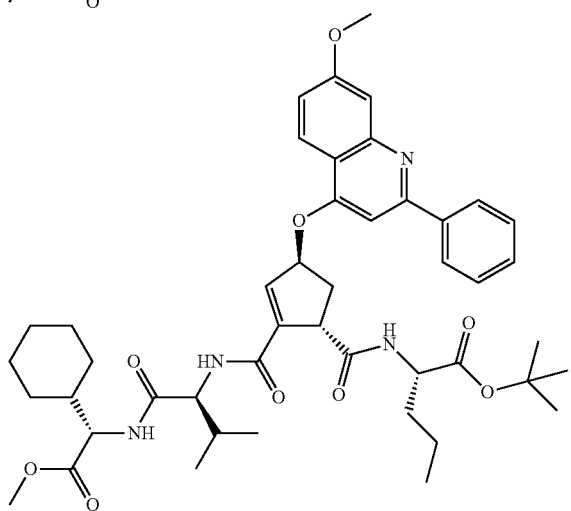

(S)-2-{[(1R,4R)-2-{(S)-1-[((S)-Cyclohexyl-ethoxy-carbonyl-methyl)-carbamoyl]-2-methy-propylcarbamoyl}-4-(7-methoxy-2-phenyl-quinolin-4-yloxy)-cyclopent-2-enecarbonyl]-amino)-pentanoic acid tert-butyl ester (19a) and (S)-2-{[(1 S,4S)-2-((S)-1-[((S)-Cyclohexyl-methoxycarbonyl-methyl)-carbamoyl]-2-methyl-propylcarbamoyl}(7-methoxy-2-phenyl-quinolin-4-yloxy)-cyclopent-2-enecarbonyl]-amino}-pentanoic add tert-butyl eater (19b)

The add 11 (0.051 g, 0.087 mmol) and (2-amino-3-methyl-butyrylamino)-cyclohexyl-acetic acid methyl ester (0.054 g, 0.21 mmol) were dissolved in DMF (1.5 mL) and cooled in an ice-bath. DIPEA (16 mg, 0.12 mmol) and HATU (47 mg, 0.13 mmol) were added. After two and a half hours the mixture was co-concentrated with toluene and methanol and then purified by flash column chromatography (toluene/ethyl acetate 3:1). Further purification was performed on HPLC (90% MeOH+0.2% TEA). This gave after co-concentration the two diastereomers 19a (9.4 mg, 13%) and 19b (5.3 mg, 7%) as slightly yellow syrups. After lyophilisation 19a and 19b were collected as white powders:

$^1$H-NMR (300 MHz, CDCl$_3$): δ 0.86-0.93 (m, 3H), 0.94-1.00 (m, 6H), 1.00-1.41 (m, 7H), 1.46 (s, 9H), 1.50-1.88 (m, 8H), 2.05-2.20 (m, 1H), 2.20-2.37 (m, 1H), 3.12-3.25 (m, 1H), 3.73 (s, 3H), 3.97 (s, 3H), 4.05-4.20 (m, 1H), 4.40-4.55 (m, 3H), 6.02-6.18 (m, 1H), 6.30 (d, J=8.52 Hz, 1H), 6.63 (s, 1H), 6.76 (d, J=8.51 Hz, 1H), 7.08-7.18 (m, 2H), 7.42-7.56 (m, 5H), 8.00-8.12 (m, 3H); $^{13}$C-NMR (75.5 MHz, CD$_3$OD): δ 14.0, 18.4, 19.3, 26.1, 28.3, 28.5, 29.7, 31.9, 34.9, 36.0, 41.0, 50.7, 52.4, 53.3, 55.7, 57.2, 58.6, 82.0, 82.7, 98.4, 105.7, 107.7, 115.2, 118.4, 123.2, 125.3, 127.9, 129.0, 129.1, 135.1, 138.0, 142.4, 151.6, 159.4, 161.6, 164.3, 170.7, 171.2, 172.3. 19b: $^1$H-NMR (300 MHz, CDCl$_3$): δ 0.90-1.04 (m, 9H), 1.04-1.43 (m, 7H), 1.47 (s, 9H), 1.50-1.87 (m, 8H), 2.10-2.27 (m, 1H), 2.33-2.45 (m, 1H), 3.10-3.20 (m, 1H), 3.73 (s, 3H), 3.96 (s, 3H), 4.02-4.10 (m, 1H), 4.36-4.53 (m, 3H), 6.00-6.16 (m, 1H), 6.30 (d, J=8.52 Hz, 1H), 6.73 (s, 1H), 6.86 (d, J=7.96 Hz, 1H), 7.08-7.16 (m, 2H), 7.36-7.56 (m, 5H), 8.03-8.11 (m, 3H). $^{13}$C-NMR (75.5 MHz, CD$_3$OD): δ 14.0, 18.6, 19.2, 26.1, 28.2, 28.7, 29.7, 34.5, 36.1, 36.6, 40.8, 50.5, 52.4, 53.4, 55.7, 57.3, 59.1, 64.8, 82.3, 98.4, 105.8, 107.8, 115.3, 118.4, 123.2, 127.8, 129.0, 129.4, 135.2, 1422, 144.9, 151.0, 151.6, 159.2, 164.3, 164.3, 170.2, 171.6, 171.9

Example 20

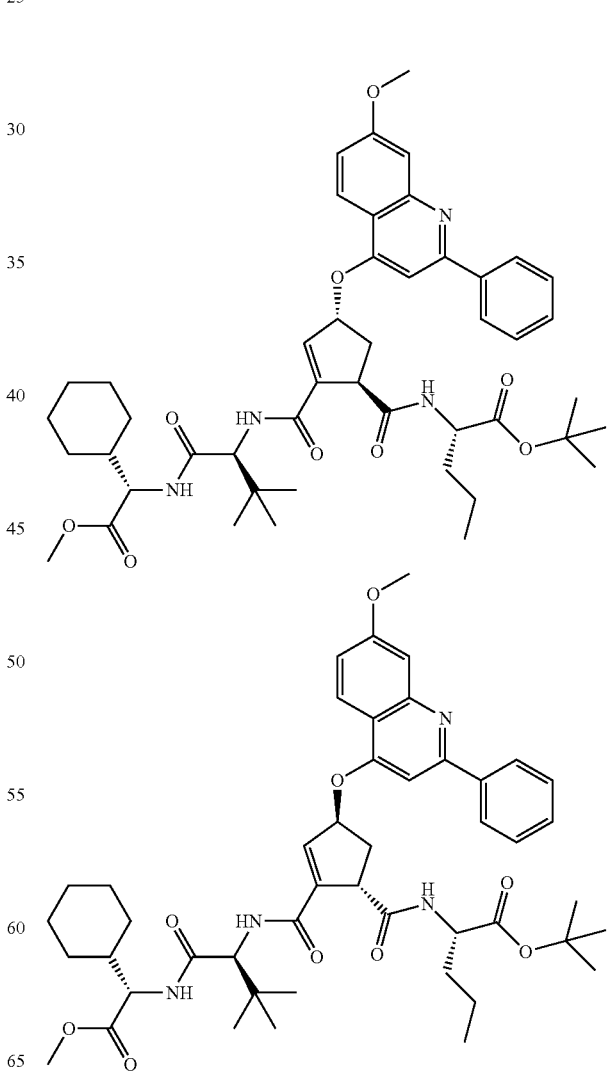

(S)-2-{[(1R,4R)-2-((R)-1-[((S)-Cyclohexyl-methoxycarbonyl-methy)-carbamoyl]2,2-dimethyl-propylcarbamoyl)-4-(7-methoxy-2-phenyl-quinolin-4-yloxy)-cyclopent-2-enecarbonyl]-amino}-pentanoic acid tert-butyl ester (20a) and (S)-2-{[(1 S,4S)-2-{(R)-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-pentanoic acid tert-butyl ester (20b)

Method A:

The carboxylic acid 11 (57 mg, 0.10 mmol) was dissolved in warm (50° C.) dry THF (2 mL). (2-Amino-3,3-dimethyl-butyrylamino)-cyclohexyl-acetic add methyl ester (50 mg, 0.12 mmol), DIPEA (30 mg, 0.23 mmol), DCC (25 mg, 0.12 mmol) and HOBt (17 mg, 13 mmol) were added. After two hours the mixture was concentrated and added to a short column (toluene/Ethyl acetate 1:3+3% AcOH). Then it was further purified on HPLC using 90% MeOH+0.2% TEA. The diastereomeric products were not separated. After HPLC the solution was co-concentrated with toluene and methanol to give 20 (28 mg, 34%).

Method B:

To an ice-cold solution of 11 (60 mg, 0.10 mmol) and (2-amino-3,3-dimethyl-butyrylamino)-cyclohexyl-acetic acid methyl ester (42 mg, 0.15 mmol) DIPEA (19 mg, 0.15 mmol) and HATU (62 mg, 0.16 mmol) were added. After two and a half hours the mixture was concentrated and purified using column chromatography. (toluene/Ethyl acetate 3:1). The diastereomeric mixture was separated using HPLC (90% MeOH+0.2% TEA). This gave 20a (6 mg, 6%) and 20b (9 mg, 10%).

20a: $^1$H-NMR (300 MHz, CDCl$_3$): δ 0.82-0.90 (m, 3H), 1.01 (s, 9H), 1.05-1.40 (m, 7H), 1.46 (s, 9H), 1.50-1.80 (m, 8H), 2.20-2.35 (m, 1H), 3.07-3.25 (m, 1H), 3.73 (s, 3H), 3.97 (s, 3H), 4.11 (d, J=7.96 Hz, 1H), 4.38-4.52 (m, 3H), 6.03-6.12 (m, 1H), 6.24 (d, J=8.79 Hz, 1H), 6.63 (s, 1H), 6.82 (d, J=9.06 Hz, 1H), 7.07-7.27 (m, 2H), 7.36 (d, J=7.96 Hz, 1H), 7.41-7.55 (m, 4H), 8.01-8.10 (m, 3H); $^{13}$C-NMR (75.5 MHz, CD$_3$OD): δ 14.0, 18.8, 26.1, 26.8, 28.2, 28.6, 29.6, 34.9, 35.6, 36.2, 40.9, 50.7, 52.4, 53.3, 55.7, 57.3, 60.8, 82.0, 82.7, 98.4, 105.2, 107.7, 115.2, 118.4, 123.2, 127.9, 129.0, 129.4, 131.1, 135.1, 138.4, 142.4, 153.3, 1569.6, 161.6, 164.2, 170.1, 171.3, 172.2. 20b: $^1$H-NMR (300 MHz, CDCl$_3$): δ 0.90-0.98 (m, 3H), 1.04 (s, 9H), 1.08-1.40 (m, 7H), 1.44 (s, 9H), 1.55-1.90 (m, 8H), 2.20-2.38 (m, 1H), 3.10-3.22 (m, 1H); 3.73 (s, 3H), 3.97 (s, 3H), 4.02-4.15 (m, 1H), 4.35-4.48 (m, 3H), 6.00-6.08 (m, 1H), 6.72 (s, 1H), 6.90 (d, J=9.06 Hz, 1H), 7.09-7.20 (m, 3H), 7.44-7.55 (m, 5H), 8.03-8.11 (m, 3H).

Example 21

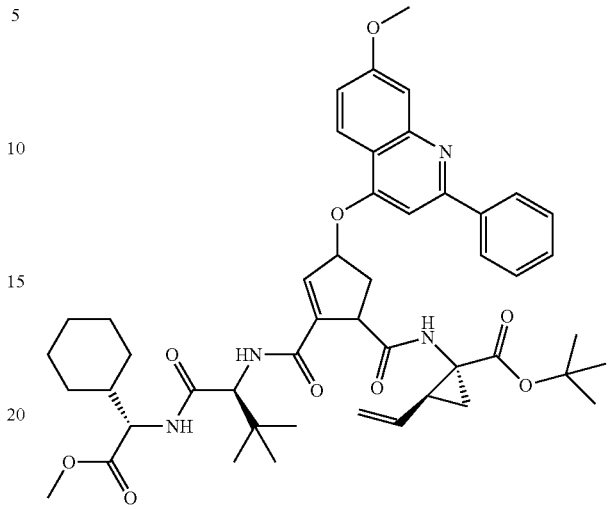

(1R,2S)-1-{[(((1R,4R) & (1 S,4S))-2-{(S)-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-2-vinyl-cyclopropanecarboxylic acid tert-butyl ester (21)

The acid 13 (35 mg, 0.060 mmol) and (2-amino-3,3-dimethyl-butyrylamino)-cyclohexyl-acetic acid methyl ester (22 mg, 0.080 mmol) were dissolved in dry THF (1.5 mL) and warmed to 50° C. HOBt (11 mg, 0.080 mmol) and DCC (31 mg, 0.15 mmol) were added. After one hour the mixture was co-concentrated with toluene and methanol and then purified by flash column chromatography (toluene/ethyl acetate 1:1). Further purification was performed on HPLC (80% MeOH+0.2% TEA. The diastereomeric mixture 21 was concentrated and gave a slightly yellow oil (26.4 mg, 53%). After lyophilisation 21 was collected as a white powder.

$^1$H-NMR (300 MHz, CDCl$_3$): δ [(0.98 & 1.00), s, 9H], 1.01-1.38 (m, 5H), [(1.39 & 1.40) s, 9H], 1.52-1.63 (m, 4H), 1.65-1.80 (m, 4H), 1.90-2.05 (m, 1H), 2.20-2.40 (m, 1H), 3.02-3.20 (m, 1H), [(3.66 & 3.67) s, 3H], 3.98 (s, 3H), 3.99-4.02 (m, 1H), 4.30-4.45 (m, 2H), 5.05-5.11 (m, 1H), 5.20-5.30 (m, 1H), 5.60-5.81 (m, 1H), 6.03-6.17 (m, 1H), 6.77-6.82 (m, 1H), 6.95-7.22 (m, 5H), 7.40-7.50 (m, 4H), 8.01-8.10 (m, 3H). $^{13}$C-NMR (75.5 MHz, CDCl$_3$): δ 22.3, [25.7 & 25.8], [26.4 & 26.5], [28.0 & 28.4] 29.2, 32.7, 33.3, [35.3 & 35.4], 36.0, [40.2 & 40.3], 40.7, 52.0, 55.4, [57.2 & 57.4] [60.4 & 60.5], [87.6 & 87.7], [82.3 & 82.5], 98.4, 107.0, 114.9, [117.4 & 117.5], 118.1, 122.9, 127.6, 128.8, 128.9, 129.2, [133.6 & 133.8], 135.9, 136.9, 140.1, [141.4 & 141.6], 151.1, 159.6, [160.9 & 161.3], [164.2 & 164.6], 168.9, 170.3, [172.1 & 172.6]. MALDI-TOF m/z 859.77 [(M+Na)$^+$ calcd for C$_{48}$H$_{60}$N$_4$NaO$_9^+$ 859.43].

Example 22

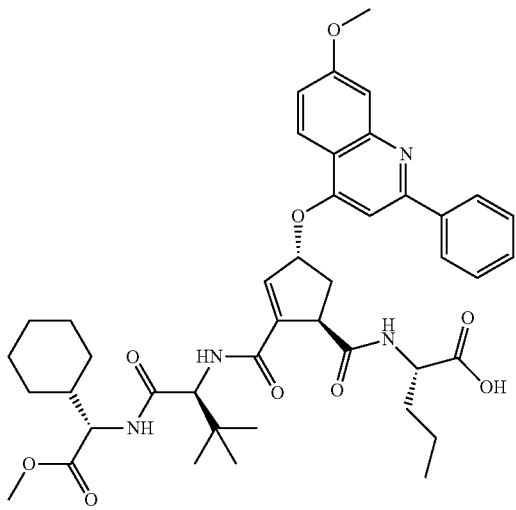

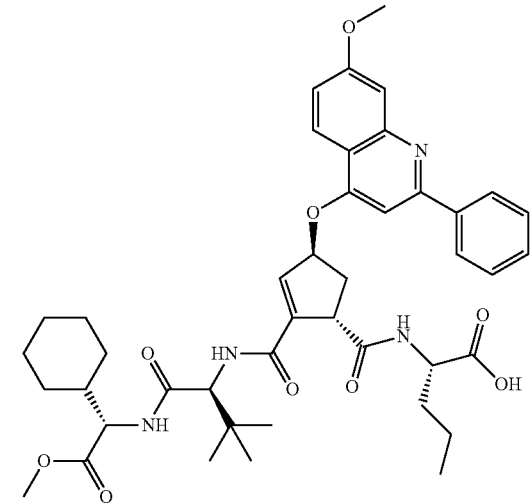

(S)-2-{[(1R,4R)-2-{(R)-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-pentanoic add (22a) and (S)-2-{[(1 S,4S)-2-{(R)-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-pentanoic acid (22b)

The tert.butyl ester 20 (28 mg, 0.034 mmol), TES (8.7 mg, 0.075 mmol), DCM (1 mL) and TFA (1 mL) were mixed in a round bottomed flask. Two hours later the mixture was concentrated and the diastereomers were separated on HPLC using 65% MeOH+0.2% TEA as mobile phase. This gave 22a (15 mg, 65%) and 22b (12 mg, 45%) as slightly yellow syrups. After lyophilisation the title compounds were collected as white powders.

22a: $[\alpha]^{22}D$ +155.8; $^1$H-NMR (300 MHz, CD$_3$OD): δ 0.90-0.97 (m, 3H), 1.03 (s, 9H), 1.05-1.50 (m, 7H), 1.50-1.80 (m, 8H), 2.43-2.55 (m, 1H), 2.77-2.90 (m, 1H), 3.68 (s, 3H), 3.96 (s, 3H), 4.20-4.30 (m, 2H), 4.31-4.40 (m, 1H), 4.45-4.50 (m, 1H), 6.03-6.11 (m, 1H), 6.98 (s, 1H), 7.12-7.19 (m, 1H), 7.36 (s, 1H), 7.41 (d, J=22 Hz, 1H), 7.50-7.60 (m, 3H), 8.03-8.10 (m, 3H): $^{13}$C-NMR (75.5 MHz, CD$_3$OD): δ 13.1, 19.1, 26.1, 28.7, 28.9, 29.5, 34.3, 34.8, 35.9, 40.1, 50.8, 51.2, 54.8, 55.0, 57.9, 60.7, 83.5, 99.1, 106.0, 115.2, 118.2, 123.3, 127.8, 128.0, 128.7, 128.8, 129.7, 135.2, 139.8, 143.7, 150.6, 160.1, 162.2, 165.2, 171.7, 172.2, 173.4. 22b: $[\alpha]^{22}D$ -72.3; $^1$H-NMR (300 MHz, CD$_3$OD): δ 0.90-0.97 (m, 3H), 1.02 (s, 9H), 1.07-1.35 (m, 7H), 1.53-1.90 (m, 8H), 2.46-2.61 (m, 1H), 2.76-2.88 (m, 1H), 3.69 (s, 3H), 3.96 (s, 3H), 4.15-4.35 (m, 2H), 4.37-4.41 (m, 1H), 4.42-4.47 (m, 1H), 6.02-6.12 (m, 1H), 7.02 (s, 1H), 7.16 (dd, J=2.47, 9.34 Hz, 1H), 7.32 (s, 1H), 7.40 (d, J=2.47 Hz, 1H), 7.48-7.58 (m, 3H), 8.03-8.12 (m, 3H); $^{13}$C-NMR (75.5 MHz, CD$_3$OD): δ 13.0, 18.8, 25.9, 26.0, 28.8, 29.4, 34.2, 34.8, 36.3, 39.9, 48.8, 50.5, 51.1, 54.8, 57.9, 60.5, 82.8, 99.0, 106.0, 115.1, 118.2, 123.1, 127.8, 127.9, 128.7, 129.0, 129.5, 136.7, 139.8, 142.8, 150.6, 160.1, 162.0, 162.2, 164.7, 172.1, 173.5.

Example 23

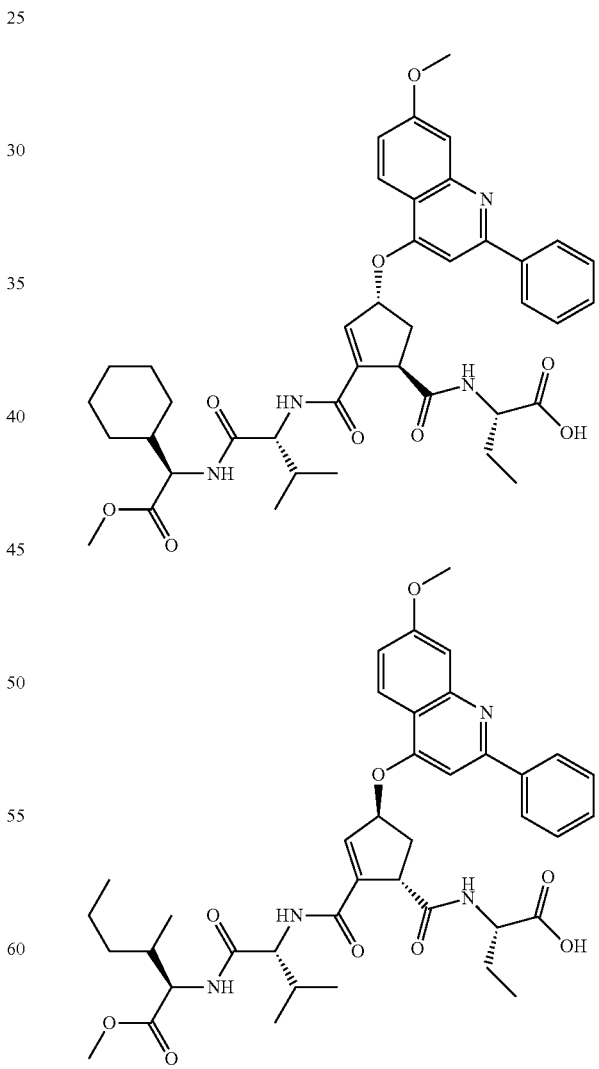

(S)-2-{[(1R,4R)-2-{(R)-1-[((R)-Cyclohexyl-methoxycarbonyl-methyl)-carbamoyl]-2-methy-propylcarbamoyl}-4-(7-methoxy-2-phenyl-quinolin-4-yloxy)-cyclopent-2-enecarbonyl]-amino}-butyric add (23a) and (S)-2-{[(1 S,4S)-2-{(R)-1-[((R)-Cyclohexyl-methoxycarbonyl-methyl)-carbamoyl]-2-methyl-propylcarbamoyl}-4-(7-methoxy-2-phenyl-quinolin-4-yloxy)-cyclopent-2-enecarbonyl]-amino}-butyric acid (23b)

Compound 23a (6.6 mg, 50%) and compound 23b (1.3 mg, 10%) were prepared from 15 (14 mg, 0.018 mmol) according to the method for the preparation of 22a and 22b. This gave the title compounds as white powders.

23a: $^1$H-NMR (300 MHz, CD$_3$OD): 0.88-1.02 (m, 9H), 1.02-1.40 (m, 7H), 1.55-1.97 (m, 6H), 2.01-2.10 (m, 1H), 2.38-2.52 (m, 1H), 2.88-3.00 (m, 1H), 3.77 (s, 3H), 3.98 (s, 3H), 4.08-4.20 (m, 1H), 4.22-4.40 (m, 3H). 6.03-6.18 (m, 1H), 6.86-6.99 (m, 1H), 7.08-7.20 (m, 1H), 7.23 (s, 1H), 7.40-7.43 (m, 1H), 7.45-7.70 (m, 3H), 8.02-8.20 (m, 3H). $^{13}$C-NMR (75.5 MHz, CD$_3$OD): δ 9.0, 17.6, 18.2, 24.5, 25.3, 28.1, 28.8, 30.9, 35.4, 39.4, 49.6, 51.1, 54.7, 572, 58.0, 82.4, 98.5, 105.5, 114.5, 117.7, 122.7, 127.2, 127.3, 128.2, 129.0, 135.6, 136.4, 141.7, 149.9, 159.5, 161.2, 161.4, 164.0, 171.0, 171.7, 172.4. 23b: $^1$H-NMR (300 MHz, CD$_3$OD): δ 0.9-1.20 (m, 9H), 1.21-1.53 (m, 7H), 1.55-1.93 (m, 6H), 2.05-2.20 (m, 1H), 2.41-2.50 (m, 1H), 2.96-3-05 (m, 1H), 3.77 (s, 3H), 4.00 (s, 3H), 4.05-4.40 (m, 4H), 6.05-6.18 (m, 1H), 6.90-6.95 (m, 1H), 7.05-7.22 (m, 2H), 7.50-7.65 (m, 4H), 8.01-8.16 (m, 3H).

Example 24

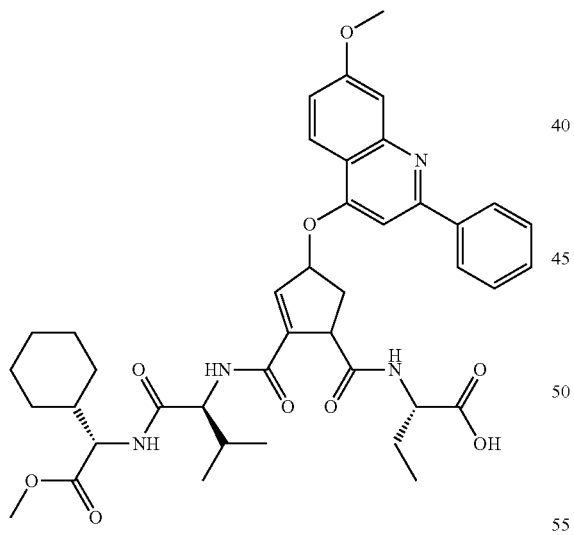

(S)-2-{[((1R,4R) & (1S,4S))-2-{((S)-1-[((S)-Carboxy-cyclohexyl-methyl)-carbamoyl]-2-methyl-propylcarbamoyl}-4-(7-methoxy-2-phenyl-quinolin-4-yloxy)-cyclopent-2-enecarbonyl]-amino}-butyric acid (24)

The tert.butyl ester 14 (13.4 mg, 0.017 mmol), TES (4.83 mg, 0.042 mmol), DCM (2 mL) and TFA (2 mL) were mixed n a round bottomed flask. One hour later the mixture was concentrated and purified by HPLC using 65% MeOH+ 0.2% TEA as mobile phase. This gave 24 (4.3 mg, 34%) as a slightly yellow syrup. After lyophilisation 24 was collected as a white powder.

$^1$H-NMR (300 MHz, CD$_3$OD): δ 0.91-0.99 (m, 9H), 1.00-1.28 (m, 4H), 1.65-1.78 (m, 9H), 1.92-1.95 (m, 1H), 2.00-2.05 (m, 1H), 2.93-3.01 (m, 1H), 3.75 (s, 3H), 3.97 (s, 3H), 4.10-4.40 (m, 4H), 6.05-6.15 (m, 1H), 6.88-6.94 (m, 1H), 7.05-7.10 (m, 2H), 7.41-7.43 (m, 1H), 7.44-7.55 (m, 2H), 8.62-8.68 (m, 1H), 8.69-8.79 (m, 1H), 7.97-8.05 (m, 2H). $^{13}$C-NMR (75.5 MHz, CD$_3$OD): δ 9.2, 18.5, 25.5, [29.0 & 29.2], [30.0 & 30.5], 35.3, 37.7, 39.7, 46.2, 50.0, [51.4 & 51.5], 53.6, 55.1, 57.1, 58.4, 83.1, 98.9, 104.9, 114.6, 118.3, 123.0, 123.4, 127.5, 128.4, 128.5, 129.7, 135.0, 142.1, 145.7, 1462, 159.2, 161.9, 164.3, 171.5, 171.9, 172.2. MALDI-TOF m/z 791.27 [(M+K)$^+$ calcd for C$_{42}$H$_{48}$KN$_4$O$_9^+$ 791.31].

Example 25

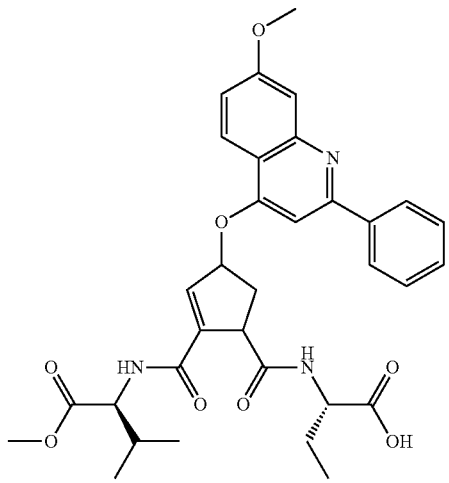 [SMILES: CC[C@H](NC(=O)C1CC(Oc2cc(-c3ccccc3)nc3cc(OC)ccc23)C=C1C(=O)N[C@H](C(=O)OC)C(C)C)C(=O)O]

(S)-2-{[((3R,5R) & (3S,5S))-5-((S)-1-Carboxy-propylcarbamoyl)-3-(7-methoxy-2-phenyl-quinolin-4-yloxy)-cyclopent-1-enecarbonyl]-amino}-3-methyl-butyric acid methyl ester (25)

Compound 25 (8.0 mg, 60%) was prepared from 18 (13.8 mg, 0.022 mmol) according to the method for the preparation of 24 which gave the title compound as a white powder.

$^1$H-NMR (300 MHz, CD$_3$OD): δ 0.83-1.02 (m, 9H), 1.88-1.80 (m, 1H), 1.82-2.02 (m, 1H), 2.10-2.22 (m, 1H), 2.40-2.60 (m, 1H), 2.81-2.95 (m, 1H), 3.75 (s, 3H), 4.00 (s, 3H), 4.18-4.22 (m, 1H), 4.27-4.40 (m, 2H), 6.05-6.12 (m, 1H), 6.99-7.02 (m, 1H), 7.16-7.21 (m, 1H), 7.38 (s, 1H), 7.40-7.43 (m, 1H), 7.48-7.61 (m, 3H), 7.98-8.12 (m, 3H).

Example 26

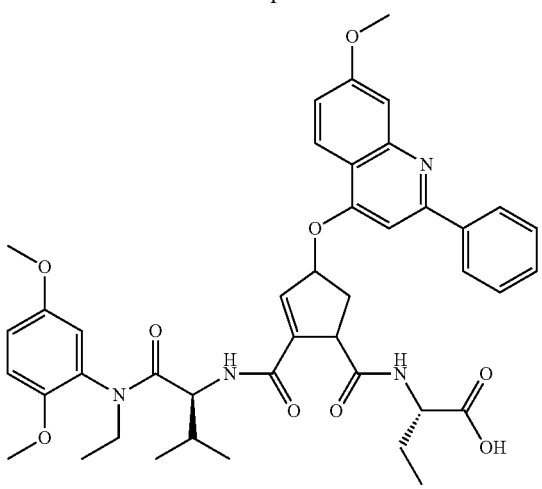

(S)-2-{[((1R,4R) &(1 S,4S))-2-{(S)-1-[(2,5-Dimethoxy-phenyl)-ethyl-carbamoyl]-2-methyl-propylcarbamoyl}4-(7-methoxy-2-phenyl-quinolin-4-yloxy)-cyclopent-2-enecarbonyl]-amino}-butyric add (26)

Compound 26 (5.7 mg, 36%) was prepared from 17 (16.7 mg, 0.021 mmol) according to the method for the preparation of 24 which gave the title compound as a white powder.
$^1$H-NMR (300 MHz, CD$_3$OD): δ 0.75-0.81 (m, 6H), 0.82-0.98 (m, 3H), 1.00-1.10 (m, 3H), 1.60-2.00 (m, 3H), 2.40-2.56 (m, 1H), 2.80-2.88 (m, 1H), 3.18-3.24 (m, 1H), 3.40-3.48 (m, 1H), [3.67-3.80 (m, 6H)], 3.97 (s, 3H), 4.10-4.20 (m, 1H), 4.21-4.40 (m, 2H), 6.02-8.17 (m, 1H), 6.75-6.82 (m, 1H), 6.84-7.01 (m, 3H), 7.10-720 (m, 1H), 7.30-7.37 (m, 1H), 7.40-7.43 (m, 1H), 7.50-7.60 (m, 3H), 8.00-8.17 (m, 3H). $^{13}$C-NMR (75.5 MHz, CD$_3$OD): δ 9.6, [11.8 & 12.0], [17.2 & 17.4], 18.9, 25.0, 32.3, 35.7, 43.3, 44.2, [50.3 & 50.5], [54.5 & 54.8 & 54.9 & 55.0], [55.1 & 55.2 & 55.3 & 58.0], 58.7, 83.6, 99.3, 105.5, [112.5 & 112.7], 114.3, [15.1 & 115.2], 115.7, 116.1, 118.4, [123.3 & 123.4], 125.2, [128.0 & 128.1, 128.8, 129.1, 129.8, [135.1 & 135.3], 139.2, (143.3 & 144.4], 149.2, [149.6 & 149.9], 153.8, 159.9, 162.4, [163.9 & 164.5], 172.1, 172.8, [173.6 & 173.7]. MALDI-TOF m/z 775.30 [(M+Na)$^+$ calcd for C$_{42}$H$_{48}$N$_4$NaO$_9$$^+$ 775.33].

Example 27

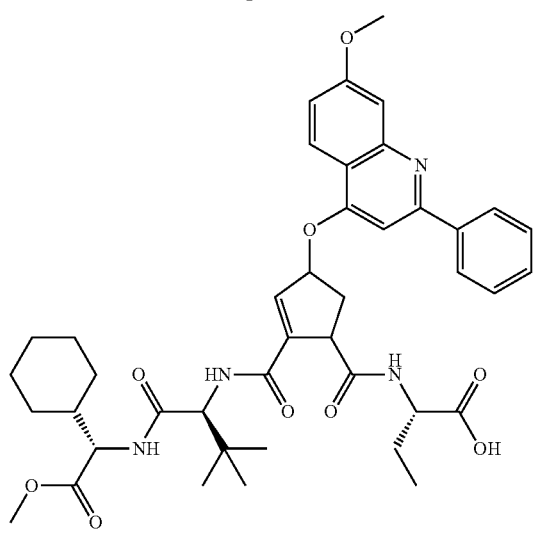

(S)-2-{[((1R,4R) &(1 S,4S))-2-{(S-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-butyric acid (27)

Compound 27 (6.0 mg, 72%) was prepared from 18 (8.6 mg, 0.011 mmol) according to the method for the preparation of 24. Purification by HPLC (60% methanol+0.2% TEA) gave the title compound as a white powder.
$^1$H-NMR (300 MHz, CD$_3$OD): δ 0.88-0.95 (m, 3H), 0.98 (s, 9H), 0.97-1.24 (m, 4H), 1.57-1.62 (m, 3H), 1.58-1.78 (m, 4H), 1.79-1.99 (m, 1H), 2.35-2.44 (m, 2H), 2.85-2.98 (m, 1H), [(3.67 & 3.69) 8, 3H], 3.94 (s, 3H), 4.10-4.20 (m, 1H), 4.30-4.40 (m, 3H), 6.00-6.09 (m, 1H), [6.80-6.82 (m, 0.5H)] [6.85-6.87 (m, 0.5H)], 7.05-7.19 (m, 2H), 7.38-7.55 (m, 4H), 7.95-8.07 (m, 3H). $^{13}$C-NMR (75.5 MHz, CD$_3$OD): δ [9.1 & 9.2], [24.7 & 24.9], [25.4 & 25.5], [25.9 & 26.0], [28.3 & 28.4], 28.9, [34.8 & 34.9], [35.6 & 35.9], [39.6 & 39.7], [49.9 & 50.13], [51.4 & 51.2], [53.9 & 54.0] 55.0. 157.2 & 57.4], 60.0, [82.1 & 82.5], 98.6, 106.2, 114.7, 117.8, 122.7, 127.5, 127.7, [128.4 & 128.5], 129.1, 135.3, 136.3, 141.6, 142.0, 150.5, 159.8, [161.0 & 161.3] [164.0 & 164.1], [171.6 & 171.9], [1722 & 172.3], [173.0 & 173.2]. MALDI-TOF m/z 779.43 [(M+Na)$^+$ calcd for C$_{42}$H$_{52}$N$_4$NaO$_9$$^+$ 779.36].

Example 28

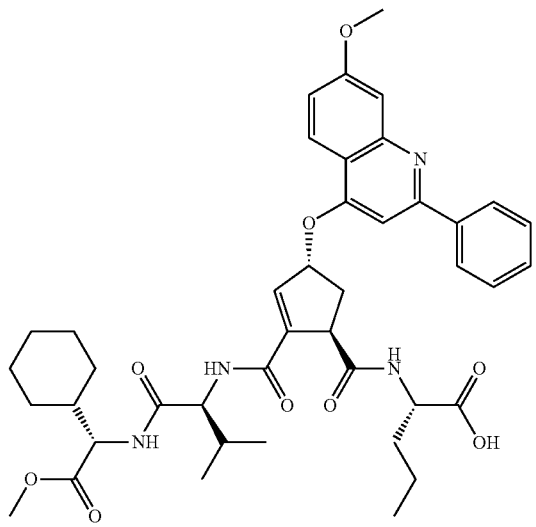 [SMILES: CCC[C@H](NC(=O)[C@@H]1C[C@@H](Oc2cc(-c3ccccc3)nc3cc(OC)ccc23)C=C1C(=O)N[C@H](C(=O)N[C@H](C(=O)OC)C1CCCCC1)C(C)C)C(=O)O]

(S)-2-{[(1R,4R)-2-{(S)-1-{((S)-Cyclohexyl-methoxycarbonyl-methyl)-carbamoyl}-2-methyl-propylcarbamoyl}-(7-methoxy-2-phenyl-quinolin-4-yloxy)-cyclopent-2-enecarbonyl]-amino}-pentanoic acid tert-butyl ester (28)

The tert.butyl ester 19a (7.6 mg, 0.0094 mmol) and TES (2.4 mg, 0.021 mmol) were dissolved in DCM (1 mL) and the mixture was cooled in an ice-bath. TFA (1 mL) was added. After two hours the mixture was concentrated and purified on HPLC using 60% MeOH+0.2% TEA as mobile phase. This gave 28 (6.1 mg, 86%) as a slightly yellow syrup. After lyophilisation the title compound was collected as white powder. $^1$H-NMR (300 MHz, CD$_3$OD+CDCl3

(1:1)): δ 0.90-1.00 (m, 9H), 1.00-1.30 (m, 7H), 1.50-1.90 (m, 8H), 2.00-2.10 (m, 1H), 2.40-2.50 (m, 1H), 2.85-2.98 (m, 1H), 3.65-3.72 (s, 3H), 3.99 (s, 3H), 4.15-4.22 (m, 1H), 4.24-4.35 (m, 2H), 4.38-4.44 (m, 1H), 6.10-6.20 (m, 1H), 6.95-6.96 (m, 1H), 7.16-7.23 (m, 1H), 7.31 (s, 1H), 7.42 (d, J=2.47 Hz, 1H), 7.53-7.72 (m, 3H), 7.97-8.16 (m, 3H); $^{13}$C-NMR (75.5 MHz, CD$_3$OD+CDCl$_3$ 1:1): δ 13.5, 18.3, 19.0, 26.0, 29.0, 29.7, 31.0, 34.1, 35.8, 40.2, 51.9, 55.9, 57.7, 58.9, 63.5, 68.4, 84.0, 99.6, 104.8, 105.7, 115.1, 119.0, 123.7, 128.1, 128.9, 129.1, 130.4, 131.3, 135.3, 138.0, 142.9, 159.5, 162.8, 164.8, 172.2, 172.2, 172.4

Example 29

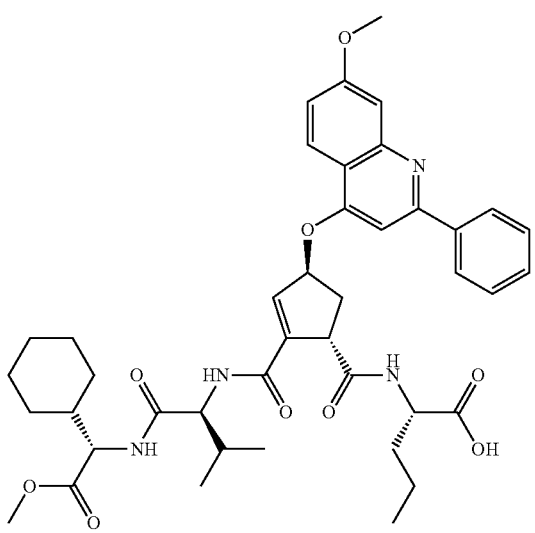 [SMILES: CCC[C@H](NC(=O)[C@H]1C[C@H](Oc2cc(-c3ccccc3)nc3cc(OC)ccc23)C=C1C(=O)N[C@H](C(=O)N[C@H](C(=O)OC)C1CCCCC1)C(C)C)C(=O)O]

(S)-2-{[(1 S,4S)-2-{(S)-1-[((S)-Cyclohexyl-methoxycarbonyl-methyl)-carbamoyl]-2-methyl-propylcarbamoyl}-methoxy-2-phenyl-quinolin-4-yloxy)-cyclopent-2-enecarbonyl]-amino}-pentanoic acid tert-butyl ester (29)

Compound 29 (1.3 mg, 28%) was prepared from 19b (5.3 mg, 0.065 mmol) according to the method for the preparation of 28. This gave the title compound as a white powder.

$^1$H-NMR (300 MHz, CD$_3$OD): δ 0.85-1.00 (m, 9H), 1.00-1.23 (m, 7H), 1.50-1.78 (m, 8H), 2.05-2.23 (m, 1H), 2.50-2.66 (m, 1H), 2.70-2.85 (m, 1H), 3.69 (s, 3H), 3.92 (s, 3H), 4.02-4.16 (m, 1H), 4.20-4.25 (m, 1H), 4.35-4.40 (m, 2H), 6.09 (m, 1H), 7.00 (s, 1H), 7.12-7.18 (dd, J=2.47, 2.19 Hz, 1H), 7.30 (s, 1H), 7.40 (d, J=2.42 Hz, 1H), 7.48-7.74 (m, 3H), 8.03-8.10 (m, 3H); $^{13}$C-NMR (75.5 MHz, CDCl$_3$): δ 11.7, 16.5, 17.0, 24.4, 27.2, 27.9, 29.0, 29.1 37.5, 41.8, 49.7, 50.5, 53.3, 56.3, 63.5, 66.5, 81.0, 100.3, 101.0, 105.7, 113.6, 121.6, 128.3, 127.1, 127.9, 130.1, 131.4, 135.6, 138.7, 141.1, 150.4, 160.2, 160.5, 165.3, 173.0, 173.6, 173.7

Example 30

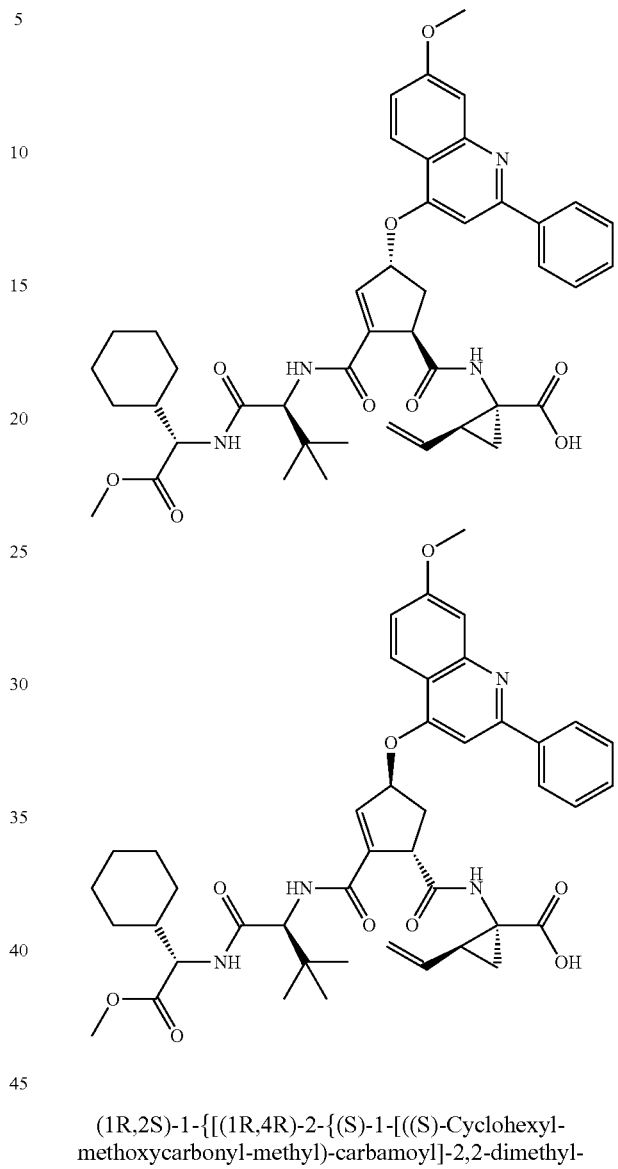

(1R,2S)-1-{[(1R,4R)-2-{(S)-1-[((S)-Cyclohexyl-methoxycarbonyl-methyl)-carbamoyl]-2,2-dimethyl-propylcarbamoyl}-4-(7-methoxy-2-phenyl-quinolin-4-yloxy)-cyclopent-2-enecarbonyl]-amino}-2-vinyl-cyclopropanecarboxylic acid (30a) and 1R,2S)-1-{[(1 S,4S)-2-{(S)-1-[((S)-Cyclohexyl-methoxycar-bonyl-methyl)-carbamoyl]-2,2-dimethyl-propylcar-bamoyl}-(7-methoxy-2-phenyl-quinolin-4-yloxy)-cyclopent-2-enecarbonyl]-amino}-2-vinyl-cyclopropane-carboxylic acid (30b)

Compound 30a (6.3 mg, 49%) and compound 30b (5.6 mg, 43%) were synthesized from 21 (13.8 mg, 0.0016 mmol) according to the method of the preparation of 22a and 22b. 30a and 30b: White powder.

30a: $^1$H-NMR (300 MHz, CD$_3$OD): δ 1.02 (s, 9H), 1.03-1.43 (m, 5H), 1.61-1.95 (m, 8H), 2.11-2.21 (m, 1H), 2.43-2.58 (m, 1H), 2.97-3.04 (m, 1H), 3.78 (s, 3H), 4.01 (s, 3H), 4.02-4.17 (m, 1H), 4.25-4.40 (m, 2H), 5.10-5-20 (m, 1H), 5.27-5.40 (m, 1H), 6.77-6.94 (m, 1H), 6.10-6.20 (m, 1H), 6.97 (s, 1H), 7.18 (dd, J=2.5, 92 Hz, 1H), 7.22 (s, 1H), 7.46 (d, J=2.5 Hz, 1H), 7.52-7.65 (m, 3H), 8.00-8.18 (m, 3H). $^{13}$C-NMR (75.5 MHz, CD$_3$OD): δ 13.5, 25.3, 25.7, 28.3, 28.7, 29.0, 32.8, 34.6, 35.3, 39.3, 49.7, 51.1, 54.6, 57.2, 59.8, 82.1, 98.4, 105.8, 114.5, 116.3, 117.6, 122.6, 127.2, 128.1, 128.2, 128.8, 130.2, 133.7, 136.0, 139.5, 141.5, 150.3, 159.7, 161.0, 1612, 163.4, 171.6, 172.5. MALDI-TOF m/z 803.56 [(M+Na)$^+$ calcd for C$_{44}$H$_{52}$N$_4$NaO$_9$$^+$ 803.36]. 30b: $^1$H-NMR (300 MHz, CD$_3$OD): δ 1.03 (s, 9H), 1.04-1.42 (m, 5H), 2.60-2.90 (m, 8H), 2.17-2.22 (m, 1H), 2.40-2.55 (m, 1H), 2.96-3.10 (m, 1H), 3.77 (s, 3H), 4.01 (s, 3H), 4.05-4.16 (m, 1H), 4.30-4.40 (m, 2H), 5.15-5.20 (m, 1H), 5.25-5.40 (m, 1H), 5.78-5.95 (m, 1H), 6.10-6.20 (m, 1H), 6.98 (s, 1H), 7.17 (dd, J=2.5, 9.1 Hz, 1H), 7.28 (s, 1H), 7.46 (d, J=2.5 Hz, 1H), 7.50-7.65 (m, 3H), 8.03-8.28 (m, 3H). $^{13}$C-NMR (75.5 MHz, CD$_3$OD): δ 13.7, 26.0, 26.3, 28.8, 29.4, 29.6, 34.0, 35.2, 35.8, 40.1, 50.6, 51.7, 55.3, 57.8, 80.6, 83.0, 99.1, 106.3, 115.2, 117.0, 118.3, 1232, 127.9, 128.0, 128.8, 129.6, 130.6, 134.4, 136.1, 140.0, 142.5, 150.8, 160.3, 161.8, 162.0, 165.7, 172.3, 173.0.

Example 31

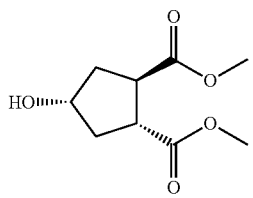

trans-(3R,4R)-Bis(methoxycarbonyl)cyclopentanol (31)

Sodium borohydride (1.11 g, 0.029 mol) was added to a stirred solution of (1R,2S)-4-oxo-cyclopentane 1,2-dicarboxylic add dimethyl ester (4.88 g, 0.0244 mol) in methanol (300 mL) at 0° C. After 1 h the reaction was quenched with 90 mL brine, concentrated and extracted with ethyl acetate. The organic phases were pooled, dried, filtered and concentrated. The crude product was purified by flash column chromatography (toluene/ethyl acetate 1:1) to give 31 (3.73 g, 76%) as a yellow oil.

Example 32

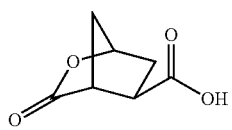 [SMILES: O=C(O)C1CC2CC1C(=O)O2]

3-Oxo-2-oxa-bicyclo[22.2.1]heptane-6-carboxylic acid (32)

Sodium hydroxide (1M, 74 ml, 0.074 mol) was added to a stirred solution of 31 (3.73 g, 0.018 mol) in methanol (105 mL) at room temperature. After 4 h, the reaction mixture was neutralized with 3M HCl, evaporated and co-evaporated with toluene several times. Pyridine (75 mL) and Ac$_2$O (53 mL) were added and the reaction mixture was allowed to shake overnight at room temperature. The mixture was then co-evaporated with toluene and purified by flash column chromatography (ethyl acetate+1% acetic acid) to give 32 (2.51 g, 88%) as a yellow oil.

Example 33

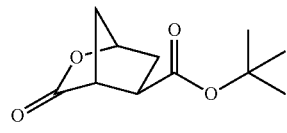

3-Ox-2-oxa-bicyclo[2.2.1]heptane-5-carboxylic acid tert-butyl ester (33)

DMAP (14 mg, 0.115 mmol) and Boc$_2$O (252 mg, 1.44 mmol) was added to a stirred solution of 32 (180 mg, 1.15 mmol) in 2 mL CH$_2$Cl$_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) to give 33 (124 mg, 51%) as white crystals.
$^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 48.1, 81.1, 81.6, 172.0, 177.7.

Example 34

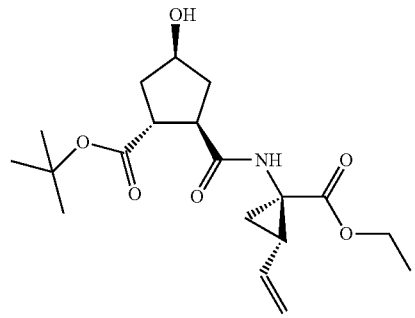 [SMILES: C=C[C@@H]1C[C@]1(NC(=O)[C@@H]1C[C@H](O)C[C@H]1C(=O)OC(C)(C)C)C(=O)OCC]

(1R,2R,4S)-2-((1R,2S)-1-Ethoxycarbonyl-2-vinyl-cyclopropylcarbamoyl)-4-hydroxy-cyclopentanecarboxylic acid tort-butyl ester (34)

Compound 33 (56 mg, 0.264 mmol) was dissolved in dioxane/water 1:1 (5 mL) and the mixture was cooled to 0° C. 1 M lithium hydroxide (0.62 mL, 0.520 mmol) was added and the mixture was stirred at 0° C. for 45 minutes, after which the mixture was neutralized with 1M hydrochloric acid and evaporated and coevaporated with toluene. The residue was dissolved in DMF (5 mL) and (1R,2S)-1-amino-2-vinylcyclopropane carboxylic acid ethyl ester hydrochloride (60 mg, 0.313 mmol) and diisopropylethylamine (DIEA) (138 □L, 0.792 mmol) were added and the solution was cooled to 0° C. HATU (120 mg, 0.316 mmol) was added and the mixture was stirred for 0.5 h at 0° C. and for an additional 2 h at room temperature. The mixture was then evaporated and extracted with EtOAc, washed with brine, dried, filtered and concentrated. Purification by flash column chromatography (toluene/EtOAc 1:1) provided compound 34 (86 mg, 89%) as a colorless oil.

Example 35

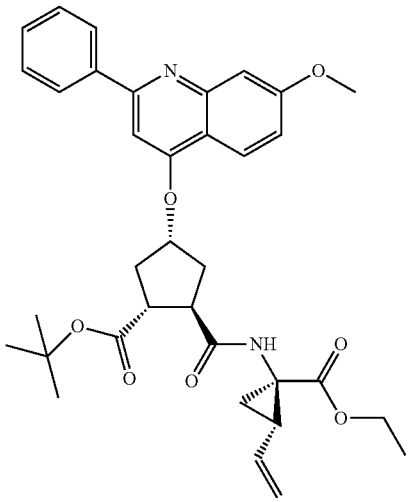 [SMILES: C=C[C@@H]1C[C@]1(NC(=O)[C@@H]1C[C@@H](Oc2cc(-c3ccccc3)nc3cc(OC)ccc23)C[C@H]1C(=O)OC(C)(C)C)C(=O)OCC]

(1R,2R,4R)-2-((1R,2S)-1-Ethoxycarbonyl-2-vinyl-cyclopropylcarbamoyl)-4-(7-methoxy-2-phenyl-quinolin-4-yloxy)-cyclopentanecarboxylic acid tert-butyl ester (35)

Compound 34 (73 mg, 0.199 mmol) was dissolved in dry THF (4 mL) and 2-phenyl-7-methoxy-4-quinolinol (88 mg, 0.342 mmol) and triphenylphosphine (141 mg, 0.538 mmol) were added. The mixture was cooled to 0° C. and DIAD (0.567 mmol) dissolved in 1 mL THF was added dropwise. The mixture was stirred for 48 h at room temperature. The solvent was evaporated and the crude product was purified by flash column chromatography gradient elution (toluene/EtOAc 9:1, 6:1, 4:1) to give compound 35 (81 mg, 68%).

Example 36

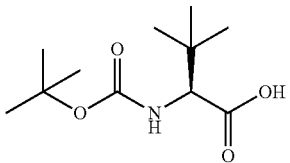 [SMILES: CC(C)(C)OC(=O)N[C@H](C(=O)O)C(C)(C)C]

Boc-L-ter-leucine-OH (38)

Triethylamine (890 uL, 6.40 mmol) was added dropwise to a stirred solution of L-tert-leucine (300 mg, 2.29 mmol) and di-tert-butyl dicarbonate (599 mg, 2.74 mmol) in dioxane/water 1:1 (8 mL) and the solution was stirred overnight. The mixture was extracted with petroleum ether (2×) and the aqueous phase was cooled to 0° C. and carefully acidified to pH 3 by slow addition of 4M $NaHSO_4.H_2O$. The acidified water phase was extracted with EtOAc (3×) and the combined organic phases were washed with brine (2×) and was then dried, filtered and concentrated to give compound 36 (522 mg, 99%) as a colorless powder. No further purification was needed. $^1$H-NMR (300 MHz, $CD_3OD$) δ 0.99 (s, 9H), 1.44 (s, 9H), 3.96 (s, 1H); $^{13}$C-NMR (75.5 MHz, $CD_3OD$) δ 27.1, 28.7, 34.9, 68.0, 80.5, 157.8, 174.7.

Example 37

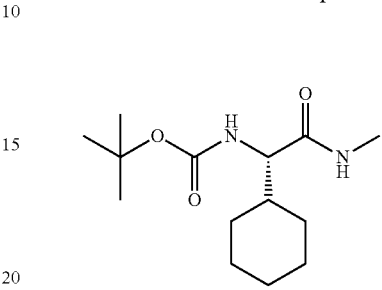

((S)-Cyclohexyl-methylcarbamoyl-methy)-carbamic acid tert-butyl ester (37)

Boc-Chg-OH (387 mg, 1.50 mmol) was coupled to methylamine hydrochloride (111 mg, 1.65 mmol) using the same HATU coupling conditions as in the synthesis of compound 34. The crude product was extracted with EtOAc, washed with brine and concentrated. Purification by flash column chromatography (EtOAc) provided compound 37 (307 mg, 76%) as a colorless solid.
$^1$H-NMR (300 MHz, $CDCl_3$) δ 0.91-1.13 (m, 2H), 1.14-1.31 (m, 3H), 1.44 (s, 9H), 1.61-1.80 (m, 6H), 2.80 (d, J=4.7 Hz, 3H), 3.91 (dd, J=7.1, 9.1 Hz, 1H), 5.23 (b, 1H), 6.52 (be, 1H); $^{13}$C-NMR (75.5 MHz, $CDCl_3$) δ 25.9, 28.0, 26.1, 28.3, 28.5, 29.6, 40.5, 59.5, 79.7, 155.9, 172.4.

Example 38

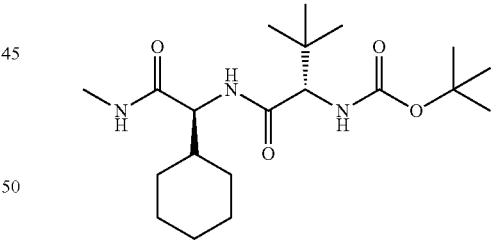

{(S)-1-[((S)-Cyclohexyl-methylcarbamoyl-methyl)-carbamoyl]-2,2-dimethyl-propyl}-carbamic add tert-butyl ester (38)

To a solution of compound 37 (98 mg, 0.362 mmol) in methylene chloride (3 mL) were added triethylsilane (115 mL, 0.742 mmol) and TFA (3 mL). The mixture was stirred for 2 h at room temperature and was then evaporated and coevaporated with toluene. The deprotected amine was dissolved in DMF (5 mL) and coupled to compound 36 (84 mg, 0.363 mmol) using the same HATU coupling conditions as in the synthesis of 34. The crude product was extracted with EtOAc, washed with brine, dried, filtered and concentrated. Purification by flash column chromatography (toluene/EtOAc 1:1) provided compound 38 (128 mg, 92%) as a colorless solid.

$^1$H-NMR (300 MHz, CDCl$_3$) δ 0.99 (s, 9H), 1.02-1.30 (m, 5H), 1.44 (s, 9H), 1.58-1.77 (m, 4H), 1.78-1.89 (m, 2H), 2.79 (d, J=4.7 Hz, 3H), 4.11 (d, J=9.3 Hz, 1H), 4.33 (app. t, J, 8.5 Hz, 1H), 5.65 (b, 1H), 7.25 (b, 1H), 7.39 (b, 1H); $^{13}$C-NMR (75.5 MHz, CDCl$_3$) δ 25.9, 25.9, 26.0, 26.2, 26.8, 28.4, 29.0, 29.7, 34.5, 39.7, 58.4, 62.4, 79.4, 156.0, 171.4, 171.8.

Example 39

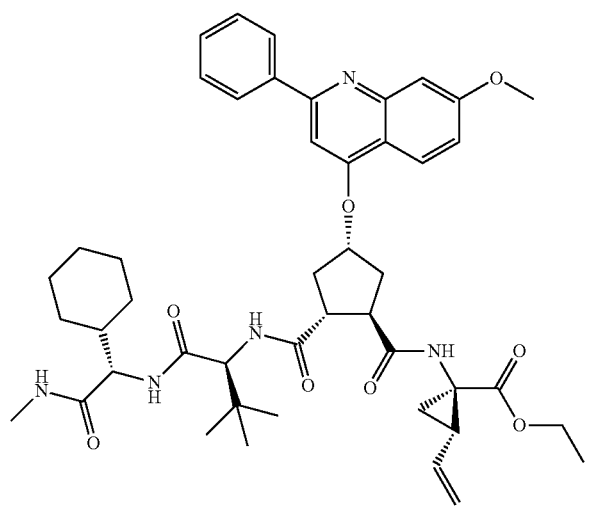 [SMILES: C=C[C@@H]1C[C@]1(NC(=O)[C@@H]1C[C@@H](Oc2cc(-c3ccccc3)nc3cc(OC)ccc23)C[C@H]1C(=O)N[C@H](C(=O)N[C@H](C(=O)NC)C1CCCCC1)C(C)(C)C)C(=O)OCC]

(1R,2S)-1-{[(1R,2R,4S)-2-{(S)-1-[((S)-Cyclohexyl-methylcarbamoyl-methyl)-carbamoyl]-2,2-diethyl-propylcarbamoyl}-4-(7-methoxy-2-phenyl-quinolin-4-yloxy)-cyclopentanecarbonyl]-amino}-2-vinyl-cyclopropanecarboxylic acid ethyl ester (39)

To a solution of compound 35 (30 mg, 0.050 mmol) in methylene chloride (1.5 mL) were added triethylsilane (21 □L, 0.132 mmol) and TFA (1.5 ml). The mixture was stirred for 2 h at room temperature and was then evaporated and coevaporated with toluene. The amine 38 (1.3 eq) was deprotected in the same manner as compound 35 and was then coupled to deprotected compound 35 using the same HATU coupling conditions as in the synthesis of 34. The crude product was extracted with EtOAc, washed with brine, dried, filtered and concentrated. Purification using HPLC (MeOH/water 9.1+0.2% triethylamine) provided compound 39 (30 mg, 74%) as a colorless sold.

$^1$H-NMR (300 MHz, CD$_3$OD) δ 0.81-1.14 (m, 4H), 0.99 (s, overlapped, 9H), 1.21 (t, J 7.1 Hz, 3H), 1.35-1.51 (m, 4H), 1.52-1.65 (m, 3H), 1.66-1.72 (m, 2H), 2.03-2.20 (m, 2H), 2.24-2.39 (m, 1H), 2.46-2.56 (m, 1H), 2.66 (s, 3H), 2.72-2.85 (m, 1H), 3.39-3.48 (m, 2H), 3.90 (s, 3H), 4.03-4.15 (m, 3H), 4.44 (s, 1H), 5.09 (dd, J=1.9, 10.3 Hz, 1H), 5.19-5.27 (m, 1H), 5.25 (dd, overlapped, 1H), 5.79 (ddd, J=8.8, 10.3, 17.2 Hz, 1H), 8.99 (s, 1H), 7.07 (dd, J=2.5, 9.1, Hz, 1H), 7.29 (d, J=2.5 Hz, 1H), 7.43-7.52 (m, 3H), 7.86-7.98 (m, 2H), 8.05 (d, J=9.3 Hz, 1H); $^{13}$C-NMR (75.5 MHz, CD$_3$OD) δ14.7, 23.4, 28.0, 26.9, 27.1, 27.3, 30.1, 30.7, 35.0, 35.4, 38.3, 38.8, 40.9, 41.0, 47.9, 55.9, 59.6, 62.0, 62.4, 79.8, 99.9, 107.3, 116.4, 118.0, 119.1, 124.4, 128.9, 129.8, 130.5, 135.3, 141.3, 152.1, 161.1, 162.4, 163.0, 171.6, 172.5, 173.7, 175.2, 176.8. Maldi-TOF-spectrum: (M+H)$^+$ calcd: 810.4, found: 810.5; (M+Na)$^+$ calcd: 832.4, found: 832.4; (M+K)$^+$ calcd: 848.5, found: 848.4.

Example 40

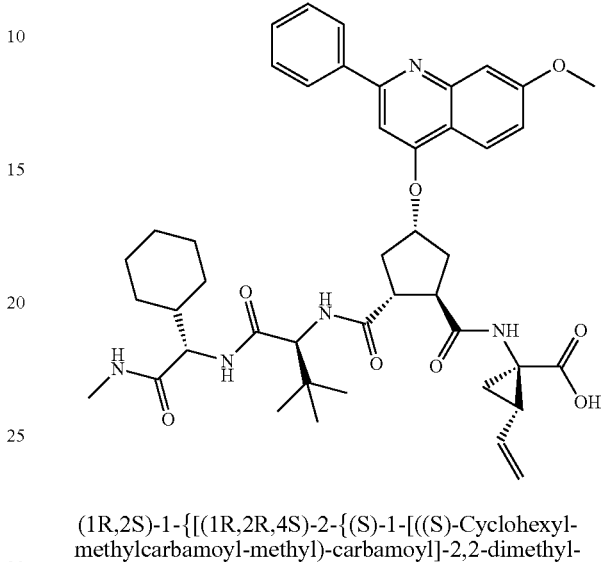

(1R,2S)-1-{[(1R,2R,4S)-2-{(S)-1-[((S)-Cyclohexyl-methylcarbamoyl-methyl)-carbamoyl]-2,2-dimethyl-propylcarbamoyl}-4-(7-methoxy-2-phenyl-quinolin-4-yloxy)-cyclopentanecarbonyl]-amino}-2-vinyl-cyclopropanecarboxylic acid (40)

To a solution of compound 39 (20 mg, 0.025 mmol) in THF/MeOH/water 2:1:1 (2 mL) at 0° C. was added 1M LiOH (175 uL, 0.175 mmol) and the solution was allowed to attain room temperature and was stirred for 48 h. The solution was acidified to pH 3 with 1M HCl and was then evaporated and coevaporated with toluene. The crude product was purified by HPLC (MeOH/water 6:4+0.5% TFA followed by MeOH/water 4:1+0.2% TFA) to give compound 40 (13 mg, 67%) as a colorless solid. $^1$H-NMR (300 MHz, CD$_3$OD) δ 0.82-0.98 (m, 1H), 1.01 (s, 9H), 1.05-1.26 (m, 3H), 1.34-1.43 (m, 1H), 1.49-1.77 (m, 8H), 2.10-2.21 (m, 1H), 2.28-2.42 (m, 2H), 2.50-2.61 (m, 1H), 2.64 (s, 3H), 2.68-2.81 (m, 1H), 3.36-3.45 (m, 2H), 4.04-4.11 (m, 1H), 4.06 (s, overlapped, 3H), 4.27 (d, J=8.8 Hz, 1H), 5.10 (dd, J=1.8, 10.3 Hz, 1H), 5.28 (dd, J=1.8, 17.2 Hz, 1H), 5.59-5.68 (m, 1H), 5.82 (ddd, J=9.1, 10.3, 17.2 Hz, 1H), 7.44 (dd, J=2.5, 11.8 Hz, 1H), 7.50 (s, 1H), 7.53 (d, J=2.5 Hz, 1H), 7.69-7.78 (m, 3H), 8.02-8.07 (m, 2H), 8.39 (d, J=9.3 Hz, 1H); $^{13}$C-NMR (75.5 MHz, CD$_3$OD) δ 23.5, 26.0, 26.9, 27.2, 27.3, 30.0, 30.7, 34.7, 35.3, 37.0, 38.7, 41.0, 41.3, 47.4, 56.9, 59.4, 62.7, 83.9, 100.4, 1022, 1162, 117.7, 121.7, 126.7, 129.8, 130.8, 133.4, 133.9, 135.6, 143.5, 158.0, 166.6, 168.6, 172.5, 173.4, 173.6, 175.4, 176.4. Maldi-TOF-spectrum: (M+H)$^+$ calcd: 782.4, found: 782.2; (M+Na)$^+$ calcd: 804.4, found: 804.2; (M+K)$^+$ calcd: 820.5, found: 820.2.

Example 41

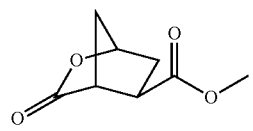

3-Oxo-2-oxa-bicyclo[2.2.1]heptane-5-carboxylic acid meth ester (41)

Compound 32 (1.014 g, 6.50 mmol) was dissolved in acetone (35 mL) before methyl Iodide (13.68 g, 96.4 mmol) and sliver(I)oxide (1.61 g, 6.95 mmol) were added. After stirring for 3 h the mixture was filtered through celite and the filtrate was evaporated before purification by flash column chromatography (toluene/ethyl acetate 4:1) was performed yielding the methyl ester 41 (702 mg, 64%) as white crystals. $^1$H-NMR (300 MHz, CDCl$_3$): δ 1.96 (d, J=10.7 Hz, 1H), 2.21-2.25 (m, 3H), 2.91-2.95 (m, 1H), 3.16 (s, 1H), 3.75 (s, 3H), 4.98 (app. s, 1H).

Example 42

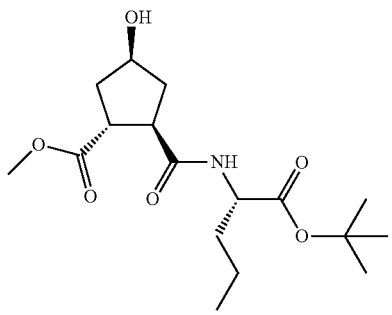 [SMILES: CCC[C@H](NC(=O)[C@@H]1C[C@H](O)C[C@H]1C(=O)OC)C(=O)OC(C)(C)C]

(1R,2R,4S)-2-((S)-1-tert-Butoxycarbonyl-butylcarbamoyl)-4-hydroxy-cyclopentanecarboxylic acid methyl ester (42)

Compound 41 (263 mg, 1.55 mmol) and H-Nva-OtBu (420 mg, 2.42 mmol) were dissolved in dry THF (20 mL). DIEA (530 uL, 3.04 mmol) and 2-hydroxypyridine (260 mg, 2.73 mmol) were added and the mixture was refluxed for five days. The solvent was evaporated and the crude product was purified by flash column chromatography (toluene/EtOAc 1:2) to give 42 (510 mg, 96%).

Example 43

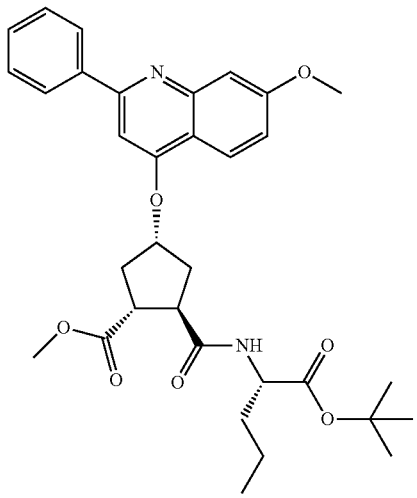 [SMILES: CCC[C@H](NC(=O)[C@@H]1C[C@@H](Oc2cc(-c3ccccc3)nc3cc(OC)ccc23)C[C@H]1C(=O)OC)C(=O)OC(C)(C)C]

(1R,2R,4R)-2-((S)-1-tert-Butoxycarbonyl-butylcarbamoyl)-4-(7-methoxy-2-phenyl quinolin-4-yloxy)-cyclopentanecarboxylic acid methyl eater (43)

Compound 42 (249 mg, 0.725 mmol), 2-phenyl-7-methoxy-4-quinolinol (310 mg, 1.23 mmol) and PPh$_3$ (580 mg, 2.21 mmol) were dissolved in dry THF and the temperature was lowered to 0° C. DIAD (435 uL 2.21 mmol) dissolved in 2 mL dry THF, was added to the mixture during five minutes. After two hours the temperature was raised to room temperature and the solution was stirred overnight. Evaporation and purification by flash column chromatography (toluene/EtOAc gradient 6:1 to 4:1) gave 43 (324 mg, 78%).

Example 44

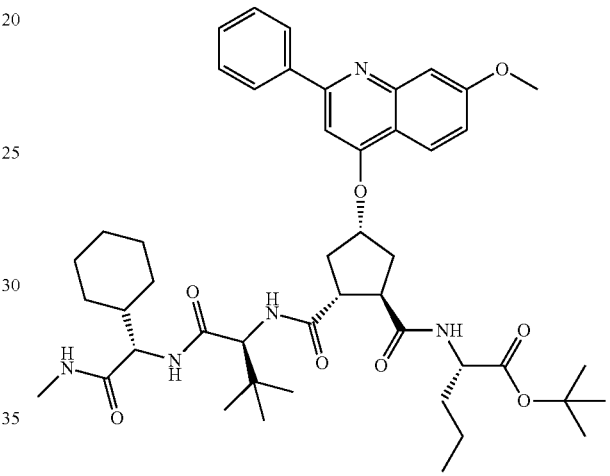

(S)-2-{[(1R,2R,4S)-2-{(S)-1-[((S)-Cyclohexyl-methylcarbamoyl-methyl)-carbamoyl]-2,2-dimethyl-propylcarbamoyl}-4-(7-methoxy-2-phenyl-quinolin-4-yloxy)-cyclopentanecarbonyl]-amino}-pentanoic acid tert-butyl ester (44)

Compound 43 (38 mg, 0.066 mmol) was dissolved in dioxane/water 1:1 (4 mL) and the solution was cooled to 0° C. and 1 M LiOH (132 ul, 0.132 mmol) was added. The temperature was raised to room temperature and the solution was stirred for 2 hours after which it was neutralized by addition of M HCl and evaporated and coevaporated with toluene. The residue and deprotected amine 38 (1.1 eq) was dissolved in DMF and coupled using the standard HATU coupling conditions as in the synthesis of compound 34. The crude product was extracted with EtOAc, washed with brine, dried, filtered and concentrated. Purification with HPLC (MeOH/water 9:1+0.2% TEA) provided compound 44 (44 mg, 81%) as a colorless solid.

$^1$H-NMR (CDCl$_3$, 300 MHz) rotamers (5:1) δ 0.79 (t, J=7.3 Hz, 3H), 0.85-1.19 (m, 3H), 0.93 (s, overlapped, 9H), 1.20-1.35 (m, 2H), 1.39 (s, 1.5H), 1.43 (s, 7.5H), 1.54-1.79 (m, 6H), 2.06-2.28 (m, 3H), 2.39-2.51 (m, 2H), 2.66-2.78 (m, 1H), 2.74 (d, overlapped, J=4.7 Hz, 3H), 3.42-3.68 (m, 2H), 3.84 (s, 2.5H), 3.88 (s, 0.5H), 4.19 (t, J=8.9 Hz, 1H), 4.39-4.59 (m, 1H), 4.68 (d, J=9.6 Hz, 1H), 5.04-5.14 (m, 1H), 6.77 (s, 1H), 6.88-7.06 (m, 2H), 7.26-7.47 (m, 6H), 7.53 (b, 1H), 7.85-7.97 (m, 3H); $^{13}$C-NMR (75.5 MHz, CDCl$_3$) δ 13.7, 18.7, 25.6, 25.7, 26.0, 26.7, 28.0, 28.9, 29.7, 34.5, 34.7, 37.7, 38.0, 39.2, 46.6, 47.7, 52.7, 55.3, 58.5, 60.3, 77.9, 81.7, 98.0, 107.4, 115.0, 117.9, 122.8, 127.4, 128.6, 129.0, 140.2, 151.2, 158.9, 160.6, 161.1, 170.9, 171.6, 171.8, 172.7, 173.3. Maldi-TOF-spectrum: (M+H)$^+$ calcd: 828.5, found: 828.6; (M+Na)$^+$ calcd: 850.5, found: 850.6; (M+K)$^+$ calcd: 866.6, found: 866.6.

Example 45

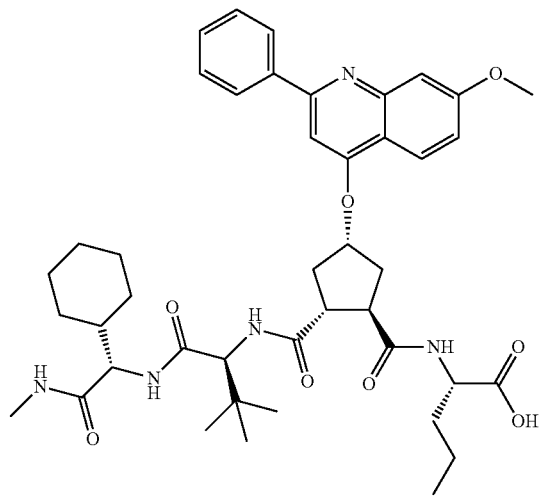

(S)-2-{[(1R,2R,4S)-2-{(S)-1-[((S)-Cyclohexyl-methylcarbamoyl-methyl)-carbamoyl]-2,2-dimethyl-propylcarbamoyl}-4-(7-methoxy-2-phenyl-quinolin-4-yloxy)-cyclopentanecarbonyl]-amino}-pentanoic acid (45)

Compound 44 (21 mg, 0.025 mmol) was dissolved in CH$_2$Cl$_2$ (1.5 mL) and triethylsilane (10 uL, 0.063 mmol) and TFA (1.5 mL) were added. The solution was stirred for 2 hours at room temperature after which the solvents were evaporated and co-evaporated with toluene to provide compound 45 (20 mg, 100%) as a colorless solid.

$^1$H-NMR (300 MHz, CD$_3$OD) δ 0.93 (t, overlapped, 3H), 0.98 (s, 9H), 0.99-1.25 (m, 4H), 1.30-1.49 (m, 3H), 1.50-1.90 (m, 8H), 2.25-2.39 (m, 2H), 2.54-2.62 (m, 1H), 2.64 (s, 3H), 2.72-2.87 (m, 1H), 3.34-3.57 (m, 3H), 4.02-4.13 (m, 1H), 4.06 (s, overlapped, 3H), 427-4.36 (m, 1H), 4.37-4.47 (m, 1H), 5.57-5.66 (m, 1H), 7.45 (dd, J=2.3, 9.2 Hz, 1H), 7.48 (s, 1H), 7.54 (d, J=2.2 Hz, 1H), 7.69-7.79 (m, 3H), 8.01-8.07 (m, 2H), 8.42 (d, J=9.3 Hz, 1H); $^{13}$C-NMR (75.5 MHz, CD$_3$OD) δ 14.0, 20.2, 26.0, 26.9, 27.2, 30.1, 30.7, 34.6, 35.3, 37.2, 39.1, 41.2, 47.7, 53.7, 56.9, 59.4, 59.5, 62.5, 83.7, 100.4, 101.3, 102.2, 116.2, 121.7, 126.7, 129.8, 130.8, 133.3, 133.9, 143.5, 157.9, 166.6, 168.5, 172.5, 173.6, 175.3, 175.4, 175.5.

Maldi-TOF-spectrum: (M+H)$^+$ calcd: 772.4, found: 772.6; (M+Na)$^+$ calcd: 794.4, found: 794.6; (M+K)$^+$ calcd: 810.5, found: 810.6.

Example 46

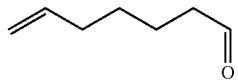

Hept-6-enal (46)

To a solution of hept-6-en-1-ol (1 mL, 7.44 mmol) and N-methylmorpholine N-oxide (1.308 g, 11.17 mmol) in DCM (17 mL) was added ground molecular sieves (3.5 g, 4 Å). The mixture was stirred for 10 min at room temperature under nitrogen atmosphere before tetrapropylammonium perruthenate (TPAP) (131 mg, 0.37 mmol) was added. After stirring for additional 2.5 h the solution was filtered through celite. The solvent was then carefully evaporated and the remaining liquid was purified by flash column chromatography (DCM) to give the volatile aldehyde 46 (620 mg, 74%) as an ol.

Example 47

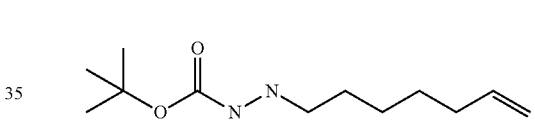

N'-Hept-6-en-(E)-ylidene-hydrazinecarboxylic acid tert-butyl ester (47)

To a solution of 46 (68 mg, 0.610 mmol) and tart-butyl carbazate (81 mg, 0.613 mmol) in MeOH (5 mL) was added ground molecular sieves (115 mg, 3 Å). The mixture was stirred for 3 h after which it was filtered through celite and evaporated. The residue was dissolved in dry THF (3 mL) and AcOH (3 mL). NaBH$_3$CN (95 mg, 1.51 mmol) was added and the solution was stirred over night. The reaction mixture was diluted with saturated NaHCO$_3$ solution (6 mL) and EtOAc (6 mL). The organic phase was washed with brine, saturated NaHCO$_3$, brine, dried over MgSO$_4$ and evaporated. The cyanoborane adduct was hydrolyzed by treatment with MeOH (3 mL) and 2 M NaOH (1.9 mL). The mixture was stirred for 2 h and the MeOH was evaporated. H$_2$O (5 mL) and DCM (5 mL) were added and the water phase was extracted three times with DCM. The combined organic phases were dried and evaporated. Purification by flash column chromatography (toluene/ethyl acetate 9:1 with 1% triethylamine and toluene/ethyl acetate 6:1 with 1% triethylamine) provided 47 (85 mg, 61%) as an oil.

Example 48

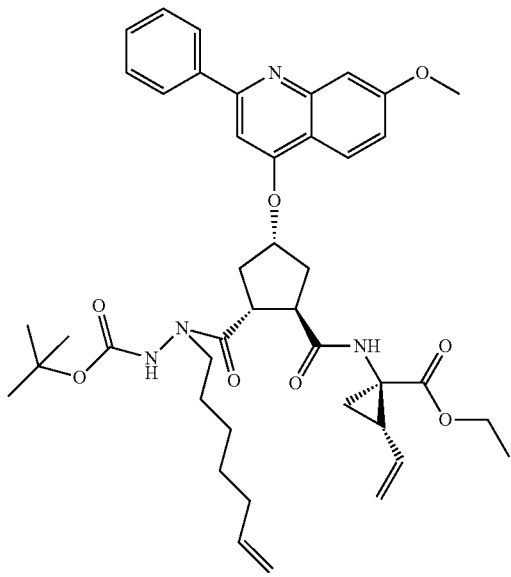 [SMILES: C=CCCCCCN(NC(=O)OC(C)(C)C)C(=O)[C@@H]1C[C@H](Oc2cc(-c3ccccc3)nc3cc(OC)ccc23)C[C@H]1C(=O)N[C@]1(C(=O)OCC)C[C@H]1C=C]

(1R,2)-1-{[(1R,2R,4R)-2-(N'-tert-Butoxycarbonyl-N-hept-6-enyl-hydrazinocarbonyl)-4-(7-methoxy-2-phenyl-quinolin-4-yloxy)-cyclopentanecarbonyl]-amino}-2-vinyl-cyclopropanecarboxylic acid ethyl ester (48)

Scaffold molecule 35 (135 mg, 0.225 mmol) and triethylsilane (71 μL, 0.447 mmol) was dissolved in DCM (2 mL) after which trifluoroacetic acid (TFA) (2 mL) was added. The mixture was stirred for 2 h and thereafter co-evaporated with toluene in order to remove the TFA. The residue was dissolved in DMF (3 mL) and 47 (60 mg, 0.263 mmol) and DIEA (118 μL, 0.677 mmol) were added. The temperature was lowered to 0° C. and the coupling reagent O-(7-azabenzotriazol-1-yl)-N,N,N',N'-tetramethyluronium hexafluorophosphate (HATU) (94 mg, 0.247 mmol) was added. The cold solution was allowed to stir for half an hour and then for additional 16 h in room temperature. The solvent was removed by heating the reaction flask in a water bath under diminished pressure. The residue was thereafter dissolved in ethyl acetate and the organic phase was washed three times with brine, dried, filtered and evaporated. Purification by HPLC (MeOH/H$_2$O 90.10 with 02% triethylamine) gave 48 (140 mg, 82%) as an oil.

$^1$H-NMR (300 MHz, CDCl$_3$, 40° C.): δ 1.22 (t, J=7.1 Hz, 3H), 1.28-1.42 (m, 6H), 1.46 (s, 9H), 1.52-1.62 (m, 2H), 1.82-1.91 (m, 1H), 1.96-2.16 (m, 3H), 2.18-2.34 (m, 2H), 2.42-2.56 (m, 1H), 2.58-2.72 (m, 1H), 3.42 (app. bs, 3H), 3.66-3.84 (m, 1H), 3.92 (s, 3H), 4.15 (q, J=7.1 Hz, 2H), 4.88-5.02 (m, 2H), 5.07-5.18 (m, 2H), 5.20-5.32 (m, 1H), 5.63-5.84 (m, 2H), 6.62 (bs, 1H), 6.94 (s, 1H), 7.09 (dd, J=2.6, 9.2 Hz, 1H), 7.36-7.51 (m, 4H), 7.99-8.10 (m, 3H); $^{13}$C-NMR (75.5 MHz, CDCl$_3$): δ 14.3, 23.0, 26.4, 26.6, 28.3, 28.6, 33.2, 33.5, 35.6, 37.6, 40.6, 44.7, 47.1, 48.6, 55.5, 61.5, 81.9, 98.4, 107.9, 114.5, 115.6, 118.1, 123.2, 127.6, 128.3, 128.7, 129.1, 133.5, 138.7, 140.7, 151.5, 154.5, 159.2, 160.9, 161.5, 170.5, 174.2, 176.3.

Example 49

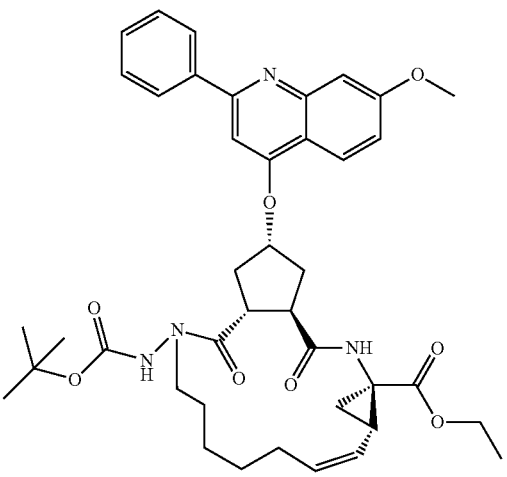 [SMILES: CCOC(=O)[C@@]12C[C@H]1/C=C\CCCCCN(NC(=O)OC(C)(C)C)C(=O)[C@@H]1C[C@H](Oc3cc(-c4ccccc4)nc4cc(OC)ccc34)C[C@H]1C(=O)N2]

(Z)-(1R,4R,6S,16R,18R)-14-tert-Butoxycarbonylamino-18-(7-methoxy-2-phenyl-quinolin-4-yloxy)-2,15-dioxo-3,14-diaza-tricyclo[14.3.0.0$^{4,6}$]nonadec-7-ene-4-carboxylic acid ethyl ester (49)

A solution of 48 (158 mg, 0.209 mmol) in dry DCM (25 mL) was bubbled with argon for 5 min. To the stirred solution under argon atmosphere was then added a solution of Hoveyda-Grubbs catalyst 2$^{nd}$ generation (11 mg, 0.018 mmol) in dry DCM (5 mL). The mixture was stirred at reflux under argon atmosphere for 16 h. The solvent was evaporated and purification by HPLC (MeOH/H$_2$O 90:10 with 0.2% triethylamine) yielded 49 (107 mg, 70%) as a colorless solid.

$^1$H-NMR (300 MHz, CD$_3$OD): δ 1.03-1.22 (m, 1H), 1.28 (t, J=7.1 Hz, 3H), 1.32-1.44 (m, 4H), 1.49 (s, 9H), 1.55-1.73 (m, 2H), 1.81-1.91 (m, 1H), 2.04-2.28 (m, 3H), 2.30-2.52 (m, 3H), 2.53-2.70 (m, 1H), 2.86-3.00 (m, 1H), 3.34-3.44 (m, 1H), 3.48-3.62 (m, 1H), 3.95 (s, 3H), 4.19 (q, J=7.1 Hz, 2H), 4.32-4.48 (m, 1H), 5.20-5.33 (m, 1H), 5.34 (bs, 1H), 5.58-5.70 (m, 1H), 7.10 (s, 1H), 7.14 (dd, J=2.5, 9.1 Hz, 1H), 7.39 (d, J=2.5 Hz, 1H), 7.45-7.55 (m, 3H), 8.00 (d, J=8.0 Hz, 2H), 8.17 (d, J=9.3 Hz, 1H); $^{13}$C-NMR (75.5 MHz, CD$_3$OD): δ 14.6, 23.4, 27.5, 27.7, 28.0, 28.5, 30.7, 36.1, 38.1, 42.5, 45.8, 56.0, 62.7, 79.9, 82.8, 100.2, 107.4, 116.8, 119.1, 124.5, 126.5, 128.9, 129.8, 130.5, 135.8, 141.5, 152.2, 156.4, 161.3, 162.5, 163.1, 171.9, 175.8, 179.0. MALDI-TOF-spectrum: (M+H)$^+$ calcd: 727.4, found: 727.5.

Example 50

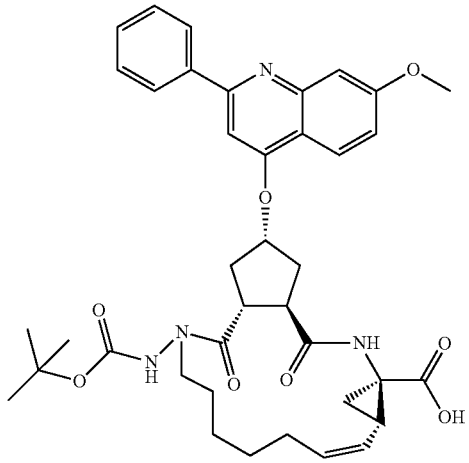 [SMILES: COc1ccc2c(O[C@@H]3C[C@H]4C(=O)N[C@]5(C(=O)O)C[C@H]5/C=C\CCCCCN(NC(=O)OC(C)(C)C)C(=O)[C@@H]4C3)cc(-c3ccccc3)nc2c1]

(Z)-(1R,4R,6S,16R,18R)-14-tert-Butoxycarbo-nylamino-18-(7-methoxy-2-phenyl-quinolin-4-yloxy)-2,15-dioxo-3,14-diaza-tricyclo[14.3.0.0$^{4,6}$] nonadec-7-ene-4-carboxylic acid (50)

To a solution of 49 (27 mg, 0.037 mmol) in THF/MeOH/H$_2$O 2:1:1 (5 mL) was added 1 M LiOH (300 μL, 0.300 mmol). The solution was stirred for 24 h at room temperature and finally for one hour at reflux. After acidification to pH 3-4 with 1 M HCl and evaporation the residue was purified by HPLC (MeOH/H$_2$O 80:20 and MeOH/H$_2$O 90:10) providing 50 (12 mg, 46%) as a colorless sold.

$^1$H-NMR (300 MHz, CD$_3$OD): δ 1.06-1.24 (m, 1H), 126-1.42 (m, 3H), 1.48 (s, 9H), 1.52-1.73 (m, 3H), 1.80-1.90 (m, 1H), 2.02-2.15 (m, 1H), 2.15-2.40 (m, 4H), 2.43-2.54 (m, 1H), 2.54-2.68 (m, 1H), 2.88-3.00 (m, 1H), 3.35-3.48 (m, 1H), 3.49-3.66 (m, 1H), 3.96 (s, 3H), 4.32-4.48 (m, 1H), 5.25-5.42 (m, 2H), 5.56-5.88 (m, 1H), 7.14 (s, 1H), 7.17 (dd, J=2.5, 9.1 Hz, 1H), 7.40 (d, J=2.2 Hz, 1H), 7.46-7.58 (m, 3H), 8.00 (d, J=8.0 Hz, 2H), 8.19 (d, J=9.1 Hz, 1H); $^{13}$C-NMR (75.5 MHz, CD$_3$OD): δ 23.6, 26.8, 27.8, 28.3, 28.5, 30.5, 35.8, 38.1, 43.0, 45.5, 56.0, 802, 82.7, 100.4, 106.9, 116.6, 1192, 124.7, 127.4, 129.0, 129.8, 130.7, 134.8, 140.9, 151.6, 156.5, 161.1, 163.0, 163.4, 173.8, 175.7, 179.3.

Example 51

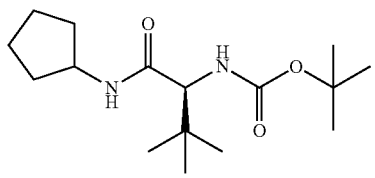 [SMILES: CC(C)(C)OC(=O)N[C@H](C(=O)NC1CCCC1)C(C)(C)C]

((S)-1-Cyclopentylcarbamoyl-2,2-dimethyl-propyl)-carbamic acid tert-butyl ester (51)

To a cold solution of 36 (133 mg, 0.575 mmol), cyclo-pentylamine (64 μL, 0.648 mmol) and DIEA (301 μL, 1.73 mmol) in DMF (3 mL) was added the coupling reagent HATU (240 mg, 0.631 mmol). The mixture was stirred for half an hour and for additional two hours at room temperature. The solvent was removed by heating the reaction flask in a water bath under diminished pressure and the residue was dissolved in ethyl acetate, after which the organic phase was washed three times with brine, dried, filtered and evaporated. Purification by flash column chromatography (toluene/ethyl acetate 4:1) provided 51 (140 mg, 82%) as colorless crystals.

$^1$H-NMR (300 MHz, CDCl$_3$): δ 0.95 (s, 9H), 1.28-1.48 (m, overlapped, 2H), 1.40 (s, 9H), 1.49-1.71 (m, 4H), 1.86-2.01 (m, 2H), 3.76 (b, 1H), 4.09-4.23 (m, 1H), 5.32 (b, 1H), 5.91 (b, 1H); $^{13}$C-NMR (75.6 MHz, CDCl$_3$): δ 23.6, 23.7, 26.5, 28.3, 32.6, 33.1, 34.5, 51.0, 62.2, 79.4, 155.9, 170.3.

Example 52

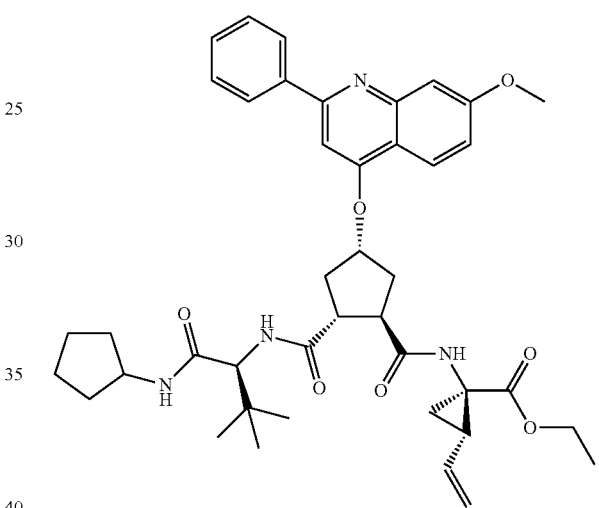

(1R,2S)-1-{[(1R,2R,4S)-2-((S)-1-Cyclopentylcar-bamoyl-2,2-dimethyl-propylcarbamoyl)-4-(7-methoxy-2-phenyl-quinolin-4-yloxy)-cyclopentan-ecarbonyl]-amino)}-2-vinyl-cyclopropanecarboxylic acid ethyl ester (52)

Compound 51 (298 mg, 0.048 mmol) and 35 (16 mg, 0.054 mmol) was deprotected and coupled according to the method for the preparation of 39. Purification by HPLC (MeOH/H$_2$O 90:10 with 0.2% triethylamine) gave 52 (22 mg, 63%) as a colorless solid.

$^1$H-NMR (CDCl$_3$, 300 MHz): δ 0.97 (s, 9H), 1.21 (t, J=7.1 Hz, 3H), 1.26-1.37 (m, 1H), 1.38-1.46 (m, 2H), 1.48-1.58 (m, 4H), 1.78-1.85 (m, 1H), 1.86-2.02 (m, 3H), 2.03-2.19 (m, 1H), 2.28-2.40 (m, 2H), 2.41-2.54 (m, 1H), 2.64-2.78 (m, 1H), 3.10-3.24 (m, 1H), 3.30-3.44 (m, 1H), 3.95 (s, 3H), 4.04-4.21 (m, 3H), 5.12 (dd, J=1.7, 10.3 Hz, 1H), 5.14-5.22 (m, 1H), 5.28 (dd, J=1.7, 17.0 Hz, 1H), 5.59 (b, 1H), 5.75 (ddd, J=8.8, 10.3, 17.0 Hz, 1H), 6.66-8.82 (m, 2H), 6.99 (s, 1H), 7.09 (dd, J=2.5, 9.1 Hz, 1H), 7.41-7.55 (m, 4H), 7.99-8.09 (m, 3H); $^{13}$C-NMR (75.5 MHz, CDCl$_3$): δ 14.3, 22.9, 23.6, 23.6, 26.7, 32.7, 332, 33.7, 34.8, 35.9, 36.6, 40.2, 46.4, 47.5, 51.3, 55.5, 61.1, 61.4, 78.0, 98.4, 107.1, 115.2, 117.9, 118.2, 123.1, 127.6, 128.8, 129.3, 133.5, 159.1, 161.4, 169.4, 189.9, 173.1, 174.0. MALDI-TOF-spectrum:

(M+H)+ calcd: 725.4, found: 725.6; (M+Na)+ calcd: 747.4, found: 747.6; (M+K)+ calcd: 763.3, found: 763.5.

Example 53

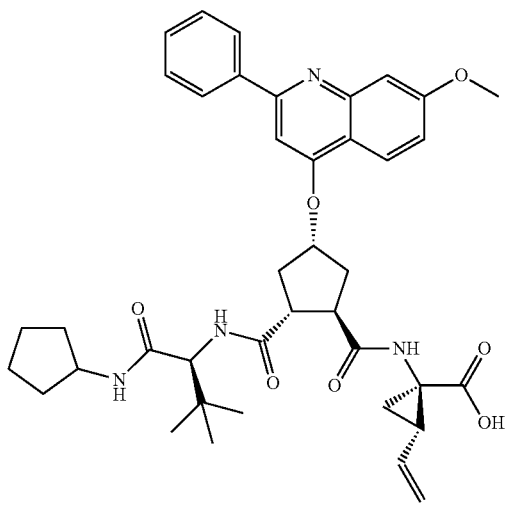 [SMILES: C=C[C@@H]1C[C@]1(NC(=O)[C@@H]1C[C@@H](Oc2cc(-c3ccccc3)nc3cc(OC)ccc23)C[C@H]1C(=O)N[C@H](C(=O)NC1CCCC1)C(C)(C)C)C(=O)O]

(1R,2S)-1-{[(1R,2R,4S)-2-((S)-1-Cyclopentylcarbamoyl-2,2-dimethyl-propylcarbamoyl)-4-(7-methoxy-2-phenyl-quinolin-4-yloxy)-cyclopentanecarbonyl]-amino}-2-vinyl-cyclopropanecarboxylic acid (53)

To a solution of 52 (14 mg, 0.019 mmol) in dioxane/HO 1:1: (4 mL) was added 1 M LiOH (115 μL, 0.115 mmol). The solution was stirred for 24 h at room temperature. Thereafter an additional portion of LiOH (75 uL, 0.075 mmol) was added and the solution was stirred for another 24 h. After acidification to approximately pH 3 with 1 M HCl and co-evaporation with toluene the residue was purified by HPLC (MeOH/H₂O 70:30 with 02% TFA) yielding 53 (8 mg, 60%) as a colorless solid.

¹H-NMR (300 MHz, CD₃OD): δ 0.98 (s, 9H), 1.28-1.48 (m, 3H), 1.49-1.76 (m, 5H), 1.78-1.94 (m, 2H), 2.10-2.24 (m, 1H), 2.26-2.45 (m, 2H), 2.50-2.62 (m, 1H), 2.66-2.79 (m, 1H), 3.35-3.48 (m, 2H), 3.94-4.03 (m, 1H), 4.06 (s, 3H), 4.16-4.24 (m, 1H), 5.10 (dd, J=1.8, 10.3 Hz, 1H), 5.29 (dd, J=1.8, 17.2 Hz, 1H), 5.62 (b, 1H), 5.82 (ddd, J=9.1, 10.3, 17.2 Hz, 1H), 7.43 (dd, J=2.5, 9.3 Hz, 1H), 7.50 (s, 1H), 7.50-7.69 (dd, overlapped, 1H), 7.67-7.80 (m, 3H), 8.01-8.11 (m, 2H), 8.39 (d, J=9.3 Hz, 1H); ¹³C-NMR (75.5 MHz, CD₃OD): δ 24.7, 24.7, 27.3, 33.1, 33.6, 34.7, 35.4, 36.9, 38.7, 41.0, 47.4, 52.3, 56.9, 62.3, 83.9, 100.4, 102.3, 116.2, 117.7, 121.6, 126.7, 129.8, 130.8, 133.4, 133.8, 135.6, 143.5, 158.0, 166.5, 168.6, 171.9, 173.4, 175.2, 176.4. MALDI-TOF-spectrum: (M+H)+ calcd: 697.4, found: 897.3; (M+Na)+ calcd: 718.7, found: 719.3; (M+K)+ calcd: 735.3, found: 735.3.

Example 54

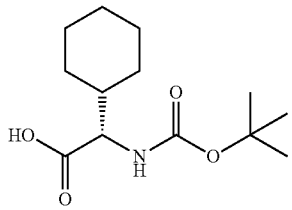

(S)-tert-Butoxycarbonylamino-cyclohexyl-acetic add methyl ester (54)

To a solution of Boc-Chg-OH (53 mg, 0206 mmol) in acetone (3 mL) were added methyl iodide (195 μL, 3.1 mmol) and sliver (I) oxide (53 mg, 0.229 mmol). The mixture was allowed to stir over night in a reaction flask that was covered with aluminium foil Thereafter the solution was filtered through celite and evaporated. Purification by flash column chromatography (toluene/ethyl acetate 15:1) provided methyl ester 54 (56 mg, 100%) as a colorless oil.

¹H-NMR (300 MHz, CDCl₃): δ 1.00-1.34 (m, 5H), 1.44 (s, 9H), 1.54-1.82 (m, 6H), 3.73 (s, 3H), 4.20 (dd, J=2.8, 5.0 Hz, 1H), 5.05 (bs, 1H); ¹³C-NMR (75.5 MHz, CDCl₃): δ 26.0, 28.2, 28.3, 29.5, 41.1, 52.0, 58.3, 79.7, 155.6, 172.9.

Example 55

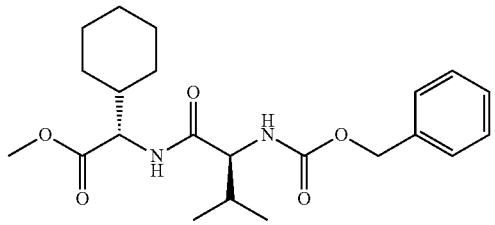 [SMILES: COC(=O)[C@@H](NC(=O)[C@@H](NC(=O)OCc1ccccc1)C(C)C)C1CCCCC1]

(S)—((S)-2-Benzyloxycarbonylamino-3-methy-butyrylamino)-cyclohexyl-acetic acid methyl ester (55)

Compound 54 (93 mg, 0.343 mmol) was deprotected and coupled to Z-Val-OH (95 mg, 0.378 mmol according to the method for the preparation of 39. Flash column chromatography (toluene/ethyl acetate 4:1) gave 55 (131 mg, 94%) as a colorless solid.

¹H-NMR (300 MHz, CDCl₃): δ 0.92-1.30 (m, 11H), 1.54-1.88 (m, 6H), 2.02-2.18 (m, 1H), 3.72 (s, 3H), 4.05-4.18 (m, 1H), 4.52 (dd, J=3.0, 5.5 Hz, 1H), 5.12 (s, 2H), 5.49 (bs, 1H), 6.52 (bs, 1H), 7.34 (s, 5H); ¹³C-NMR (75.5 MHz, CDCl₃): δ 17.8, 19.0, 25.8, 28.2, 29.3, 31.2, 40.5, 51.9, 56.8, 60.0, 88.8, 127.7, 127.9, 128.1, 128.3, 136.2, 156.3, 171.3, 172.2.

Example 56

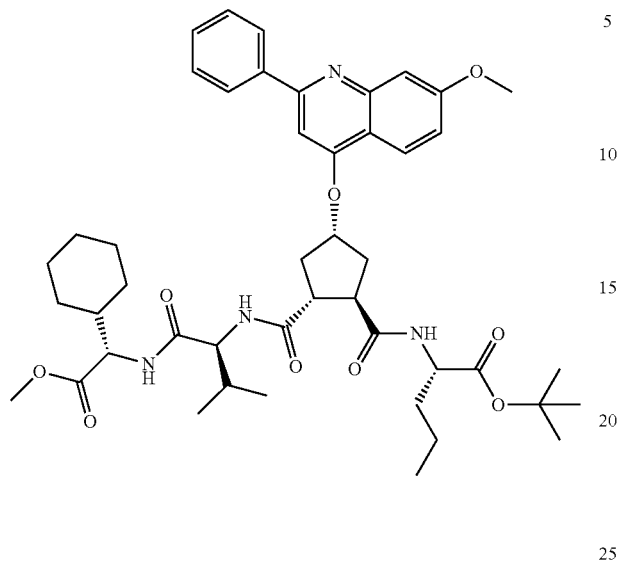

(S)-2-{[(1R,2R,4S)-2-{(S)-1-[((S)-Cyclohexyl-ethoxycarbonyl-methyl)-carbamoyl]-2-methyl-propylcarbamoyl}-4(7-methoxy-2-quinolin-4-yloxy)-cyclopentanecarbonyl]-amino}-pentanol acid tert-butyl ester (56)

To a solution of 55 (40 mg, 0.099 mmol) in ethanol (95%) (7.5 mL) was added palladium on active carbon (10%, 40 mg) and the mixture was hydrogenated under pressure at room temperature for 2 h. The mixture was filtered through celite and evaporated. Compound 43 (38 mg, 0.083 mmol) was dissolved in dioxane/H$_2$O 1:1 (3 mL) and the mixture was cooled to 0° C. before 1 M LiOH (140 µL, 0.140 mmol) was added to the stirred solution. After 1 h the mixture was neutralized with 1 M hydrochloric acid and the solvent was evaporated and co-evaporated with toluene. The residue was coupled to deprotected 55 using the same HATU coupling conditions as in the synthesis of compound 48. Purification by HPLC (MeOH/H$_2$O 90:10 with 0.2% triethylamine) gave 56 (56 mg, 88%) as a colorless sold. $^1$H-NMR (300 MHz, CDCl$_3$): δ 0.82-0.96 (m, 9H), 0.82-1.22 (m, overlapped, 6H), 1.23-1.40 (m, 2H), 1.44 (s, 9H), 1.50-1.69 (m, 4H), 1.71-1.87 (m, 2H), 1.95-2.06 (m, 1H), 2.07-2.22 (m, 1H), 2.28-2.54 (m, 3H), 2.60-2.75 (m, 1H), 3.08-3.28 (m, 1H), 3.30-3.49 (m, 1H), 3.70 (s, 3H), 3.94 (s, 3H), 4.28-4.38 (m, 1H), 4.41-4.57 (m, 2H), 5.17 (b, 1H), 6.54-6.70 (m, 2H), 6.74 (b, 1H), 6.95 (s, 1H), 7.09 (dd, J=2.5, 9.1 Hz, 1H), 7.39-7.55 (m, 5H), 7.98-8.10 (m, 3H); $^{13}$C-NMR (75.5 MHz, CDCl$_3$): δ 13.7, 18.1, 18.6, 19.2, 25.9, 28.0, 28.2, 29.6, 30.7, 34.6, 36.5, 37.6, 40.8, 47.4, 47.5, 52.1, 52.8, 55.5, 56.8, 58.9, 77.8, 82.0, 98.3, 107.5, 115.3, 118.1, 123.1, 127.5, 128.7, 129.1, 140.5, 151.4, 159.2, 160.7, 161.3, 171.0, 171.5, 172.3, 172.8, 173.0. MALDI-TOF-spectrum: (M+H)$^+$ calcd: 815.5, found: 815.7; (M+Na)$^+$ calcd: 837.4, found: 837.6; (M+K)$^+$ calcd: 853.4, found: 853.6.

Example 57

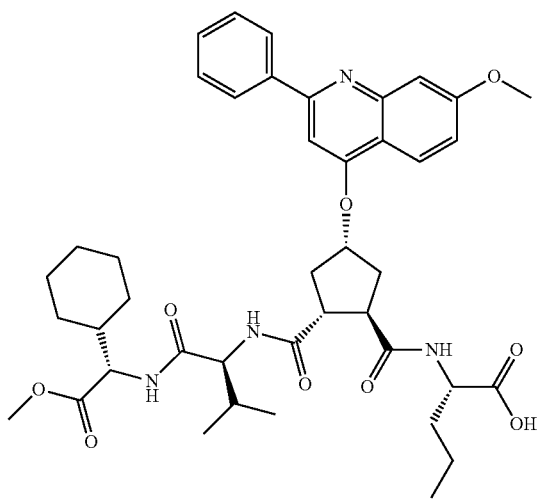

(S)-2-{[(1R,2R,4S)-2-{(S)-1-[((S)-Cyclohexyl-methoxycarbonyl-methy)-carbamoyl]-2-methyl-propylcarbamoyl}-4-(7-methoxy-2-phenyl-quinolin-4-yloxy)-cyclopentanecarbonyl]-amino}-pentanoic acid (57)

Tert.butyl ester 56 (28 mg, 0.034 mmol) and triethylsilane (14 µL, 0.088 mmol) was dissolved in DCM (2 mL) after which trifluoroacetic acid (2 mL) was added and the mixture was stirred for 2 h. Co-evaporation with toluene gave 57 (26 mg, 100%) as a colorless solid.

$^1$H-NMR (300 MHz, CD$_3$OD): δ 0.86-1.00 (m, 9H), 1.01-1.24 (m, 4H), 1.36-1.46 (m, 2H), 1.48-1.75 (m, 8H), 1.70-1.89 (m, overlapped, 1H), 1.96-2.12 (m, 1H), 2.22-2.40 (m, overlapped, 2H), 2.49-2.64 (m, 1H), 2.72-2.91 (m, 1H), 3.26-3.40 (m, overlapped, 1H), 3.50-3.68 (m, overlapped, 1H), 3.62 (s, 3H), 4.05 (s, 3H), 4.09-4.17 (m, 1H), 4.17-4.25 (m, 1H), 4.35-4.45 (m, 1H), 5.82 (b, 1H), 7.44 (dd, J=2.2, 9.3 Hz, 1H), 7.49 (s, 1H), 7.53 (d, J=2.2 Hz, 1H), 7.65-7.78 (m, 3H), 7.98-8.06 (m, 2H), 8.41 (dd, J=2.8, 9.3 Hz, 1H); $^{13}$C-NMR (CD$_3$OD, 75.5 MHz): δ 13.9, 18.8, 19.7, 20.2, 27.0, 29.7, 30.5, 31.8, 34.6, 37.7, 38.9, 41.1, 47.8, 52.3, 53.6, 56.9, 58.8, 58.9, 60.3, 83.8, 100.4, 102.2, 116.2, 121.6, 126.7, 129.8, 130.8, 133.3, 133.8, 143.5, 157.9, 166.5, 168.5, 173.3, 173.9, 175.5, 175.5, 175.6. MALDI-TOF-epectrum: (M+H)$^+$ calcd: 759.4, found: 759.7; (M+Na)$^+$ calcd: 781.4, found: 781.7; (M+K)$^+$ calcd: 797.4, found: 797.7.

Example 58

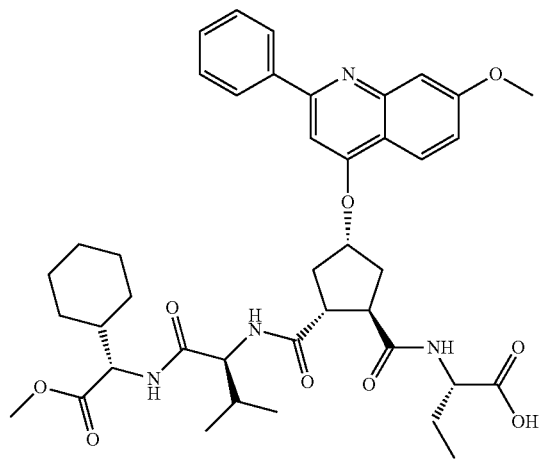

(S)-2-{[(1R,2R,4S)-2-{(S)-1 [((S)Cyclohexyl-methoxycarbonyl-methyl)carbamoyl]-2-methyl-propylcarbamoyl}-4-(7-methoxy-2-phenyl-quinolin-4-yloxy)-cyclopentanecarbonyl]-amino}-butyric acid
(58)

The procedure described in example 42 was followed but with the use of L-2-amino-N-butyric acid tert.butyl ester instead of H-Nva-OtBu. The afforded compound was then reacted as described in example 43 which gave (1R,2R,4R)-2-((S)-1-tert-butoxycarbonyl-propylcarbamoyl)-4-(7-methoxy-2-phenyl-quinolin-4-yloxy) cyclopentanecarboxylic acid methyl ester. Coupling of this compound with 55 as described in example 56 followed by esterhydrolysis as described in example 57 gave 58 as a colourless solid.

$^1$H-NMR (300 MHz, CD$_3$OD): δ 0.82-0.99 (m, 9H), 0.82-1.40 (m, overlapped, 6H), 1.48-1.78 (m, 6H), 1.80-1.95 (m, 1H), 1.97-2.12 (m, 1H), 2.22-2.40 (m, overlapped, 2H), 2.51-2.64 (m, 1H), 2.71-2.90 (m, 1H), 3.16-3.39 (m, overlapped, 1H), 3.49-3.59 (m, 1H), 3.63 (s, 3H), 3.95 (s, 3H), 4.12-4.23 (m, 2H), 4.28-4.38 (m, 1H), 5.31 (b, 1H), 7.43 (dd, J=2.2, 9.3 Hz, 1H), 7.47 (s, 1H), 7.51 (s, 1H), 7.66-7.89 (m, 3H), 7.99-8.07 (m, 2H), 8.42 (d, J=9.1 Hz, 1H); $^{13}$C-NMR (75.5 MHz, CD$_3$OD): δ 10.7, 18.8, 19.7, 25.8, 27.0, 27.0, 29.7, 30.5, 31.8, 37.7, 38.9, 41.2, 47.9, 52.3, 55.3, 56.9, 58.8, 60.6, 83.6, 100.7, 102.2, 118.3, 121.5, 126.7, 129.8, 130.8, 133.7, 133.8, 143.9, 158.2, 166.4, 168.3, 173.3, 173.8, 175.2, 175.5, 175.6. MALDI-TOF-spectrum: (M+H)$^+$ calcd: 745.4, found: 744.9; (M+Na)$^+$ calcd: 767.4, found: 766.9; (M+K)$^+$ calcd: 783.5, found: 782.9.

Example 59

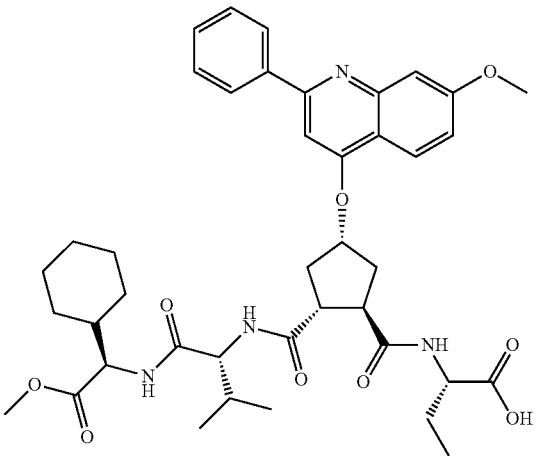

(S)-2-{[(1R,2R,4S)-2-{((R)-1-[((R)-Cyclohexyl-methoxycarbonyl-methyl)-carbamoyl]-2-methyl-propylcarbamoyl}-4-(7ethoxy-2-phenyl-quinolin-4-yloxy)-cyclopentanecarbonyl]-amino}-butyric acid
(59)

The procedure described in example 54 was followed but with the use of Boo-D-cyclohexyglycine Instead of Boc-L-cyclohexyglycine. The afforded compound was then reacted as described in example 55 followed by coupling with (1R,2R,4R)-2-((S)-1-tert-Butoxycarbonyl-pentylcarbamoyl)-4-(7-methoxy-2-phenyl-quinolin-4-yloxy)-cyclopentanecarboxylic acid methyl ester as described in example 56. Removal of the ester group as described in example 57 gave compound 59 as a colourless solid. $^1$H-NMR (CD$_3$OD, 300 MHz): δ 0.82-1.02 (m, 9H), 1.04-1.42 (m, 6H), 1.52-1.80 (m, 6H), 1.80-1.95 (m, overlapped, 1H), 2.00-2.14 (m, 1H), 2.29-2.46 (m, 2H), 2.51-2.65 (m, 1H), 2.68-2.84 (m, 1H), 3.24-3.39 (m, overlapped, 1H), 3.47-3.60 (m, 1H), 3.67 (s, 3H), 4.07 (s, 3H), 4.18-427 (m, 2H), 4.28-4.38 (m, 11H), 5.64 (app. bs, 1H), 7.44 (d, J=2.3, 6.9 Hz, 1H), 7.42 (s, 2H), 7.67-7.81 (m, 3H), 8.04 (d, J=7.8 Hz, 2H), 8.41 (d, J=9.1 Hz, 1H); $^{13}$C-NMR (CD$_3$OD, 75.5 MHz): δ 10.8, 18.5, 19.6, 25.7, 27.1, 27.1, 30.1, 30.8, 31.9, 37.3, 38.2, 41.1, 47.8, 52.3, 55.4, 56.9, 59.0, 59.1, 60.2, 83.8, 100.5, 102.2, 116.3, 121.6, 126.8, 1298, 130.8, 133.6, 133.8, 143.7, 158.1, 166.5, 168.5, 173.4, 173.8, 175.4, 175.7, 175.7. MALDI-TOF-spectrum: (M+H)$^+$ calcd: 745.4, found: 745.4; (M+Na)$^+$ calcd: 767.4, found: 767.4; (M+K)$^+$ calcd: 783.5, found: 783.3.

Example 60

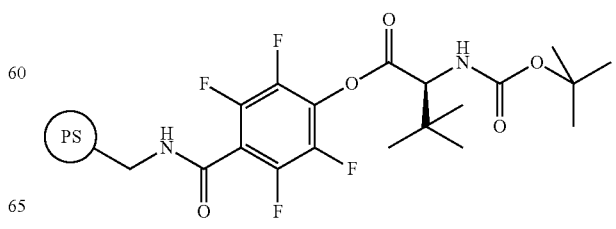

Resin bound 2-tert.butoxycarbonylamino-3,3-dimethylbutyric acid (60)

To Argonaut resin PS-TFP (1.38 mmol/g, 10 g) and 2-tert-butoxycarbonylamino-3,3-dimethyl-butyric acid (4.5 g, 20.7 mmol) was added dichloromethane (40 mL) and DMF (10 mL). To this mixture was added DMAP (1 g, 8.28 mmol) and then DIC (9.5 mL, 60.7 mmol). After 3 hrs of agitation at RT the resin was filtered and washed successively with DMF, THF, DCM, THF, DCM and ether and then dried in a vacuum.

Example 61

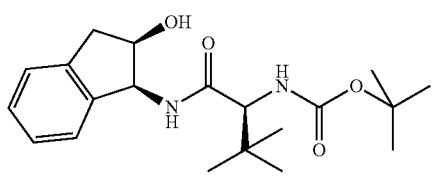 [SMILES: CC(C)(C)OC(=O)N[C@H](C(=O)N[C@H]1c2ccccc2C[C@H]1O)C(C)(C)C]

[1-(2-Hydroxy-indan-1-ylcarbamoyl)-2,2-dimethyl-propyl]-carbamic acid tertbutyl ester (61)

To a portion of 60 (200 mg) in DCM aminoindanol (0.14 mmol) was added. The mixture was agitated for 2 hrs. The liquid was filtered of and the resin washed with 2×DCM. The combined liquids were combined and concentrated to dryness to afford the title compound (20.5 mg, 0.055 mmol) Purity>95% by HPLC. M+H$^+$ 363.15. $^{13}$C NMR δ$_c$ (100 MHz; CDCl$_3$; Me$_4$Si) 27.0, 28.5, 34.2, 39.8, 50.8, 57.9, 68.2, 73.7, 124.8, 125.6, 127.4, 128.5, 140.4, 171.6. $^1$H NMR δ$_H$ (400 MHz; CDCl$_3$; Me$_4$Si) 1.07 (9H, s, CCH$_3$), 1.44 (9H, s, OCCH$_3$), 2.93 (1H, dd, J$_{gem}$ 16.4 Hz, J$_{3,2}$ 2.3 Hz, CH$_2$), 3.15 (1H, dd, J$_{gem}$ 16.4 Hz, J$_{3,2}$ 5.2 Hz, CH$_2$),

Example 62

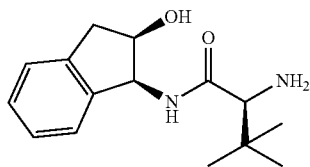 [SMILES: CC(C)(C)[C@H](N)C(=O)N[C@H]1c2ccccc2C[C@H]1O]

2-Amino-N-(2-hydroxy-indan-1-yl)-3,3-dimethyl butyramide (62)

Compound 61 was kept in DCM-TFA 2:1 (2 mL) for 60 min at RT. The solution was co-evaporated with toluene to dryness.

Example 63

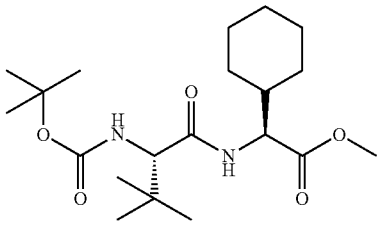 [SMILES: COC(=O)[C@@H](NC(=O)[C@@H](NC(=O)OC(C)(C)C)C(C)(C)C)C1CCCCC1]

(2-tert-Butoxycarbonylamino-3,3-dimethyl-butyrylamino)-cyclohexyl-acetic acid methyl ester (63)

To a solution of 2-tert.butoxycarbonylamino-3,3-dimethyl butyric acid (500 mg, 2.16 mmol), Amino-cyclohexyl-acetic add methyl ester (444 mg, 2.59 mmol) and HATU (2 g, 5.40 mmol) in DMF (20 mL) was added diisopropylethylamine (1.88 mL, 10.8 mmol). The solution was stirred for 1 hrs at r.t. and diluted with dichloromethane (40 mL). This solution was washed with aqueous. NaHCO$_3$ (sat) and water (×2), dried and concentrated. The product was >95% pure. M+H$^+$ 385.4.

Example 64

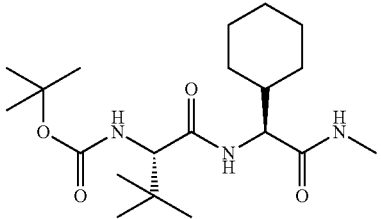 [SMILES: CNC(=O)[C@@H](NC(=O)[C@@H](NC(=O)OC(C)(C)C)C(C)(C)C)C1CCCCC1]

{1-[(Cyclohexyl-methylcarbamoyl-methyl)-carbamoyl]-2,2-dimethyl-propyl}-carbamic acid tert-butyl ester (64)

To compound 63 in EtOH-THF 1:2 was added a large excess of methylamine (30% in water) and left at rt. for 2 weeks. The solution was concentrated to dryness and the residue subjected to a short silica gel column eluted with 2% MeOH in dichloromethane to give a pure (>95%) product M+H$^+$ 384.5.

Example 65

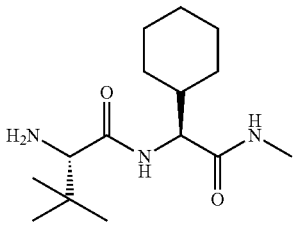 [SMILES: CNC(=O)[C@@H](NC(=O)[C@@H](N)C(C)(C)C)C1CCCCC1]

2-Amino-N-(cyclohexyl-methylcarbamoyl-methyl)-
3,3-dimethyl-butyramide (65)

Compound 64 was kept in dichloromethane-trifuoroacetic acid 2:1 for 1 h at rt and concentrated to dryness. The residue was dried in a vacuum for 16 hr. Reversed phase C18 HPLC showed >95% purity M+H+ 283.1.

Example 66

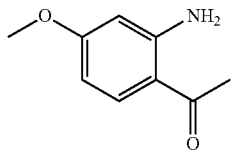

1-(2-Amino-4-methoxyphenyl)ethanone (66)

m-Anisidine (10.0 g, 82 mmol) was dissolved in CH$_2$Cl$_2$ (50 mL), and the solution was cooled to −50° C. BCl$_3$(1 M in CH$_2$Cl$_2$, 82 mL, 82 mmol) was added slowly during 20 min, after which the mixture was stirred at −50° C. for 30 min, followed by sequential addition of AcCl (6.0 mL, 84 mmol) and AlCl$_3$ (11 g, 82 mmol). The mixture was stirred at −50° C. for 1 h and was then allowed to assume rt. Alter stirring at rt overnight, the solution was heated at 40° C. for 4 h, after which the mixture was poured over ice. The aqueous mixture was made alkaline with 10% NaOH (w/v) and extracted with EtOAc (4×200 mL). The combined organic phases were washed with brine, dried (MgSO$_4$), and evaporated to give a black solid, which was purified by flash column chromatography (ether/CH$_2$Cl$_2$ 20:80). The resulting solid was recrystallized from ether/hexane to give compound 93 as shiny tan leaflets (5.6 g, 42%).

Example 67

N-(tert-Butyl)-N'-isopropylthiourea (67)

To a solution of tert-butylisothiocyanate (5.0 mL, 39 mmol) in CH$_2$Chi (200 mL) were added isopropylamine (4.0 mL, 47 mmol) and disopropylethylamine (DIEA) (6.8 mL, 39 mmol), and the mixture was stirred at rt for 2 h. The reaction mixture was diluted with EtOAc, washed with 10% citric acid (2×), saturated NaHCO$_3$ (2×), H$_2$O (2×), and brine (1×). The organic layer was dried (MgSO$_4$) and evaporated to yield the tide compound (3.3 g, 52%) as a white solid which was used without further purification.

Example 68

N-Isopropylthiourea (68)

Compound 67 (3.3 g, 20 mmol) was dissolved in conc. HCl (45 mL) and the solution was refluxed for 40 min. The mixture was allowed to cool to rt and then cooled in an ice bath and basified to pH 9.5 with sold and saturated NaHCO$_3$, after which the product was extracted into EtOAc (3×). The combined organic phases were washed with H$_2$O (2×) and brine (1×), dried (MgSO$_4$), and evaporated to yield the crude title compound (2.1 g, 90%) which was used without further purification.

Example 69

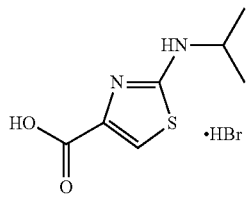

2-(Isopropylamino)-1,3-thiazole-4-carboxylic acid hydrobromide (69)

A suspension of compound 68 (2.1 g, 18 mmol) and 3-bromopyruvic acid (3.0 g, 18 mmol) in dioxane (180 mL) was heated to 80° C. Upon reaching 80° C. the mixture became clear, and soon thereafter the product started to precipitate as a white solid. After 2 h of heating, the reaction mixture was cooled to rt and the precipitate was filtered off and collected. This yielded pure title product (4.4 g, 94%).

Example 70

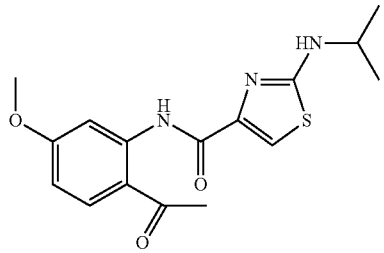 [SMILES: COc1ccc(C(C)=O)c(NC(=O)c2csc(NC(C)C)n2)c1]

N-(2-Acetyl-5-methoxyphenyl)-2-(isopropylamino)-
1,3-thiazole-4-carboxamide (70)

A mixture of compound 69 (4.4 g, 16.5 mmol) and the aniline derivative 66 (2.75 g, 16.5 mmol) in pyridine (140 mL) was cooled to −30° C. (upon cooling, the clear solution became partially a suspension). POCl$_3$ (3.3 mL, 35 mmol) was added slowly over a 5 min period. The mixture was stirred at −30° C. for 1 h, and was then allowed to assume rt. After stirring at rt for 1.5 h the reaction mixture was poured over ice, and the pH was adjusted to about 9-10 using solid and saturated NaHCO$_3$. The crude product was extracted into CH$_2$Cl$_2$ (3×) and the combined organic phases were dried (MgSO$_4$) and evaporated. The crude dark-beige solid was purified by flash column chromatography (hexane/EtOAc 55:45) to give compound 70 (5.6 g, 76%) as a pale yellow solid.

Example 71

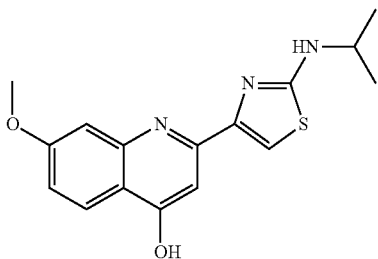 [SMILES: COc1ccc2c(O)cc(-c3csc(NC(C)C)n3)nc2c1]

2-[2-(Isopropylamino)-1,3-thiazol-4-yl]-7-methoxy-quinolin-4-ol (71)

A solution of tBuOK (2.42 g, 21 mmol) in anhydrous t.BuOH (40 mL) was heated to reflux Compound 70 (1.8 g, 5.4 mmol) was added portion-wise over a 5 min period, and the dark red solution formed was stirred at reflux for an additional 20 min. The mixture was cooled to rt, and HCl (4 M in dioxane, 8.0 mL, 32 mmol) was added, after which the reaction mixture was concentrated under vacuum. In order to assure that all of the HCl and dioxane were removed, the crude product was re-dissolved in $CH_2Cl_2$ twice and thoroughly evaporated to obtain the slightly impure HCl salt of compound 71 (1.62 g) as a brown solid. The product was dissolved in $CH_2Cl$ and washed with saturated $NaHCO_3$, after which the aqueous phase was extracted several times with $CH_2Cl_2$. The combined organic phases were dried ($MgSO_4$) and evaporated to give compound 71 (1.38 g, 81%) as a light brown solid (>95% pure according to HPLC tests). $^1$H-NMR (MeOH-$d_4$, 400 MHz): δ 1.30 (d, J=8.0 Hz, 6H), 3.93 (s, 3H), 3.95-4.07 (m, 1H), 6.73 (s, 1H), 8.99 (dd, J=2.4, 9.2 Hz, 1H), 7.26 (d, J=2.4 Hz, 1H), 7.37 (s, 1H), 8.10 (d, J=9.2 Hz, 1H).

Example 72

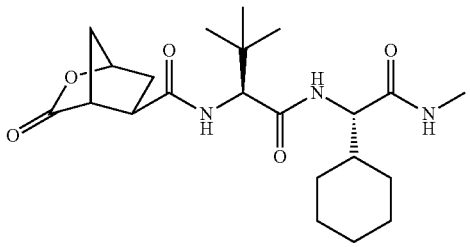 [SMILES: CNC(=O)[C@@H](NC(=O)[C@@H](NC(=O)C1CC2CC1C(=O)O2)C(C)(C)C)C1CCCCC1]

(1R,4R,5R)—N-[(1S)-1-[[[(1S)-1-Cyclohexyl-2-(methylamino)-2-oxoethyl]amino]carbonyl]-2,2-dimethylpropyl]-3-oxo-2-oxabicyclo[2.2.1]heptane-5-carboxamide (72)

To a solution of compound 32 (53 mg, 0.34 mmol) in DMF (9 mL) was added compound 65 (80 mg, 0.28 mmol) and DIEA (290 □L, 1.66 mmol). The solution was cooled to 0° C. and HATU (127 mg, 0.33 mmol) was added. After stirring at 0° C. for 1 h and at it for 1 h the solvent was evaporated, and the crude product was purified by flash column chromatography (EtOAc/toluene 2:1) to give compound 72 (110 mg, 92%) as a white solid.

Example 73

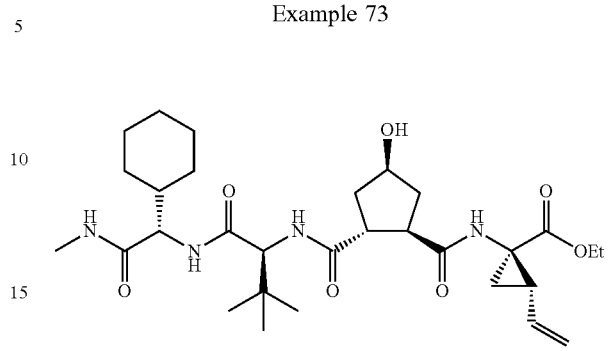

(1R)-1-[[[1R,2R,4R)-2-[[[(1 S)-1-[[[(1 S)-1-Cyclohexyl-2-(methylamino)-2-oxoethyl]amino]carbonyl]-2,2-dimethylpropyl]amino]carbonyl]-4-hydroxycyclopentyl]carbonyl]amino]-2-ethenyl-cyclopropanecarboxylic acid ethyl ester (73)

Compound 72 (60 mg, 0.14 mmol) was dissolved in dioxane (3.5 mL) and $H_2O$ (2.5 mL) and the solution was cooled to 0° C. LiOH (1 M, 280 □L, 0.28 mmol) was added dropwise during 5 min, after which the reaction mixture was stirred at 0° C. for 40 min. The pH was adjusted to 7 using 1 M HCl, and the solvents were evaporated. The residue was suspended in DMF (5 mL) and 1-amino-2-vinyl-cyclopropanecarboxylic acid ethyl ester (32 mg, 0.17 mmol), and DIEA (146 □L, 0.84 mmol) were added. After cooling to 0° C. HATU (64 mg, 0.17 mmol) was added and the mixture was stirred at 0° C. for 1 h and at t for 1 h. The solvent was evaporated and the product was purified using flash column chromatography (EtOAc/MeOH 9:1) to give compound 73 (87 mg, 82%) as a white solid.

Example 74

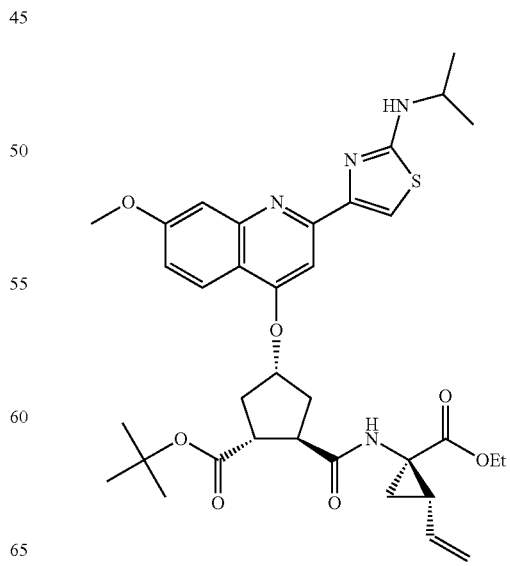

tert-Butyl (1R,2R,4R)-2-[[[(1R)-1-(ethoxycarbonyl)-2-vinylcyclopropyl]amino]carbonyl]-4-[[2-[2-(Isopropylamino)-1,3-thiazol-4-yl]-7-methoxyquinolin-4-yl]oxy]cyclopentanecarboxylate (74)

The title compound was prepared according to the procedure described in example 76 method A but with the use of compound 34 instead of compound 73. (Note: 4 equivalents of Ph₃P and DIAD were used. Chromatography eluent Toluene/EtOAc 1:1.)

Example 75

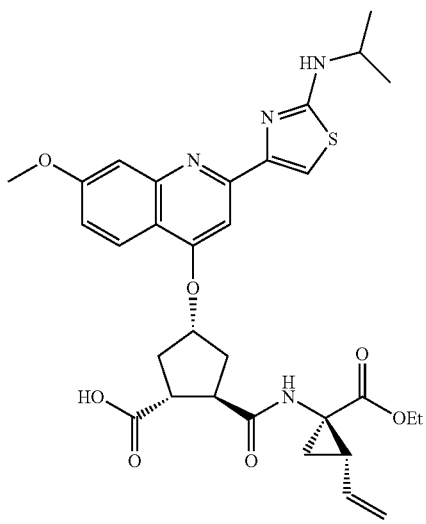 [SMILES: C=C[C@@H]1C[C@]1(NC(=O)[C@@H]1C[C@@H](Oc2cc(-c3csc(NC(C)C)n3)nc3cc(OC)ccc23)C[C@H]1C(=O)O)C(=O)OCC]

(1R,2R,4R)-2-[[[(1R)-1-(Ethoxycarbonyl)-2-vinyl-cyclopropyl]amino]carbonyl]4-[[2-[2-(isopropyl-amino)-1,3-thiazol-4-yl]-7-methoxyquinolin-4-yl]oxy]cyclopentanecarboxylic acid (75)

To a solution of compound 74 (20 mg, 30 umol) in CH₂Cl₂ (2 mL) was added TFA (2 mL) and Et₃SiH (10 uL, 63 umol). After 2 h the volatiles were evaporated and the product was used without any purification step. Compound 75:18 mg, quant as a white solid.

Example 76

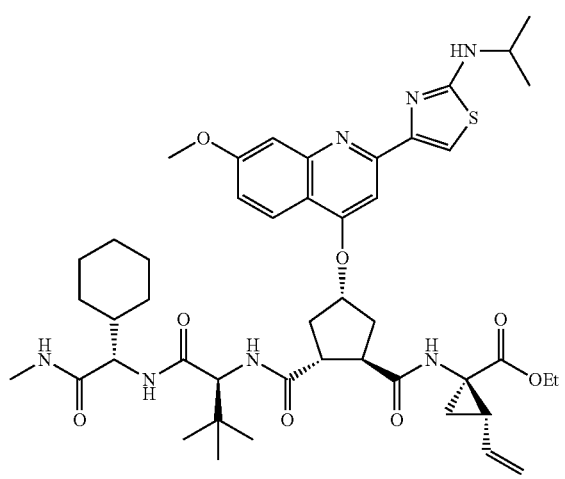 [SMILES: C=C[C@@H]1C[C@]1(NC(=O)[C@@H]1C[C@@H](Oc2cc(-c3csc(NC(C)C)n3)nc3cc(OC)ccc23)C[C@H]1C(=O)N[C@H](C(=O)N[C@H](C(=O)NC)C1CCCCC1)C(C)(C)C)C(=O)OCC]

(1R)-1-[[[(1R,2R,4S)-2-[[[(1S)-1-[[[(1 S)-1-Cyclo-hexyl-2-(methylamino)-2-oxoethyl]amino]carbonyl]-2,2-dimethylpropyl]amino]carbonyl]-4-[[7-methoxy-2-[2-[(1-methylethyl)amino]-thiazolyl]-4-quinolinyl]oxy]cyclopentyl]carbonyl]amino]-2-ethenyl-cyclopropanecarboxylic acid ethyl ester (76)

Method A:
To a solution of compound 73 (59 mg, 0.10 mmol) in dry THF (4 mL) was added the quinoline 71 (49 mg, 0.16 mmol) and Ph₃P (65 mg, 0.25 mmol). After cooling to 0° C. DIAD (50 uL, 0.25 mmol) was added dropwise during 5 min. The solution was stirred at 0° C. for 1 h and at it for 48 h. The solvent was evaporated and the remainder was purified using flash column chromatography (CHCl₃/2 M NH₃ in MeOH 95:5) to give compound 76 (9 mg, 10%) as a white solid.
Method B:
Compound 75 was coupled to compound 65 according to the procedure in example 72 which gave the title compound (82%).

Example 77

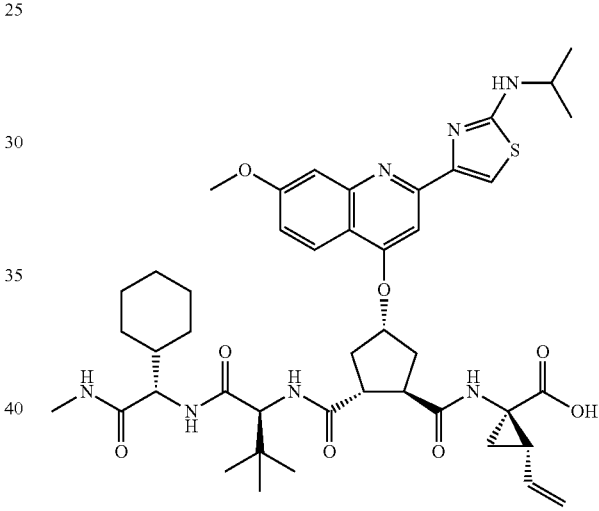

(1R)-1-[[[(1R,2R,4S)-2-[[[(1S)-1-[[[(1 S)-1-Cyclo-hexyl-2-(methylamino)-2-oxoethyl]amino]carbonyl]-2,2-dimethylpropyl]amino]carbonyl]-4-[[7methoxy-2-[2-[(1-methylethyl)amino]-4-thiazolyl]-4-quinolinyl]oxy]cyclopentyl]carbonyl]amino]-2-ethenyl-cyclopropanecarboxylic acid (77)

Compound 76 (8 mg, 9 μmol) was dissolved in a mixture of MeOH (150 μL) and THF (100 uL). A solution of LiOH (1 mg, 42 μmol) in H₂O (25 □L) was added and the mixture was stirred at 50° C. overnight. The solution was neutralized with HOAc and evaporated. The residue was suspended in CH₂C and washed with H₂O. The organic phase was evaporated to give the title compound (8 mg, quant.) as a white solid.
¹H-NMR (MeOH-d₄, 400 MHz) (mixture of rotamers): δ 0.60-1.33 (m, 21H), 1.35-1.73 (m, 12H), 1.90-2.42 (m, 2H), 2.51-2.75 (m, 6H), 3.20-3.38 (m, 1H), 3.85 (s, 3H), 3.95-4.28 (m, 1H), 4.91-5.02 (m, 1H), 5.12-5.23 (m, 1H), 5.64-5.83 (m, 1H), 7.01-7.11 (m, 1H), 7.25-7.40 (m, 1H), 7.42-7.57 (m, 1H), 7.85-8.08 (m, 1H).

Example 78

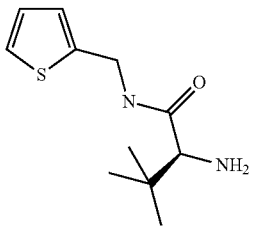

2-Amino-3,3-dimethyl-N-thiophen-2-yl-methyl-butyramide (78)

The title compound was prepared as described in example 61 but with the use of thiophene-2-methylamine instead of aminoindanole followed by removal of the Boc group as described in example 62.

Example 79

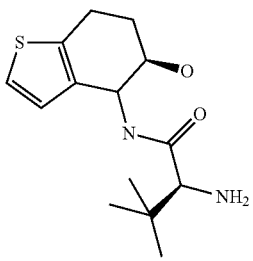 [SMILES: CC(C)(C)[C@H](N)C(=O)NC1c2ccsc2CC[C@H]1O]

2-Amino-N-(6-hydroxy-4,5,6,7-tetrahydro-benzo[b]thiophen-5-yl)-3,3-dimethyl-butyramide (79)

The title compound was prepared as described in example 61 but with the use of 2-amino-4,5,6,7-tetrahydro-benzo[b]thiophen-5-ol instead of aminoindanole followed by removal of the Boc group as described in example 62.

Example 80

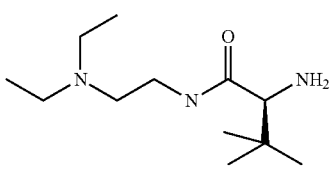 [SMILES: CCN(CC)CCNC(=O)[C@@H](N)C(C)(C)C]

2-Amino-N-(2-diethylamino-ethyl-3,3-dimethyl-butyramide (80)

The title compound was prepared as described in example 61 but with the use of N,N-diethylethylenediamine instead of aminoindanole followed by removal of the Boc group as described in example 62.

Example 81

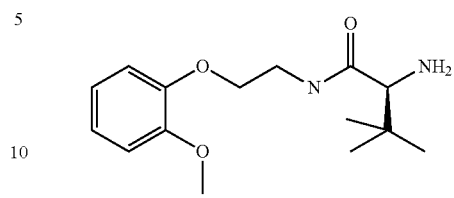

2-Amino-N-[2-(2-methoxy-phenoxy)-ethyl]-3,3-dimethyl-butyramide (81)

The title compound was prepared as described in example 61 but with the use of 2-methoxyphenoxyethylamine instead of aminoindanole followed by removal of the Boc group as described in example 62.

Example 82

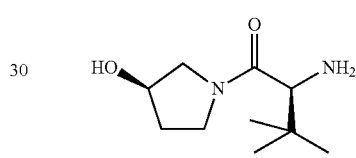

2-Amino-1-(3-hydroxy-pyrrolidin-1-yl)-3,3-dimethyl-butan-1-one (82)

The title compound was prepared as described in example 61 but with the use of (R)-3-pyrrolidinone instead of aminoindanole followed by removal of the Boc group as described in example 62.

Example 83

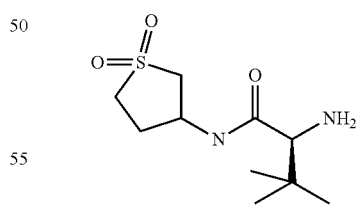

2-Amino-N-(1,1-dioxo-tetrahydro-1-thiophen-3-yl)-3,3-dimethyl-butyramide (83)

The title compound was prepared as described in example 61 but with the use of 2-methoxyphenoxyethylamine instead of aminoindanole followed by removal of the Boc group as described in example 62.

Example 84

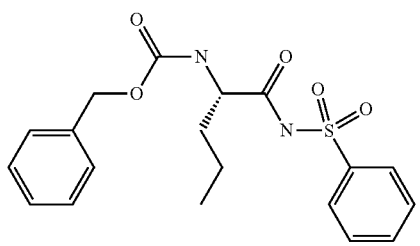 [SMILES: CCC[C@H](NC(=O)OCc1ccccc1)C(=O)NS(=O)(=O)c1ccccc1]

Carbamic acid, [(1 S)-1-[[(phenylsulfonyl)amino]carbonyl]butyl]-, phenylmethyl ester (84)

To a stirred solution of Z-Nva-OH (150 mg, 0.59 mmol) in THF (6 mL), CDI (400 mg, 2.4 mmol) was added. The slurry was agitated for 30 min at RT followed by the addition of DBU (200 uL, 1.3 mmol) and a solution of benzenesulfonamide (250 mg, 1.59 mmol) in THF (2 mL). The mixture was stirred at 60° C. for 48 hrs followed by concentration to dryness. The residue was dissolved in MeOH and subjected to HPLC purification to give the title compound (118.5 mg, 0.304 mmol). Purity>95% by HPLC. M–H$^+$ 389.0, +Na 412.96.

Example 85

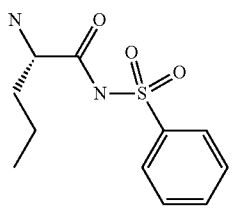 [SMILES: CCC[C@H](N)C(=O)NS(=O)(=O)c1ccccc1]

(2S)-2-Amino-N-(phenylsulphonyl)pentanamide (85)

Compound 84 was dissolved in MeOH (5 mL) followed by the addition of Pd/C and subjected to hydrogenation for 2 hrs. The slurry was filtered through celite, washed with MeOH and concentrated to dryness to give the title compound. Yield 100%. M+H$^+$ 257.3.

Example 86

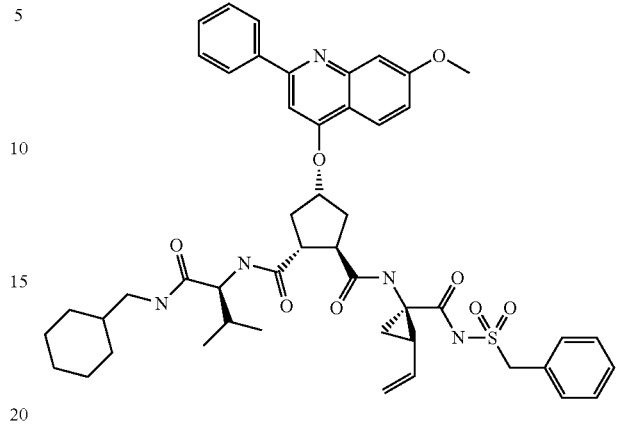

4-(7-Methoxy-2-phenyl-quinolin-4-yloxy)-cyclopentane-12-dicarboxylic acid 1-{[1-(cyclohexylmethyl-carbamoyl)-2-methyl-propyl]-amide} 2-[(1-phenyl-methanesulfonylaminocarbonyl-2-vinyl-cyclopropyl)-amide] (86)

N-(tert-Butoxycarbonyl)-L-valine was attached to Argonaut resin PS-TFP as described in example 60 followed by reaction with cyclohexanemethylamine as described in example 61 and removal of the Boc group as described in example 62. The afforded amine was used in a coupling reaction with compound 35 as described in example 39 followed by hydrolysis of the ethyl ester as described in example 40 which gave 1-{2-[1-(cyclohexylmethyl-carbamoyl)-2-methyl-propylcarbamoyl]-4-(7-methoxy-2-phenyl-quinolin-4-yloxy)-cyclopentanecarbonyl]-amino}-2-vinyl-cyclopropanecarboxylic add. The afforded add was then treated as described in example 94 but using toluenesulphonamide instead of cyclopropylsulphonamide which gave the title compound. Yield 6%. Purity>95% by HPLC. M+H$^+$ 864.32.

Example 87

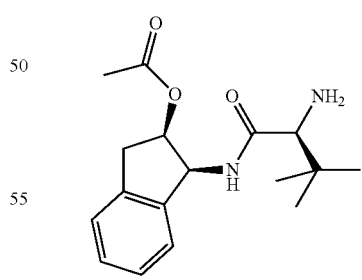

Acetic acid (1S,2R)-1-((2S)-2-amino-3,3-dimethyl-butyrylamino)-indan-2-yl ester (87) A solution of compound 61 (4 g) was kept in pyridine-acetic anhydride 2:1 for 30 min. DCM was added and the solution was washed with citric acid (aq) and NaHCO$_3$ (aq). The organic layer was concentrated to dryness which gave the acetylated product>90% pure by HPLC. The afforded compound was then kept in a solution of 30% TFA In DCM for 1.5 hrs and then

Example 88

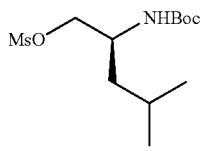

(2S)-Methanesulphonic acid
2-tert.butoxycarbonylamino-4-methyl-pentyl ester
(88)

To a solution of ((S)-1-hydroxymethyl-3-methylbutyl)-carbamic acid tert-butyl ester (25 g, 115 mmol) in dichloromethane (500 mL) cooled by an ice-water bath was successively added disopropylethylamine (35.7 g, 276 mmol) and methanesulphonyl chloride (15.81 g, 138 mmol). The resulting solution was stirred over night during which time the mixture was allowed to gradually warm up to ambient temperature. The mixture was washed successively with water, 10% citric acid (aq), water and saturated NaHCO$_3$ (aq), then dried with Na$_2$SO$_4$ and concentrated to a brown solid (32.6 g, 96%) which was used in the next reaction without further purification.

Example 89

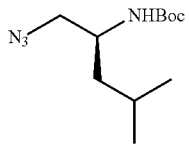 [SMILES: CC(C)C[C@@H](CN=[N+]=[N-])NC(=O)OC(C)(C)C]

ii) ((1 S)-1-Azidomethyl-3-methyl-butyl)carbamic acid tert.butyl ester (89)

The mesylate from example 88 (32.6 g, 110 mmol) was treated with sodium azide (21.45 g, 330 mmol) in DMF at 80° C. for 24 hrs. The solvent was evaporated, the residue was taken up in DCM, filtered and washed with saturated NaHCO$_3$ (aq). The solution was dried with Na$_2$SO$_4$ and concentrated to a brown oil which was purified by flash chromatography using a gradient of ethyl acetate and hexane to afford the title compound as a white solid (19.55 g, 73%).

Example 90

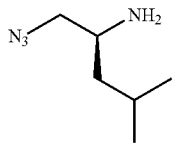

(1S)-1-Azidomethyl-3methyl-butylamine (90)

((1 S)-1-Azidomethyl-3-methyl-butyl)-carbamic acid tert-butyl ester (9.64 g, 39.78 mmol) was treated with TFA (30 mL) in DCM (150 mL) for 3 hrs, the mixture was evaporated under reduced pressure and the residue was dissolved in ethyl acetate and washed with aqueous 1 M K$_2$CO$_3$, dried with Na$_2$SO$_4$ and concentrated to a yellow liquid (4.55 g, 80%).

Example 91

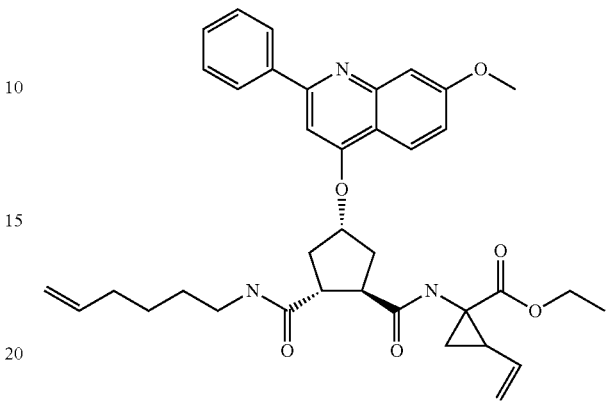

1-{[2-Hex-5-enylcarbamoyl-4-(7-methoxy-2-phenyl-quinolin-4-yloxy)-cyclopentanecarbonyl]-amino}-2-vinyl-cycloprpanecarboxylic acid ethyl ester (91)

The tert.butyl ester of compound 35 was removed by treatment with triethylsilane as described in Example 39. The afforded add (724 mg, 1.33 mmol), hex-5-enylamine hydrochloride (271 mg, 2 mmol) and diisopropylethylamine (1.85 ml, 10.65 mmol) was dissolved in DMF (20 ml) and cooled to 0° C. After 30 min. HATU (608 mg, 1.6 mmol) was added and the flask was removed from the ice-bath. The reaction was followed with LC-MS. After 3 h the reaction mixture was extracted between EtOAc (100 ml) and aqueous sodium hydrogencarbonate (15 ml). The EtOAc-phase was dried over magnesium sulphate, evaporated and purified by chromatography on silica gel (25% EtOAc in hexane→50% EtOAc in hexane) to give the pure title product (726 mg, 87%). MS (M+H$^+$): 525.8

Example 92

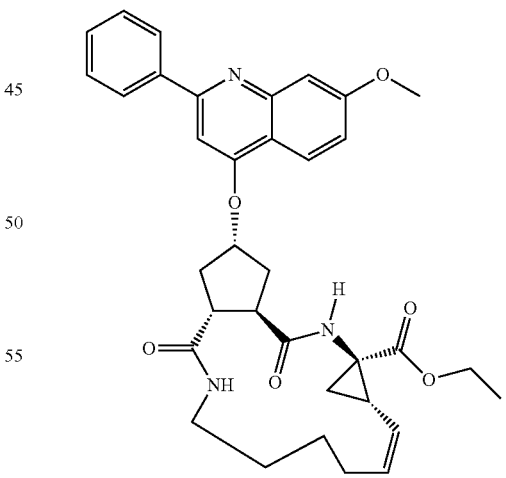

17-(7-Methoxy-2-phenyl-quinolin-4-yloxy)-2,14-dioxo-3,13-diaza-tricyclo[13.3.0.0*4,6*]octadec-7-ene-4-carboxylic acid ethyl ester (92)

Compound 91 (363 mg, 0.58 mmol) was dissolved in degassed dichloromethane (100 ml). Hoveyda-Grubbs catalyst 2nd generation (26 mg, 0.041 mmol) was added and the mixture was refluxed under argon atmosphere overnight. The reaction mixture was evaporated on silica and purified by silica gel chromatography (50% EtOAc in hexane→70% EtOAc in hexane) to give the pure title product (111 mg, 32%). MS (M+H$^+$): 597.7

Example 93

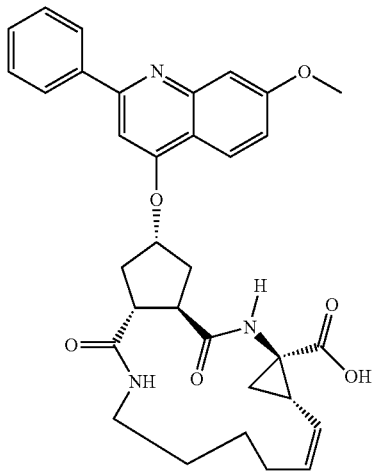 [SMILES: COc1ccc2c(O[C@H]3C[C@H]4C(=O)NCCCC/C=C\[C@@H]5C[C@@]5(C(=O)O)NC(=O)[C@@H]4C3)cc(-c3ccccc3)nc2c1]

17-(7-Methoxy-2-phenyl-quinolin-4-yloxy)-2,14-dioxo-3,13-diaza-tricyclo[13.3.0.0*4,6*]octadec-7-ene-4-carboxylic add (93)

Compound 92 (96 mg, 0.159 mmol) was dissolved in tetrahydrofuran (10 ml), methanol (5 ml) and water (4 ml) Lithium hydroxide (40 mg, 1.67 mmol) was dissolved in water (1 ml) and added. The reaction mixture was heated to 65° C. After 3 h the reaction mixture was cooled, acidified with aqueous HCl (pH5), evaporated on silica and purified by silica gel chromatography (10% MeOH in dichloromethane→15% MeOH in dichloromethane) to give the pure title product (65 mg, 72%). MS (M+H$^+$): 569.8

Example 94

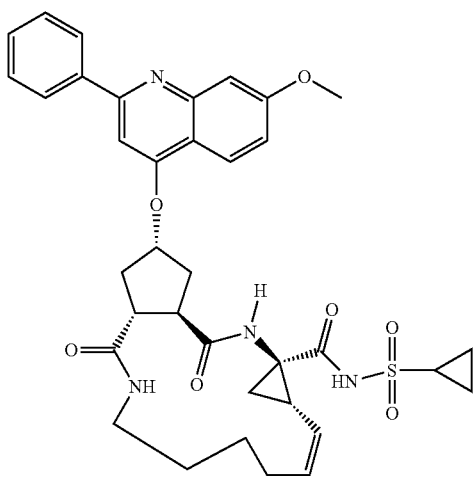 [SMILES: COc1ccc2c(O[C@H]3C[C@H]4C(=O)NCCCC/C=C\[C@@H]5C[C@@]5(C(=O)NS(=O)(=O)C5CC5)NC(=O)[C@@H]4C3)cc(-c3ccccc3)nc2c1]

Cyclopropanesulphonic add [17-(7-methoxy-2-phenyl-quinolin-yloxy)-2,14-dioxo-3,13-diaza-tricyclo [13.3.0.0*4,6*octadec-7-ene-4-carbonyl]-amide (94)

Compound 93 (65 mg, 0.12 mmol), DMAP (21 mg, 0.17 mmol) and EDAC (44 mg, 0.23 mmol) was dissolved in DMF (0.2 ml). The reaction mixture was stirred for 6 h at R.T. whereafter cyclopropylsulfonamide (69 mg, 0.57 mmol) and DBU (80 µl, 0.57 mmol) was added. After stirring at R.T overnight the reaction mixture was extracted between EtOAc (80 ml) and aqueous citric add (10%, 2×15 ml). The organic phase was dried over MgSO$_4$, evaporated on silica and purified twice by chromatography on silica gel (5% MeOH in dichloromethane→15% MeOH in dichloromethane) which gave a syrup. This syrup was dissolved in a small volume acetonitrile and precipitated with ethyl ether to give the pure title product (19 mg, 23%). MS (M+H$^+$): 673.2

Example 95

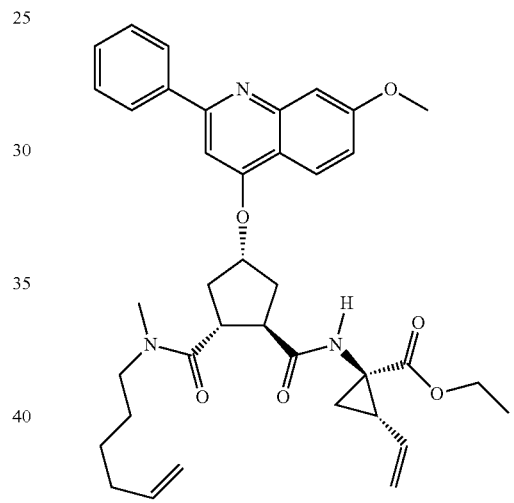

1-{[2-Hex-5-enyl-methyl-carbamoyl)-4-(7-methoxy-2-phenyl-quinolin-4-yloxy)-cyclopentanecarbonyl]-amino-2-vinyl-cyclopropanecarboxylic add ethyl ester (95)

The tert.butyl ester of compound 35 was removed according to the procedure described in Example 39. The afforded acid (850 mg, 1.56 mmol), N-methyl hex-6-enylamine hydrochloride (380 mg, 2.5 mmol) and diisopropylethylamine (2.3 ml, 13.4 mmol) was dissolved in DMF (60 mL) and cooled to 0° C. After 30 min. HATU (0.76 mg, 2.0 mmol) was added and the flask was removed from the ice-bath. The reaction was followed with TLC. After 2 h the reaction mixture was added to 5% citric acid and extracted three times with ethyl acetate. The organic phase was dried over sodium sulphate and evaporated under reduced pressure. The crude product was purified by silica gel chromatography which gave the title product (820 mg, 82%.

Example 96

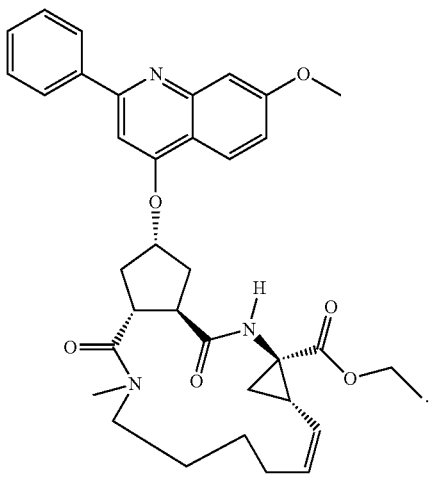 [SMILES: CCOC(=O)[C@@]12C[C@H]1/C=C\CCCCN(C)C(=O)[C@@H]1C[C@H](Oc3cc(-c4ccccc4)nc4cc(OC)ccc34)C[C@H]1C(=O)N2]

17-(7-Methoxy-2-phenyl-quinolin-4-yloxy)-3-methyl-2,14-dioxo-3,13-diaza-tricyclo[13.3.0.0*4,6*]octadec-7-ene-4-carboxylic acid ethyl ester (96)

Compound 95 (648 mg, 1.01 mmol) was dissolved in degassed dichloroethane (500 mL). Hoveyda-Grubbs catalyst 2:nd generation (35 mg, 0.055 mmol) was added and the mixture was refluxed under argon atmosphere overnight. The reaction mixture was evaporated on silica and purified by chromatography on silica gel (30% EtOAc in toluene→50% EtOAc in toluene) to give the pure title product (230 mg mg, 37%). MS (M+H$^+$): 612.8

Example 97

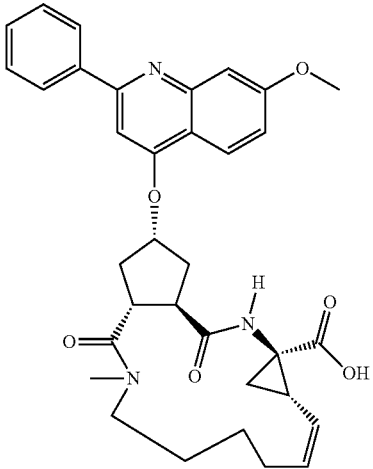 [SMILES: COc1ccc2c(O[C@@H]3C[C@H]4C(=O)N[C@]5(C(=O)O)C[C@H]5/C=C\CCCCN(C)C(=O)[C@@H]4C3)cc(-c3ccccc3)nc2c1]

17-(7-Methoxy-2-phenyl-quinolin-4-yloxy)-13-methyl-2,14-dioxo-3,13-diaza-tricyclo[13.3.0.0*4,6*]octadec-7-ene-4-carboxylic add ethyl ester (97)

Compound 96 (260 mg, 0.42 mmol) was dissolved in 1,4-dioxan (20 mL), 1.0 M Lithium hydroxide (6.0 ml) was added and the mixture was stirred at room temperature overnight and then for six hours at 60° C. The mixture was added to 5% citric acid and extracted 3 times with ethyl acetate. The organic phase was dried over sodium sulphate and evaporated under reduced pressure. The crude product was purified by silica gel chromatography with DCM and 5% MeOH which gave the title product (130 mg, 53%). MS (M+H): 584.7

Example 98

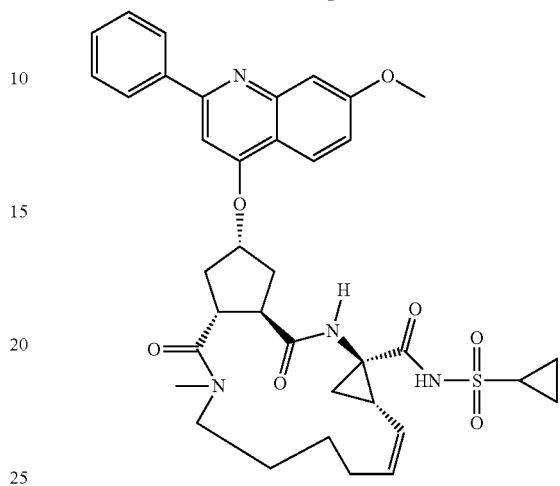

Cyclopropanesulphonic acid [17-(7-methoxy-2-phenyl-quinolin-4-yloxy)-13-methyl-2,14-dioxo-3,13-diaza-tricyclo[13.3.0.0*4,6*octadec-7ene-4-carbonyl]-amide (98)

Compound 97 (58.3 mg, 0.1 mmol), DMAP (18.3 mg, 0.15 mmol) and EDAC (38.7 mg, 0.2 mmol) was dissolved in DMF (1.0 mL). The reaction mixture was stirred overnight at R.T. whereafter cyclopropylsulphonamide (60.5 mg, 0.5 mmol) and DBU (76 µg, 0.5 mmol) was added. After stirring at R.T overnight the reaction mixture was added to 5% citric acid and extracted three times with ethyl acetate. The organic phase was dried over sodium sulphate and evaporated. The afforded residue was purified two times by silica gel chromatography which gave the title product (20 mg). MS (M+H) 687.8.

Example 99

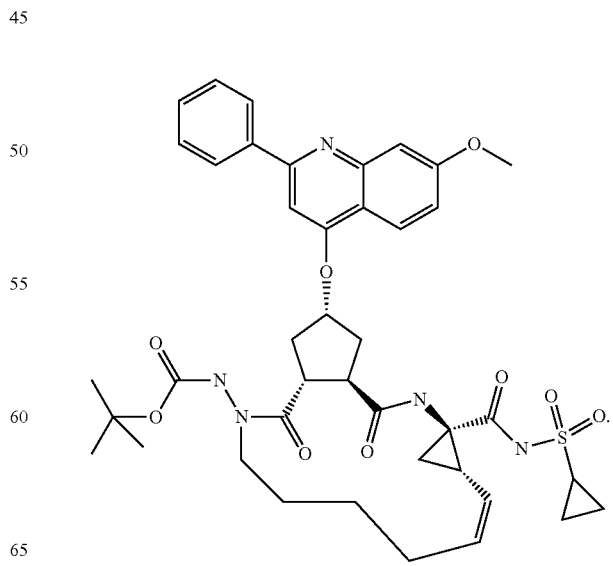

113

[4-Cyclopropanesulphonylaminocarbonyl-17(7-methoxy-phenyl-quinolin-4-yloxy)-2,14-dioxo-3,13-diaza-tricyclo[13.3.0.0*4,6]octadec-7-en-13-yl]-carbamic acid tert.butyl ester (99)

N'-Hex-5-en-(E)-ylidene-hydrazinecarboxylic acid tert-.butyl ester was prepared according to the procedure described in Example 48 and 47 but starting from hex-5-en-ol instead of hept-6-en-ol. Compound 35 was treated as described in Example 48 but using the above described N'-Hex-5-en-(E)-ylidene-hydrazinecarboxylic acid tert.butyl ester instead of the corresponding hept-6-en derivative followed by macrocyclisation as described in Example 49 and hydrolysis of the ethyl ester as described in Example 50 gave the acid. The afforded acid (58 mg, 0.0848 mmol) was dissolved in dry DMF (7 mL) and DIEA was added drop wise during one minute. The solution was stirred at room temperature for 1 h prior to the addition of a solution containing cyclopropylsulfonamide (41 mg, 0.338 mmol), DMAP (41.3 mg, 0.338 mmol) and DBU (50 µL, 0.338 mmol) in dry DMF (1.5 mL). The solution was stirred at room temperature for 5 days. The solution was diluted with EtOAc (50 mL) and washed with sat NaHCO₃. The aqueous phase was extracted with DCM. The combined organic layers were dried, concentrated and subjected to purification by HPLC, which gave the title compound as a white solid (14.3 mg, 0.018 mmol), Purity by HPLC>95%, M+H⁺ 788.3.

Example 100

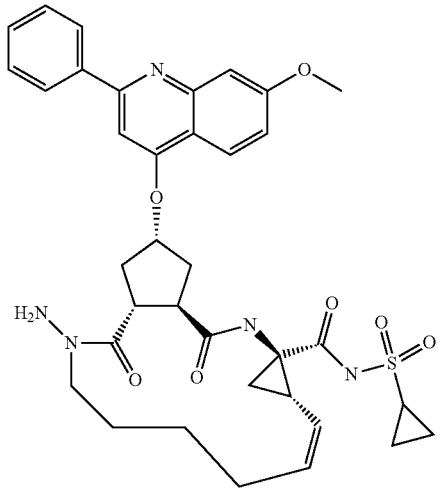

Cyclopropanesulphonic acid[13-amino-17-(7-methoxy-2-phenyl-quinolin-4-yloxy)-2,14-dioxo-3,13-diaza-tricyclo[13.3.0.0*4,6*]octadec-7-ene-4-carbonyl]-amide trifluoroacetic acid salt (100)

Compound 99 (2.4 mg, 0.00304 mmol) was kept in TFA-DCM 1:2 (3 mL) at room temperature for 60 min. Toluene (3 mL) was added. The sample was co-evaporated to dryness to afford the title compound (2.1 mg, 0.0028 mmol) Purity by HPLC>95%. M+H⁺ 688.3.

114

Example 101

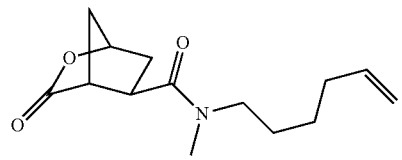 [SMILES: C=CCCCCN(C)C(=O)C1CC2CC1C(=O)O2]

3-Oxo-2-oxa-bicyclo[2.2.1]heptane-5-carboxylic acid hex-5-enyl-methylamide (101)

To HATU (2.17 g, 5.7 mmol) and N-methyl hex-5-enylamine hydrochloride (8.47 mmol) in 5 mL DMF, under argon in an ice bath, were added 1R,4,5R-3-oxo-2-oxa-bicyclo[2.2.1]heptane-5-carboxylic acid (835.6 mg, 5.35 mmol) in 11 mL DMF followed by DIEA (2.80 mL, 16 mmol). After stirring for 40 min, the mixture was stirred at rt for 5 h. The solvent was evaporated, the residue dissolved in EtOAc (70 mL) and washed with saturated NaHCO₃ (10 mL). The aqueous phase was extracted with EtOAc (2×25 mL). The organic phases were combined, washed with saturated NaCl (20 mL), dried over Na₂SO₄, and evaporated. Flash column chromatography (150 g silica gel, 2/1 EtOAc—petroleum ether (PE), TLC detection by aqueous KMnO4, Rf 0.55 in 4/1 EtOAc—PE) gave the compound as a yellow oil (1.01 g, 75%).

Example 102

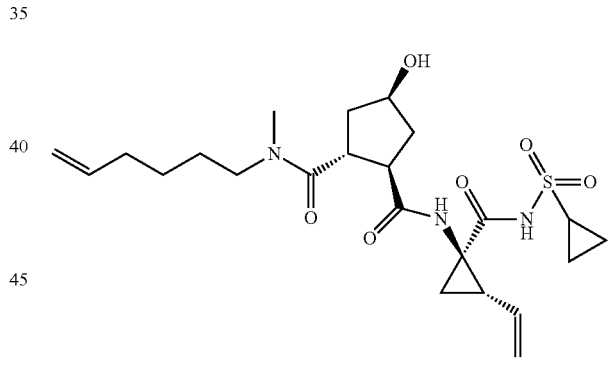

4-Hydroxycyclopentane-1,2-dicarboxylic acid 1-[(1-cyclopropanesulphonylaminocarbonyl-2-vinylcyclopropyl)-amide] 2-(hex-5-enyl-methylamide (102)

LiOH solution (0.15M, 53 mL, 8 mmol) was added to the lactone amide 101 (996 mg, 3.96 mmol) in an ice bath and stirred for 1 h. The mixture was acidified to pH 2-3 with 1N HC and evaporated, co-evaporated with toluene several times, and dried under vacuum overnight (1R,2S)-cyclopropanesulfonic acid (1-amino-2-vinyl-cyclopropanecarbonyl) amide hydrochloride (421 mmol) and HATU (1.78 g, 4.68 mmol) were added. The mixture was cooled in an ice bath under argon, DMF (25 mL) and then DIEA (2.0 mL, 11.5 mmol) were added. After stirring for 30 min, the mixture was stirred at rt for 3 h. After evaporation of solvent, the residue was dissolved in EtOAc (120 mL), washed successively with 0.5 N HCl (20 mL) and saturated NaCl (2×20 mL), and dried over Na$_2$SO$_4$. Flash column chromatography (200 g YMC silica gel, 2-4% MeOH in CH$_2$Cl$_2$ gave white solids (1.25 g, 66%).

Example 103

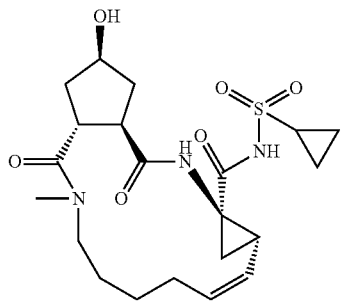 [SMILES: CN1CCCC/C=C\[C@@H]2C[C@@]2(C(=O)NS(=O)(=O)C2CC2)NC(=O)[C@@H]2C[C@H](O)C[C@H]2C1=O]

Cyclopropanesulphonic acid (17-hydroxy-13-methyl-2,14-dioxo-3,13-diazatricyclo[13.3.0.0*4,6*]octadec-7-ene-4-carbonyl)-amide (103)

The cyclopentanol 102 (52.0 mg, 0.108 mmol) was dissolved in 19 mL 1,2-dichloroethane (bubbled with argon prior to use). The Hoveyda-Grubbs 2$^{nd}$ generation catalyst (6.62 mg, 10 mole %) was dissolved in DCE (2×0.5 mL) and added. The green solution was bubbled with Ar for 1 min. Aliquots (4 mL each) were transferred Into five 2 to 5-mL microwave tubes. To the last tube was added 0.8 mL rinsing with solvent. Each tube was heated by microwave (rt to 160° C. In 5 min). All aliquots were combined and the solvent evaporated. Flash column chromatography (silica gel, 3-7% MeOH in CH$_2$Cl$_2$) gave 24.39 mg solids (Rf 0.28 in 10% MeOH—CH$_2$C$_1$ with two spots). The solids were combined with a 9.86-mg sample and subjected to a second chromatography (2-8% MeOH in EtOAc) to give cream solids (23 mg) with 80% of the desired compound (26% yield).

Example 104

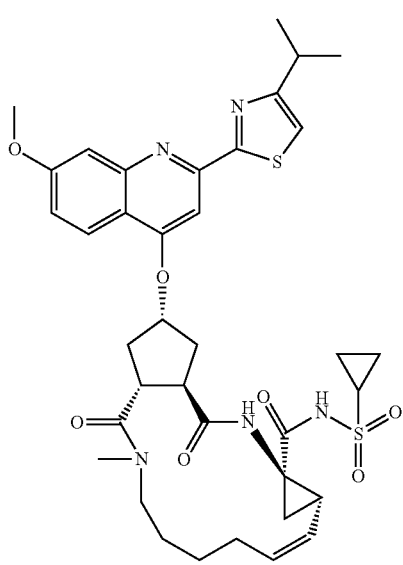 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1]

Cyclopropanesulphonic add {17-[2-(4-isopropylthiazol-2-yl)-7-methoxyquinolin-4-yloxy]-13-methyl-2,14-dioxo-3,13-diazatricyclo[13.3.0.0*4,6*]octadec-7-ene-4-carbonyl)-amide (104)

DIAD (22 uL, 0.11 mmol) was added to a mixture of the metathesis product 103 (23 mg), 2-(4-isopropyl-1,3-thiazol-2-yl)-7-methoxyquinolin-4-ol (24 mg, 0.08 mmol), and PPh$_3$(30 mg, 0.11 mmol) in 1 mL dry THF, in an ice bath. The mixture was stirred at rt overnight and then evaporated. The residue (1.2 mL of a 1.5-mL MeCN solution) was purified by prep-HPLC (Hypercarb 7 uL 100×212 mm, 40% to 99% aqueous MeCN in 10 min) to give 3.18 mg MV062308 as cream solids (13% yield). 1H NMR (DMSO-d6) δ ppm: major rotamer 0.99 (m, 2H), 1.11 (m, 2H), 1.20-1.30 (m, 2H), 1.37 and 1.38 (2d, J=7.0 Hz, 6H), 1.46-1.58 (m, 2H), 1.70 (m, 1H), 1.85 (m, 1H), 1.90 (dd, J=8.5, 6.0 Hz, 1H), 2.08 (br, 1H), 2.26 (m, 1H), 2.38 (m, 1H), 2.52-2.82 (m, 3H), 2.90-2.97 (m, 2H), 3.06 (s, 3H), 3.21 (m, 1H), 3.40-3.56 (m, 2H) 3.97 (s, 3H), 4.60 (m, 1H), 5.04 (m, 1H), 5.41 (br, 1H), 5.66 (m, 1H), 7.16 (m), 7.58 (br), 8.02 (m), 10.92 (s, 1H)

Example 105

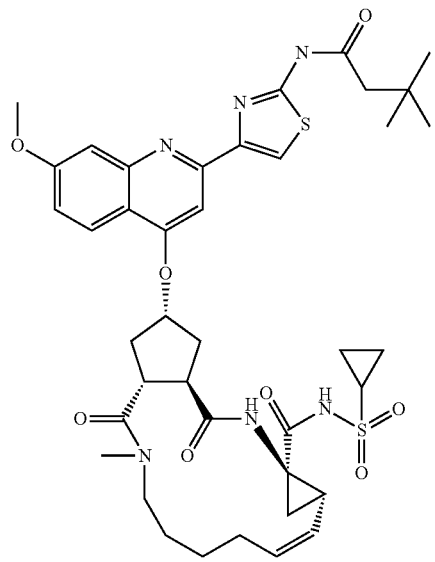 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3csc(NC(=O)CC(C)(C)C)n3)nc2c1]

N-{4-[4-Cyclopropanesulphonylaminocarbonyl-13-methyl-2, 14-dioxo-3,13-diaza-tricyclo[13.3.0.0*4,6]octadec-7-en-17-yloxy)-7methoxy-quinolin-2-yl]-thiazol-2-yl}-3,3dimethylbutyramide (106)

Treatment of compound 103 with 4-hydroxy-7-methoxy-2-[2-(2,2-dimethylbutanoyl)aminothiazol-4-yl]quinoline as described hi Example 104 gave the title compound.

LCMS: retention time 2.30 in gradient 30%-80% B in 3 min(flow. 0.8 mL/min, UV 220 nm, ACE C8 3×5 mm; mobile phase A 10 mM NH$_4$Ac in 90% H$_2$O, B 10 mM NH$_4$Ac in 90% ACN), (M+1)$^+$=807.

Example 106

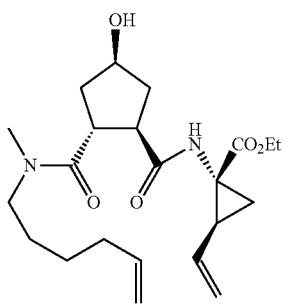 [SMILES: C=CCCCCN(C)C(=O)[C@@H]1C[C@@H](O)C[C@H]1C(=O)N[C@]1(C(=O)OCC)C[C@H]1C=C]

1-{[2-(Hex-5-enyl-methyl-carbamoyl)-4-hydroxy-cyclopentanecarbonyl]-amino}-2-vinyl-cyclopropanecarboxylic acid ethyl ester (106)

Reaction of compound 101 as described hi example 102 but using 1-amino-2-vinylcyclopropanecarboxylic acid ethyl ester instead of (1R,2S)-cyclopropanesulfonic acid (1-amino-2-vinyl-cyclopropanecarbonyl)amide hydrochloride gave the title compound.

Example 107

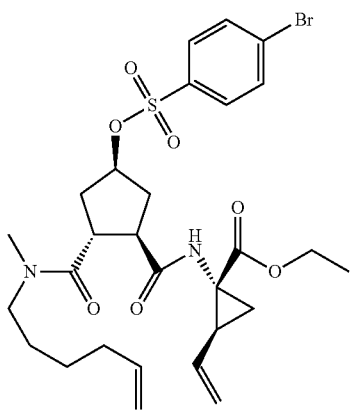 [SMILES: C=CCCCCN(C)C(=O)[C@@H]1C[C@@H](OS(=O)(=O)c2ccc(Br)cc2)C[C@H]1C(=O)N[C@]1(C(=O)OCC)C[C@H]1C=C]

1-{(4-(4-Bromo-benzensulphonyloxy-2-(hex-5-enyl-methyl-carbamoyl)-cyclopentanecarbonyl-amino}2-vinyl-cyclopropanecarboxylic add ethyl ester (107)

Compound 106 (115 mg, 0.286 mmol) was dissolved in toluene 5 ml and dichloromethane 1 ml. DABCO (2.2.2-diazobicyclooctane) (96 mg, 0.857 mmol, 3 eq.) was added to the solution, followed by addition of BsCl (109 mg, 0.428 mmol, 1.5 eq). The reaction was stirred at room temperature overnight, diluted with toluene (+10% ethyl acetate), washed with saturated sodium bicarbonate, brine, dried over sodium sulphate and evaporated. The desired product was obtained by column chromatography (eluent EtOAc) $R_f$ 0.25). Conversion 80%. Yield 106 mg.

Example 108

17-(4-Bromo-benzensulphonyloxy)-13-methyl-2,14-dioxo-3,13-diaza-tricyclo[13.3.0.0*4,6*]octadec-7-ene-4-carboxylic acid ethyl ester (108)

Compound 107 (106 mg, 0.169 mmol) was dissolved in dichloromethane (40 ml) and degassed by bubbling nitrogen through the solution for 20 min. Hoveyda-Grubbs catalyst 1st generation (10 mg, 0.017 mmol, 10 mol %) was then added and the mixture was refluxed under nitrogen atmosphere overnight. The reaction mixture was then cooled down to room temperature and MP-TMT palladium scavenger (approx 100 mg) was added and stirred for 2.5 h. The scavenger was removed by filtration and washed with 50 ml of dichloromethane. The solution obtained was concentrated by rotary evaporation. The crude was purified by column chromatography (EtOAc) to give 61 mg of product. Yield 60%.

Example 109

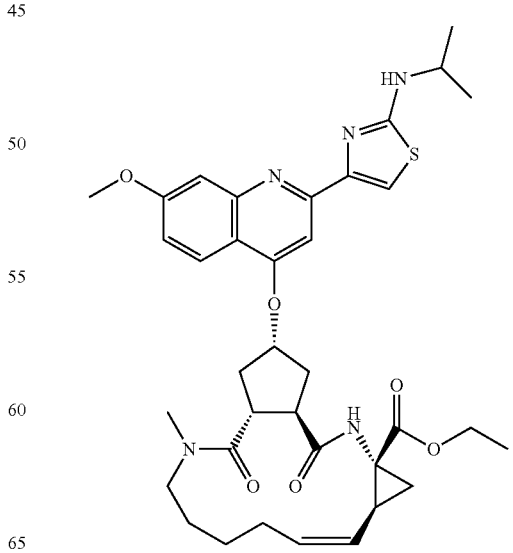

17-[2-(2-isopropylamino-triazol-4-yl)-7-methoxy-quinolin-4-yloxy]-13-methyl-2,14-dioxo-3,13-diaza-tricyclo[13.3.0.0*4,6*]octadec-7-ene-4-carboxylic acid ethyl ester (109)

2-(Isopropylamino-thiazol-4-yl)-7-methoxy-quinolin-4-ol (220 mg, 0.7 mmol) (prepared as described in WO 00/59929) was dissolved in 7 mil of NMP (N-methyl pyrrolidinone), one spoon of $Cs_2CO_3$ was added, stirred at 60° C. for 1.5 h. Then compound 108 (150 mg, 0.24 mmol) was added. The reaction mixture was stirred at 80° C. overnight. Was diluted with chloroform and washed with sodium bicarbonate, brine. Water phases were back-extracted with chloroform. The combined organic layers were dried over sodium sulphate and evaporated. The crude product was purified by preparative HPLC (Gilson) (MeOH—$H_2O$, 65%) to give 21 mg of product (yield 13%) as well as 12 mg of isomer.

Example 110

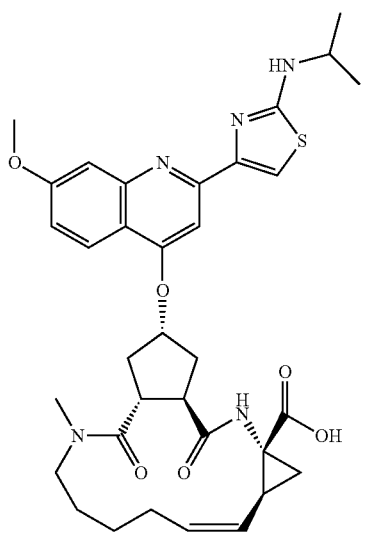 [SMILES: COc1ccc2c(O[C@@H]3C[C@H]4C(=O)N[C@]5(C(=O)O)C[C@H]5/C=C\CCCCN(C)C(=O)[C@@H]4C3)cc(-c3csc(NC(C)C)n3)nc2c1]

17-[2-(2-Isopropylamino-thiazol-4-yl)-7-methoxy-quinolin-4-yloxy]-13-methyl-2,14-dioxo-3,13-diaza-tricyclo[13.3.0.0*4,6*]octadec-7-ene-4-carboxylic acid (110)

To the solution of the ester 109 (21 mg, 0.031 mmol) in a mixture of THF (02 ml) and methanol (0.3 ml) was added solution of LiOH (4 mg, 0.17 mmol) in 0.15 ml water. The resulting mixture was stirred at 60° C. for 3.5 h. After cooling to room temperature, acetic acid was added (30 eq). The mixture was co-evaporated with toluene. The residue was distributed between chloroform and water, the water phase was extracted with chloroform 3 times, the organic phases were combined, dried over sodium sulphate and evaporated which gave 20 mg of pure product (yield 99%).

Example 111

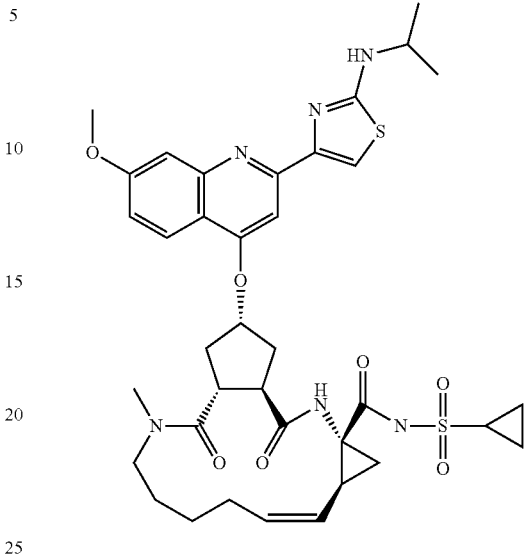

Cyclopropanesulphonic acid {17-[2-(2-isopropylamino-thiazol-4-yl)-7-methoxy-quinolin-4-yloxy]-13-methyl-2,14-dioxo-3,13-diaza-tricyclo[(13.3.0.0*4,6*]octadec-7-ene-4-carbonyl} amide (111)

The acid 110 (20 mg, 0.15 mmol), DMAP (28 mg, 0.225 mmol) and EDAC (58 mg, 0.3 mmol) was dissolved in DMF (1.5 mL). The reaction mixture was stirred overnight at R.T. whereafter cyclopropylsulphonamide (91 mg, 1.125 mmol) and DBU (114 µL, 0.75 mmol) was added. After stirring at RT overnight the reaction mixture was added to 5% citric add and extracted three times with chloroform. The organic phase was dried over sodium sulphate and evaporated. The afforded residue was purified by preparative HPLC to give the title product (5.6 mg) (yield 24%).

Assays

The compounds of the invention are conveniently assayed for activity against the NS3 protease of flavivirus such as HCV using conventional in vitro (enzyme) assays or cell culture assays.

A useful assay is the Bartenshlager replicon assay disclosed in EP 1043399. An alternative replicon assay is described in WO 03064416.

A convenient enzyme assay involving the inhibition of full-length hepatitis C NS3 is essentially as described in Poliakov, 2002 Prot Expression & Purification 25 363 371.

Briefly, the hydrolysis of a depsipeptide substrate, Ac-DED(Edans)EEAbu$_\psi$[COO]ASK(Dabcyl)-$NH_2$ (AnaSpec, San José, USA), is measured spectrofluorometrically in the presence of a peptide cofactor, KKGSV-VIVGRIVLSGK, as described by Landro, 1997 Biochem 36 9340-9348. The enzyme (1 nM) is incubated in a buffer such as 50 mM HEPES, pH 7.5, 10 mM DTT, 40% glycerol, 0.1% n-octyl-β-D-glucoside, with 25 µM cofactor and inhibitor at say 30° C. for 10 min, whereupon the reaction is initiated by addition of substrate, typically 0.5 µM substrate. Inhibitors are typically dissolved in DMSO, sonicated for 30 s and vortexed. The solutions are generally stored at −20° between measurements.

An alternative enzyme assay is described in WO 0399316 and employs an HCV NS3/4A protease complex FRET peptide assay. The purpose of this in vitro assay is to measure the inhibition of HCV NS3 protease complexes, derived from the BMS, H77C or J4168 strains, as described below, by compounds of the present invention. This assay provides an indication of how effective compounds of the present invention would be in inhibiting HCV proteolytic activity.

Serum is taken from an HCV-infected patient. An engineered full-length cDNA template of the HCV genome (BMS strain) was constructed from DNA fragments obtained by reverse transcription-PCR (RT-PCR) of serum RNA and using primers selected on the basis of homology between other genotype I a strains. From the determination of the entire genome sequence, a genotype I a was assigned to the HCV isolate according to the classification of Simmonds et al. (See P Simmonds, K A Rose, S Graham, SW Chan, F McOmish, B C Dow, E A Follett, P L Yap and H Marsden, J. Clin. Microbiol., 31(6), 1493-1503 (1993)). The amino add sequence of the nonstructural region, NS2-58, was shown to be >97% identical to HCV genotype Ia (H77C) and 87% identical to genotype Ib (J4L6S). The infectious clones, H77C (I a genotype) and J4L6S (b genotype) can be obtained from R. Purcell (NIH) and the sequences are published in Genbank (AAB6703, see Yanagi, M., Purcell, R. H., Emerson, S. U. and Bukh. Proc. Natl. Acad. Sd. U.S.A. 94 (16) 8738-8743 (1997); AF054247, see Yanagi, M., St Claire, M., Shapiro, M., Emerson, S. U., Purcell, R. H. and Bukhj, Virology 244 (1), 161 (1998)).

The BMS, H77C and J4L6S strains are conventional for production of recombinant NS3/4A protease complexes. DNA encoding the recombinant HCV NS3/4A protease complex (amino acids 1027 to 1711) for these strains were manipulated as described by P. Gallinari at al. (see Gallinari P, Paolini C, Brennan D, Nardi C, Steinkuhler C, De Francesco R. Biochemistry. 38(17):562032, (1999)). Briefly, a three-lysine solubilizing tall was added at the 3'-end of the 3 0 NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation can be introduced by PCR at amino acid position 1454 to prevent the autolytic cleavage in the NS3 helices domain. The variant DNA fragment can be cloned in the pET21b bacterial expression vector (Novagen) and the NS34A complex can be expressed in *Escherichia coli* strain BL21 (DE3) (invitrogen) following the protocol described by P. Gallinari et a. (see Gallinari P, Brennan D, Nardi C, Brunetti M, Tomei L, Steinkuhler C, De Francesco R., J Virol. 72(8):6758-69 (1998)) with modifications. Briefly, NS3/4A expression can be induced with 0.5 mM isopropyl beta-D thiogalactopyranoside (IPTG) for 22 hr at 20'C. A typical fermentation (I0 I) yields approximately 80 g of wet cell paste. The cells are resuspended in lysis buffer (IO mL/g) consisting of 25 mM N-(2Hydroxyethyl)Piperazine-N'-(2-Ethane Sulfonic acid) (HEPES), pH7.5, 20% glycerol, 500 mM Sodium Chloride (NaCl), 0.5% Triton-X100, I ug/mL lysozyme, 5 mM Magnesium Chloride (MgCl$_2$), I ug/mL Dnasel, 5 mM beta-Mercaptoethanol (BME), Protease inhibitor—Ethylenediamine Tetraacetic acid (EDTA) free (Roche), homogenized and incubated for 20 mine at VC. The homogenate is sonicated and clarified by ultra-centrifugation at 235000 g for 1 hr at 4° C.

Imidazole is added to the supernatant to a final concentration of 15 mM and the pH adjusted to 8. The crude protein extract is loaded on a Nickel Nitrilotriacetic add (Ni-NTA) column pre-equilibrated with buffer B (25n-tM 2.0 HEPES, pH8 20% glycerol, 500 mM NaCl, 0.5% Triton-XIOO, 15 mM imidazole, 5 mM BME). The sample is loaded at a flow rate of 1 mL/min. The column is washed with 15 column volumes of buffer C (same as buffer B except with 02% Triton-X100). The protein s eluted with 5 column volumes of buffer D (same as buffer C except with 200 mM imidazole).

NS3/4A protease complex-containing fractions are pooled and loaded on a desalting column Superdex-S200 pre-equilibrated with buffer D (25 MM HEPES, pH7.5, 20% glycerol, 300 mM NaCl, 0.2% Triton-XIOO, IO mM BME). Sample is loaded at a flow rate of ImUmin. NS3/4A protease complex3 0 containing fractions are pooled and concentrated to approximately 0.5 mg/mL The purity of the NS3/4A protease complexes, derived from the BMS, H77C and J4L6S strains, are typically judged to be greater than 90% by SDS-PAGE and mass spectrometry analyses.

The enzyme is generally stored at −80'C, thawed on ice and diluted prior to use in assay buffer. The substrate used for the NS3/4A protease assay, is conveniently RET S 1 (Resonance Energy Transfer Depsipeptide Substrate; AnaSpec, inc. cat #22991)(FRET peptide), described by Taliani at al. in Anal. Biochem. 240(2):6067 (1996). The sequence of this peptide is loosely based on the NS4A/NS4B natural cleavage site except there is an ester linkage rather than an amide bond at the cleavage site. The peptide substrate is incubated with one of the three recombinant NS3/4A complexes, in the absence or presence of a compound of the present invention, and the formation of fluorescent reaction product was followed in real time using a Cytofluor Series 4000. Useful reagents are as follow: HEPES and Glycerol (Ultrapure) can be obtained from GIBCO-BRL. Dimethyl Sulfoxide (DMSO) is obtained from Sigma. Beta-Mercaptoethanol is obtained from Bio Rad.

Assay buffer: 50 m.M HEPES, pH7.5; 0.15M NaCl; 0.1% Triton; 15% Glycerol; 10 mM BME. Substrate: 2 uM final concentration (from a 2 mM stock 2 0 solution in DMSO stored at −20'C). HCV NS3/4A type Ia (Ib), 2-3 nM final concentration (from a 5 uM stock solution in 25 mM HEPES, pH7.5, 20% glycerol, 300 m.M NaCl, 0.2% Triton-X100, 10 mM BME). For compounds with potencies approaching the assay limit, the assay can be made more sensitive by adding 50 ug/mL BSA to the assay buffer and/or reducing the end protease concentration to 300 pM.

The assay is conveniently performed in a 96-well polystyrene black plate from Falcon. Each well contains 25 ul NS3/4A protease complex in assay buffer, 50 ul of a compound of the present invention in 10% DMSO/assay buffer and 25 ul substrate in assay buffer. A control (no compound) is also prepared on the same assay plate. The enzyme complex is mixed with compound or control solution, typically for 1 min before initiating the enzymatic reaction by the addition of substrate. The assay plate is generally read immediately using a spectrophotometer such as a Cytofluor Series 4000 (Perspective Biosystems). The instrument is conveniently set to read an emission of 340 nm and excitation of 490 nm at 25'C. Reactions are generally followed for approximately 15 minutes.

The percent inhibition can be calculated with the following equation.

$$100.-[(dF_{inh}/dF_{con}) \times 100]$$

where dF is the change in fluorescence over the linear range of the curve. A nonlinear curve fit is applied to the inhibition-concentration data, and the 50% effective concentration ($IC_{50}$) is calculated by the use software such as Excel XI-fit software using the equation:

$$y=A+((B-A)(1+((C/x)^\wedge D))).$$

Enzyme assays conveniently utilize a fluorescence resonance energy transfer (FRET) principle to generate a spectroscopic response to an HCV NS3 serine protease catalyzed NS4A/4B cleavage event. The activity is typically measured in a continuous fluorometric assay using an excitation wavelength of 355 nm and emission wavelength of 500 nm. The initial velocity may be determined from 10 minutes continuous reading of increased fluorescence intensities as a result of the NS3 protease catalyzed cleavage event.

An alternative enzyme assay can be carried out as follows:

Materials

Recombinant HCV NS3 full length enzyme can be prepared as shown in Poliakov at at Protein Expression & purification 25 (2002) 363-371. The NS4A cofactor conveniently has an amino acid sequence of KKGSVVIVGRIV-LSGK (commercially available), generally prepared as a 10 mM stock solution in DMSO. The FRET-substrate (Ac-Asp-Glu-Asp(EDANS)-Glu-Glu-Abu-ψ-(COO)Ala-Ser-Lys (DABCYL)-NH2, MW1548.60 can be purchased from AnaSpec RET S1, CA. USA) and is typically prepared as a 1.61 mM stock solution in DMSO. Aliquots (50 µl/tube) should be wrapped with aluminum foil to protect from direct light and stored in −20° C.

Reference compound-1, N-1725 with a sequence of AcAsp-D-Gla-Leu-Ile-Cha-Cys, MW 830.95 may be purchased from BACHEM, Switzerland and is generally prepare as a 2 mM stock solution in DMSO and stored in aliquots in −20° C.

1M HEPES buffer may be purchased from invitrogen Corporation, storage at 20° C. Glycerol may be purchased from Sigma, 99% purity.

CHAPS, 3-[(3-Cholamidopropyl)dimethylammonio]-1-propanesulfonate: may be purchased from Research Organics, Cleveland, Ohio 44125, USA. MW614.90 DTT, DL-Dithiothreitol (Cleland Reagent DL-DT) 99% purity, MW.1542 Storage: +4° C.

DMSO may be purchased from SDS, 13124 Peypin, France. 99.5% purity.

TRIS, ultra pure (TRIS-(hydroxymethylaminomethane), may be purchased from ICN Biomedicals Inc.

Sodium Chloride, may be obtained from KEBOlab AB.

N-dodecyl-β-maltoside, minimum 98%, may be purchased from Sigma, storage −20° C.

Equipment

Microtiter plates (white clinlplate, ThermoLab Systems cat no. 9502890

Eppendorf pipettes

Biohit pipette, multi dosing

Ascent fluorimeter, flterpai ex 355 nm, em500 nm

Method

Experimental Procedure:

10 mM stack solutions of the compounds are made in DMSO. The stock solutions are stored in room temperature while testing and placed in −20° C. at long-time storage.

Assay Buffer A:

50 mM HEPES buffer, pH=7.5, 40% Glycerol, 0.1% CHAPS

Storage: room temperature.

10 mM DTT (stored in aliquots at −20° C. and added fresh at each experiment)

Assay Buffer B:

25 mM TRIS pH7.5, 0.15 M NaCl, 10% glycerol, 0.05% n-dodecyl-β-D-maltoside 5 mM DTT (stored in aliquots at −20° C. and added fresh at each experiment)

Assay Sequence:

Preparation of Reaction Buffer (for One Date. 100Reactions)(Buffer A)

1. Prepare 9500 µl assay buffer (HEPES, pH=7.5, 40% glycerol and 0.1% CHAPS in de ionized water. Add DTT giving a final concentration of 10 mM (freshly prepared for every run).
2. Thaw rapidly the NS3 protease
3. Add 13.6 µl NS3 protease and 13.8 µl NS4A peptide and mix properly. Leave the mixture for 15 minutes in room temperature.
4. Place the enzyme stock solution back into liquid nitrogen or −80° C. as soon as possible.

Preparation of Reaction Buffer (for One Plate, 100Reactions) (Buffer B)

5. Prepare 9500 µl assay buffer (TRIS, pH=7.5, 0.16 M NaCl, 0.5 mM EDTA, 10% glycerol and 0.05% n-dodecyl β-D-maltoside in de ionized water. Add DTT giving a final concentration of 5 mM (freshly prepared for every run).
6. Thaw the NS3 protease rapidly.
7. Add 27.2 µl NS3 protease and 13.6 µl NS4A peptide and mix property. Leave the mixture for 15 minutes in room temperature.
8. Place the enzyme stock solution back into liquid nitrogen or −80° C. as soon as possible.

Preparation of Inhibitor/Reference Compound

Make a dilution series of the inhibitors in DMSO to 100× the final concentrations 10, 1, 0.1, 0.01 and 0.001 µM. The final DM80 concentration in 100 µl total reaction volume is 1%.

Make a dilution series of the reference compound, N-1725 in DMSO to 100× the final concentrations 120, 60, 30, 15, 7.5 and 3.75 nM.

Eight enzyme control wells are needed for every run.

Blank wells contain 95 µL buffer (without NS3 PR), 1 µL DMSO and 5 µL substrate.

Preparation of FRET Substrate

Dilute the substrate stock solution (1.61 mM) with assay buffer to 40 µM working solution. Avoid exposure to light.

Assay Sequence

Use 96-well cliniplate, the total assay volume per well is 100 µl.

1. Add 95 µL of assay buffer to each well
2. Add 1 µl inhibitor/reference compound
3. Pre incubate for 30 minutes at room temperature
4. Start the reaction by adding 5 µL 40 µM substrate solution (final concentration 2 µM)
5. Read continuously for 20 minutes at ex=355 nm and em=500 nm, monitoring the increased fluorescence per minute.
6. Plot the progression curve (within linear range, 8-10 time points) and determine the slope as an initial velocity with respect to each individual inhibitor concentration.
7. Calculate % inhibition with respect to enzyme control.

Treatment of Results

The result is expressed as % inhibition at a certain concentration (screen) or as a Ki value in nM or µM.

Calculation of % inhibition: The initial velocity is determined from 10 minutes continuous reading of increased fluorescence intensities as a result of the NS3 protease catalyzed cleavage event. The change in slope for the inhibitor compared to the enzyme control gives the % inhibition at a certain concentration.

Calculation of Ki: All inhibitors are treated as if they follow the rules of competitive inhibition. The $IC_{50}$ value is calculated from the inhibition values of a series of inhibitor concentrations. The calculated value it used in the following equation: $K_i = IC_{50}/(1+S/Km)$ Plotting of the graph is done by help of two calculation programs: Grafit and Graphpad Various compounds of the invention exemplified above displayed $IC_{50}$s in the range 1 nM to 6.9 micromolar and $ED_{50}$s in the sub-micromolar to micromolar range in the above assays.

Drug Escape Resistance Pattern and Rate

Replicon cultures in microtitre plates can be used to determine resistance development rates and to select out drug escape mutants. The compounds being tested are added at concentrations around their $ED_{50}$ using, say, 8 duplicates per concentration. After the appropriate replicon incubation period the protease activity in the supernatant or lysed cells is measured.

The following procedure is followed at subsequent passages of the cultures. Virus produced at the concentration of test compound showing >50% of the protease activity of untreated infected cells (SIC, Starting Inhibitory Concentration) are passaged to fresh replicon cultures. An aliquot, say, 15 µl supernatant from each of the eight duplicates are transferred to replicon cells without the test compound (control) and to cells with test compound at the same concentration, and additionally two respectively fivefold higher concentrations. (See the table below) When the viral component of replicon propagation (for example as measured by HCV protease activity) is permitted at the highest non-toxic concentration (5-40 µM), 2-4 parallel wells are collected and expanded to give material for sequence analysis and cross-wise resistance.

Key:
Viral Growth Emitted
Virus production inhibited

| Pass 1 | Pass 2 | Pass 3 | Pass 4 | Pass 5 |
|---|---|---|---|---|
| SIC | No compound | | | |
| | SIC | No compound | | |
| | 5 × SIC | SIC | | |
| | 25 × SIC | 5 × SIC | No compound | |
| | | 25 × SIC | 5 × SIC | No compound |
| | | | 25 × SIC | 5 × SIC |
| | | | 125 × SIC | 25 × SIC |
| | | | | 125 × SIC |

Alternative methods for assessing activity on drug escape mutants include the preparation of mutant enzyme bearing the distinctive mutation for use in standard Ki determinations as shown above. For example WO 04/039970 describes constructions allowing access to HCV proteases bearing the 155, 156 and/or 168 drug escape mutants arising from the selective pressure of BILN-2061 and VX-950. Such constructs can then be engineered into replicon vectors in place of the wild type protease, thereby allowing ready assessment in a cellular assay, of whether a given compound is active against a give drug escape mutant.

P450 Metabolism

The metabolism of compounds of the invention through the main isoforms of the human cytochrome system P450 are conveniently determined in baculovirus infected insect cells transfected with human cytochrome P450 cDNA (supersomes) Gentest Corp. Woburn USA.

The test compounds at concentrations 0.5, 5 and 50 µM are incubated in duplicate in the presence of supersomes overexpressing various cytochrome P450 isoforms, including CYP1A2+P450 reductase, CYP2A6+P450 reductase, CYP2C9-Arg 144+P450 reductase, CYP2C19+P450 reductase, CYP2D6-Val 374+P450 reductase and CYP3A4+P 450 reductase. Incubates contain a fixed concentration of cytochrome P450 (eg 50 pmoles) and are conducted over 1 hour. The involvement of a given isoform in the metabolism of the test compound is determined by UV HPLC chromatographically measuring the disappearance of parent compound.

The invention claimed is:

1. A compound of formula VIga:

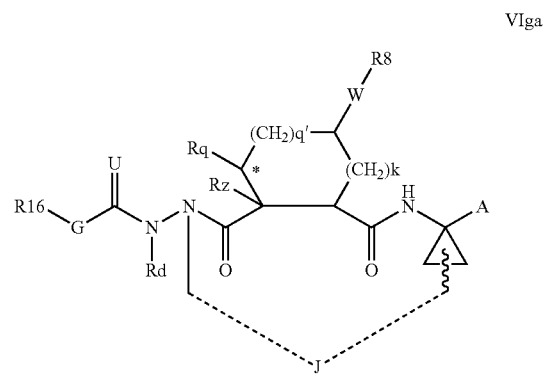

wherein
A is $C(=O)OR^1$ or $C(=O)NHSO_2R^2$; wherein
  $R_1$ is hydrogen or $C_1$-$C_6$alkyl; and
  $R_2$ is $C_1$-$C_6$alkyl, $C_0$-$C_6$alkylcarbocyclyl, or $C_0$-$C_3$alkylheterocyclyl, each of which is optionally substituted with 1 to 3 substituents which are each independently halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, Y—NRaRb, Y—O—Rb, YC(=O)Rb, Y—(C=O)NRaRb, Y—NRaC(=O)Rb, Y—NHSOpRb, Y—S(=O)pRb, YS(=O)pNRaRb, Y—C(=O)ORb, or Y—NRaC(=O)ORb;
Y is independently a bond or $C_1$-$C_3$alkylene;
p is independently 1 or 2;
Ra is independently H or $C_1$-$C_3$alkyl;
Rb is independently H, $C_1$-$C_6$alkyl, $C_0$-$C_3$alkylcarbocyclyl, or $C_0$-$C_3$alkylheterocyclyl;
Rd is H or $C_1$-$C_3$alkyl;
q' is 0 and k is 1;
Rz is H, or together with the asterisked carbon forms an olefinic bond;
Rq is H or $C_1$-$C_6$alkyl;
W is —O— or —S—;
$R_8$ is a ring system containing 1 or 2 saturated, partially saturated or unsaturated rings, each of which has 4-7 ring atoms and each of which has 0 to 4 hetero atoms selected from S, O, and N, the ring system being optionally spaced from W by a $C_1$-$C_3$alkyl group; any of which $R^8$ groups can be optionally mono, di, or tri substituted with $R^9$, wherein
$R_9$ is independently halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, YNRaRb, Y—O—Rb, Y—C(=O)Rb, Y—(C=O)NRaRb, Y—NRaC(=O)Rb, Y-NHSOpRb, YS(=O)pRb, Y—S(=O)pNRaRb, Y—C(=O)ORb, or Y—NRaC(=O)ORb; wherein said carbocyclyl or heterocyclyl moiety is optionally substituted with $R^{10}$; wherein $R_{10}$ is $C_1$-$C_6$alkyl, $C_3$-$C_7$cycloalkyl, $C_1$-$C_6$alkoxy, amino, sulfonyl, ($C_1$-$C_3$ alkyl)sulfonyl, $NO_2$, OH, SH, halo, haloalkyl, carboxyl, or amido;

J is a single 3 to 10-membered saturated or partially unsaturated alkylene chain, which chain is optionally interrupted by one to three heteroatoms that are each independently —O—, —S—, or —$NR^{12}$—, and wherein 0 to 3 carbon atoms in the chain are optionally substituted with $R^{14}$;

$R_{12}$ is H, $C_1$-$C_6$ alkyl, $C_3$-$C_6$cycloalkyl, or $COR^{13}$;

$R_{13}$ is $C_1$-$C_6$alkyl, $C_0$-$C_3$alkylcarbocyclyl, or $C_0$-$C_3$alkylheterocyclyl;

each $R^{14}$ is independently H, $C_1$-$C_6$alkyl, $C_1$-$C_6$haloalkyl, $C_1$-$C_6$alkoxy, hydroxyl, halo, amino, oxo, thio, or $C_1$-$C_6$ thioalkyl;

G is —O—, —NRy-, or NRjNRj-;

Ry is H or $C_1$-$C_3$alkyl;

Rj is H;

U is =O or is absent;

$R_{16}$ is H; or $R^{16}$ is $C_1$-$C_6$alkyl, $C_0$-$C_3$alkylcarbocyclyl, or $C_0$-$C_3$alkylheterocyclyl, any of which can be substituted with halo, oxo, nitrile, azido, nitro, $C_1$-$C_6$alkyl, $C_0$-$C_3$alkylcarbocyclyl, $C_0$-$C_3$alkylheterocyclyl, $NH_2CO$—, Y—NRaRb, Y—O—Rb, YC(=O)Rb, Y—(C=O)NRaRb, Y—NRaC(=O)Rb, Y-NHSOpRb, Y—S(=O)pRb, YS(=O)pNRaRb, Y—C(=O)ORb, or Y—NRaC(=O)ORb;

or a pharmaceutically acceptable salt thereof.

2. The compound according to claim 1, wherein $R^2$ is $C_1$-$C_6$alkyl, $C_0$-$C_3$alkylaryl, $C_3$-$C_7$cycloalkyl, or phenyl, each of which is optionally substituted with 1 to 3 substituents which are each halo, oxo, nitrile, azido, nitro, $C_1$-$C_6$alkyl, $C_0$-$C_3$alkylcarbocyclyl, $C_0$-$C_3$alkylheterocyclyl, $NH_2C(=O)$—, Y—NRaRb, Y—O—Rb, YC(=O)Rb, Y—(C=O)NRaRb, Y—NRaC(=O)Rb, Y-NHSOpRb, Y—S(=O)pRb, YS(=O)pNRaRb, Y—C(=O)Orb, or Y—NRaC(=O)ORb.

3. The compound according to claim 1, wherein said compound has the partial structure that is:

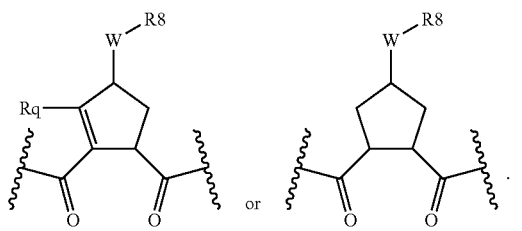

4. The compound according to claim 3, wherein Rq is $C_1$-$C_3$ alkyl.

5. The compound according to claim 1, wherein A is C(=O)$OR^1$, wherein $R^1$ is H or $C_1$-$C_6$ alkyl.

6. The compound according to claim 1, wherein W is —O—.

7. The compound according to claim 1 wherein $R^8$ is optionally substituted $C_0$-$C_3$alkylcarbocyclyl or optionally substituted $C_0$-$C_3$alkylheterocyclyl.

8. The compound according to claim 7, wherein $R^8$ is 1-naphthylmethyl, 2-naphthylmethyl, benzyl, 1-naphthyl, 2-napthyl, or quinolinyl any of which is unsubstituted, mono, or disubstituted with $R^9$ as defined.

9. The compound according to claim 8, wherein $R^8$ is:

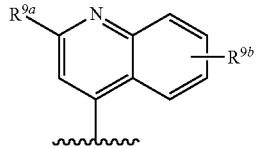

wherein $R^{9a}$ is $C_1$-$C_6$alkyl; $C_1$-$C_6$alkoxy; thio$C_1$-$C_3$alkyl; amino optionally substituted with $C_1$-$C_6$alkyl; $C_0$-$C_3$alkylaryl; $C_0$-$C_3$alkylheteroaryl, or $C_0$-$C_3$alkylheterocyclyl, said aryl, heteroaryl or heterocycle being optionally substituted with $R^{10}$ wherein $R^{10}$ is $C_1$-$C_6$alkyl; $C_0$-$C_3$alkyl; $C_3$-$C_7$cycloalkyl; $C_1$-$C_6$alkoxy; amino optionally mono- or di-substituted with $C_1$-$C_6$alkyl; amide; or $C_1$-$C_3$alkylamide; and $R^{9b}$ is $C_1$-$C_6$alkyl, $C_1$-$C_6$-alkoxy, amino, di($C_1$-$C_3$alkyl) amino, ($C_1$-$C_3$alkyl)amide, $NO_2$, OH, halo, trifluoromethyl, or carboxyl.

10. The compound according to claim 9, wherein $R^{9a}$ is aryl or heteroaryl, either of which is optionally substituted with $R^{10}$ as defined.

11. The compound according to claim 9, wherein $R^{9a}$ is:

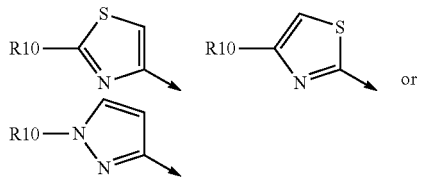

wherein $R^{10}$ is H; $C_1$-$C_6$alkyl; $C_0$-$C_3$alkylcycloalkyl; amino optionally mono- or di-substituted with $C_1$-$C_6$alkyl; amido; or ($C_1$-$C_3$alkyl)amide.

12. The compound according to claim 9, wherein $R^{9a}$ is optionally substituted phenyl.

13. The compound according to claim 9, wherein $R^{9b}$ is $C_1$-$C_6$-alkoxy.

14. The compound according to claim 1, wherein J is a 4 to 7-membered saturated or unsaturated, all carbon alkylene chain.

15. The compound according to claim 1, wherein $R^{16}$ is H, $C_1$-$C_6$alkyl, or $C_3$-$C_6$cycloalkyl.

16. A pharmaceutical composition comprising a compound as defined in claim 1 and a pharmaceutically acceptable carrier.

17. The pharmaceutical composition of claim 16, further comprising an additional HCV antiviral.

18. The pharmaceutical composition of claim 17, wherein the additional HCV antiviral is a nucleoside analogue polymerase inhibitor, a protease inhibitor, ribavirin, or interferon.

19. A method of treating hepatitis C virus (HCV) infection comprising administering to an individual afflicted with or at risk of HCV infection, an effective amount of a compound of claim 1.

20. The method of claim 19, further comprising administering to the individual, an additional HCV antiviral.

21. The method of claim 20, wherein the additional HCV antiviral is a nucleoside analogue polymerase inhibitor, a protease inhibitor, ribavirin, or interferon.

* * * * *